United States Patent [19]
Lagarias et al.

[11] Patent Number: 6,046,014
[45] Date of Patent: Apr. 4, 2000

[54] PHYTOFLUORS AS FLUORESCENT LABELS

[75] Inventors: John Clark Lagarias, Davis; John Thomas Murphy, San Francisco, both of Calif.

[73] Assignee: The Regents of the University of California, Oakland, Calif.

[21] Appl. No.: 08/904,871

[22] Filed: Aug. 1, 1997

Related U.S. Application Data

[60] Provisional application No. 60/023,217, Aug. 2, 1996.
[51] Int. Cl.[7] .................................................. G01N 33/53
[52] U.S. Cl. ............................ 435/7.7; 530/350; 435/183
[58] Field of Search .............................. 530/350; 435/183

[56] References Cited

U.S. PATENT DOCUMENTS

| | | | |
|---|---|---|---|
| 4,542,104 | 9/1985 | Stryer et al. | 436/536 |
| 4,859,582 | 8/1989 | Stryer et al. | 435/6 |

OTHER PUBLICATIONS

White, Prinicples of Biochemistry, McGraw–Hill, Inc. p. 215, 1973.

*Primary Examiner*—Scott W. Houtteman
*Attorney, Agent, or Firm*—Majestic, Parsons, Siebert & Hsue, P.C.

[57] ABSTRACT

This invention provides new fluorescent molecules useful for detection of target entities. In particular, it relates to fluorescent adducts comprising an apoprotein and a bilin.

27 Claims, 14 Drawing Sheets

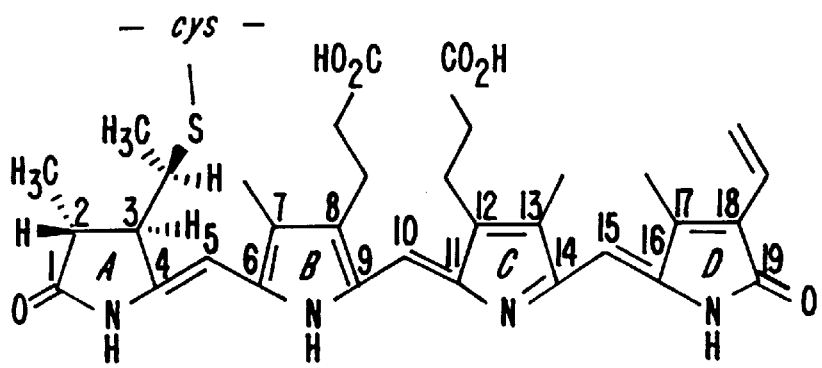
Pr FORM OF PHYTOCHROME
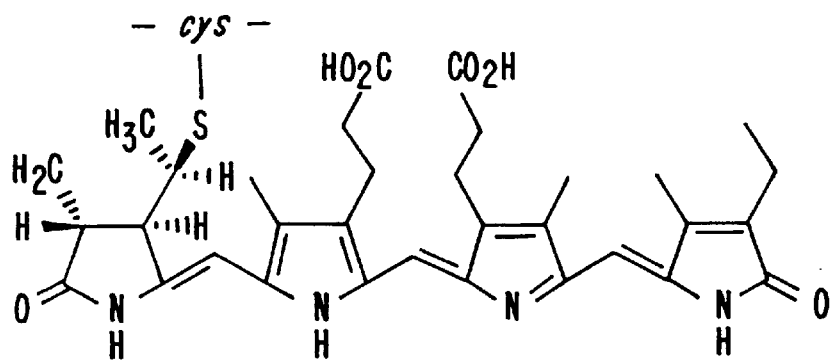
PHYCOCYANIN
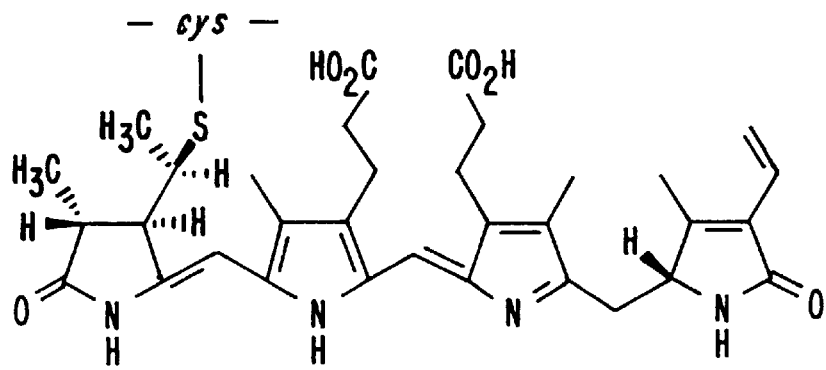
PHYCOERYTHRIN
FIG. 1.

```
Asphya       1 MSSSRPA--SSSSSRNRQSSQARVLAQTTLDAELNAEYE---ESGDSFDYSKLV
Atphya       1 MSGSRPTQSSEGSRRSRHS--ARIIAQTTVDAKLHADFE---ESGSSFDYSTSV
Mcphylb      1 MSTSRMSQSSGEST--AKTKREVRVAQATADAKLNTAFEASAAVGGSFDYTKSV
S6803phyl    1 ------------------------------------------------------M
Consensus    1 msssrpsqssgts---k-s---riiaqtt-daklhavfa---asgdsfdysksv Asphya      50 EAQRDGPPVQQGRSEKV-IAYLQHIQKGKLIQTFGCLLAL-DEKSFNVIAFSEN
Atphya      50 RVTCPVVENQPPRSDKVTTYLHHIQKGKLIQPFGCLLAL-DEKTPKVIAYSEN
Mcphylb     53 GASLNAGSEAIP--SSAVTAYLQRMQRGGITGTFGCMLMV-EEGSFRVRAFSEN
S6803phyl    2 ATTVQLSDQSLRQLETLA-----IHTAHLIGPHC-LVVVLQEPDLTISQISAN
Consensus   44 rat--t--e--p--ekv-taylqriqrggliqpfqcllav-deksfrviaysen Asphya     102 APEMUTTVS-HAVPSVDD---PPRLGIGTNVRSLFSDQGATALHKALGFADVGL
Atphya     103 ASELLTMAS-HAVPSVGE---HPVLGIGTDIRSLFTAPSASALQKALGFCDVEL
Mcphylb    104 AGEMLDLVP-QAVPSM--GQQ-SLIAVGTDIRTLFTSASVSLLEKAAMATDVSV
S6803phyl   49 CTGILGRSPEDL-------------LGRTLGEVFDSFQIDPIQSRLTAGQISS
Consensus   38 apemltlvs-havpsvg------pvlgigtdvrtlftapsaaalekalgfge-sl Asphya     152 INPILVQCKTSFKPFY---AIVHRATGCLVV-DFKPVKPTEFPAT-AAGALQSY
Atphya     153 INPILVHCRTSAKPFY---AIIHRVTGSIII-DFLPVKPYEVPMT-AAGALQSY
Mcphylb    154 MNPVSLQSRAAKKPFF---AVLHRIDVGLVV-DLFPVRPSDPNVS-AAGAMQSH
S6803phyl   89 LNPSKLWARVMGDDPVIFDGVFHRNSDGLLVCELHPAYTSD-----NLPFLGFY
Consensus  135 lnpilvhcktsgkpfy---ailhrvdgglvi-d-hpvkpyd-p-c-aagalqsy Asphya     201 KLAAKAISKI-QSLPGGSMEVLCNTVVKEVFDLTGYDRVMAYKFHEDDHGEVFS
Atphya     202 KLAAKAITRL-QSLPSGSMERLCDTMQEVFELIGYDRVMAYKPHEDDHGEVVS
Mcphylb    203 KLAAKAISRL-QSLPGGDIGLLCDAVEEVRELTGYDRVMAYKPHEDEHGEVIA
S6803phyl  138 HMANAALNRLRQ---QANLRDFYDVIVEEVRRMTGFDRVMLYRPDENNHGDVIA
Consensus  181 hlaakalsrl-qslpgg-mellcdtvmeevreltgydrvmaykphedehgemva
```

*FIG. 6-1.*

| | | |
|---|---|---|
| Asphya | 254 | KITKPGLEFYLGGHYPATDIPQAARLLFMKNKVRMICPCRARSIKVIE--AEAL |
| Atphya | 255 | PVTKPGLECYLQLHYPATCIPQAARFLFMKNKVRMLVDCNAKHARVLQ--DEKL |
| Mcphylb | 256 | EIRRSDLEPYLGLHVPATDIPQAARFDFMKNRVRIICFCSAPPVKVIQ--DPTM |
| S6803phyl | 139 | PDKRDDMEPYLGLHYPESDIPWPARRLFIHNPIRVTPNVYGVAVPLTPAVNPST |
| Consensus | 233 | pi-rpdlepylglhypatdipqaakfllfmkn-vrmlcfcra-pvkviq-dekl |
| | | |
| Asphya | 306 | PFDISLCGSALKAPHSLHLQYMENNNSIASIVMAVVVNENEEDDEAESEQPAQQ |
| Atphya | 307 | SFDLTLCGSTLFAPHSGMLQYMANNDSIANIVMAVVVNEEDGEGD-APDATTQP |
| Mcphylb | 308 | KHPISLAGSTLTGVHGGHAQYMANNGSVASIVMAVIINDNSSEEGATAAGGIL- |
| S6803phyl | 243 | NRAVDLTESILRSAYHQHLTYLKNNGVGASITISLIKDG-------------- |
| Consensus | 282 | pqplslcgstlraphgghlqymanngsias1vmav-indn-eede-g------ |
| | | |
| Asphya | 360 | QKKKKLNGLLVCHHESP--RYVPFPLRYACPFLAQVFAVHVNREF---ELEKQL |
| Atphya | 360 | QKRKRLWGLVVCHNTTP--RFVPFPLRYACEFLAQVFAIHVNKEV---ELDNQM |
| Mcphylb | 361 | HKGRKLWGLVVCHHSSP--RYVPFPLKSACEELMQVFGLQLNNEV---ELSSQL |
| S6803phyl | 282 | ----HLWGLIACHHQTP--KVIPFELRKACEFFGRVVFSNISAQE---DTETFD |
| Consensus | 326 | qk-krlwglvvchhtsp--rfvpfplryaceflmqvfglqlnmel---alasql |
| | | |
| Asphya | 409 | REKNILKMQTMISDMLFREASPLTIVSGTPN-IMDIVKCDGAALLYGGKVWRLR |
| Atphya | 409 | VEKNILRTQTLLCIMLMRDA-PLGIVSQSIN-IMDLVKCDDAALLYKNKIWKLG |
| Mcphylb | 410 | REKHILRTQTLLCFMLLRDA-PMGIVSQSPN-ITDLVKCDCAALFYHGRAWLLC |
| S6803phyl | 327 | YRVQLAEHEAVLLDKMTTAADFVEGLTNHFDRLLGDTGSQCAAICFGEKLILVG |
| Consensus | 374 | raknilrtqtllcdmllrda-plgivsqsph-imdlvkcddaallyggk-wllg |
| | | |
| Asphya | 462 | NAPTESQIHDIAFWLSDVHR-DSTGLSTDSIHDAGYPG-AAALGDMICMAVAK |
| Atphya | 461 | TIPSEFHLQEIASWLCEYHM-DSTGLSTDLLHDAGFPR-ALSLGDSVCGMAAVR |
| Mcphylb | 462 | VIPSEAQVRDIAAALLDSHK-DSTGLSTDSLADAGYPN-ADSLGVSVCGMAAAR |
| S6803phyl | 431 | ETPDEKAVQYLLQWLENREVQD--VFFTSSLSQI-YPD-AVNFKSVASGLLAIP |
| Consensus | 477 | vtptesqikdiaewlleyhg-dstglstddsladaypg-aaalgdavcgmaaak |

FIG. 6-2.

```
Asphya    514  INSKDILFWPRSHTAAEIRIGGAKNDPSDMD------DSRRMHPRLSRKAFLFVV
Atphya    513  ISSKDMIFWPRSHTAGEVRWGGAKHDPDDRD------DARRMRTRSSPKAFLEVV
Mcphylb   514  ITSKDFLFWFRSHAQKEVKWAGAKQEPGDRDREEGEGGRMWPRSSPQAFLTVV
S6803phyl 431  IARHNFLIWFPPEVLQTVNWGGDPNHAYEATQE--DGKIELHPRQSEDLWKEIV
Consensus 477  itskdflfwfrshtakeikwggakhdp-dkd-----dgrrmhprisetkafleVV Asphya    563  KMKSLPWSDYEMDAIHSLQLILRGTL-------NDASKPKREASL
Atphya    562  KTRSLPWKDYEMDAIHSLQLILRNAFK------DSETTDVNTKVI
Mcphylb   568  KQRSLPWEDVEMDAIHSLQLILRGSFQ--DMEGEGGSQQGNKRMI
S6803phyl 483  RLQSLPWQSVEIQSALALKKAIVNLILRQAEELAQLARNLERSNAD
Consensus 525  k-rslpnedyemdaihslqlilrgsfk------dt--------t-i
```

FIG. 6-3.

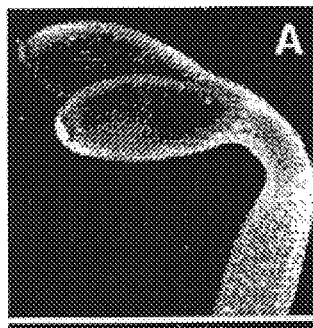
FIG. 9A.
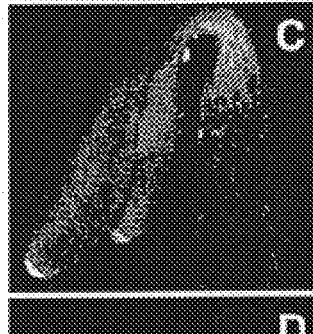
FIG. 9C.
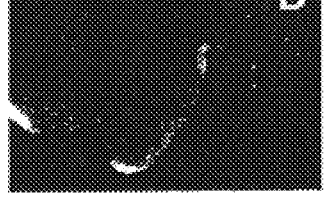
FIG. 9D.
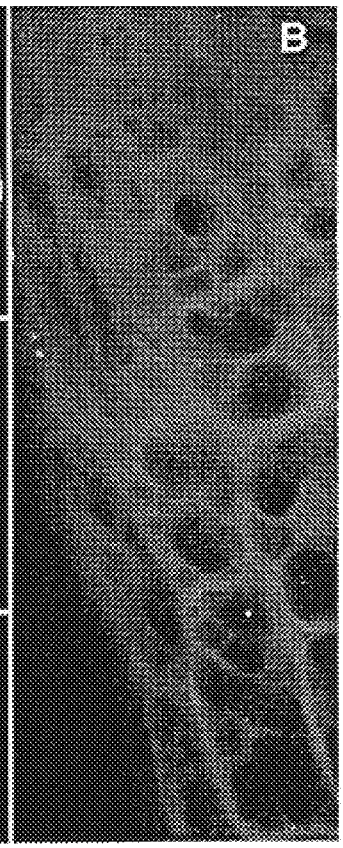
FIG. 9B.
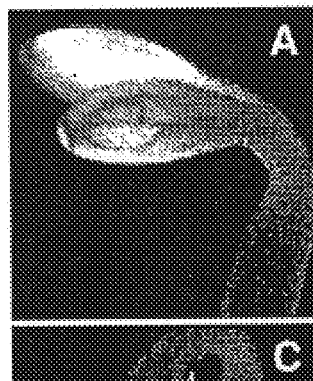
FIG. 9E.
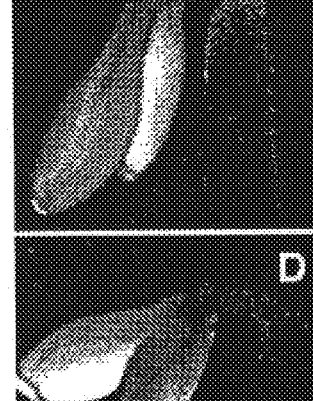
FIG. 9G.
FIG. 9H.
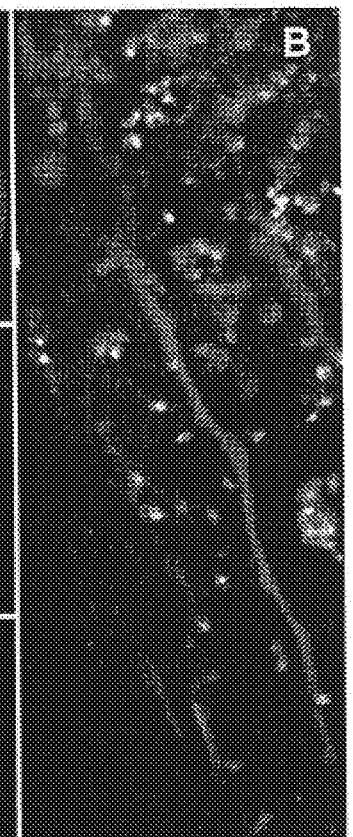
FIG. 9F.

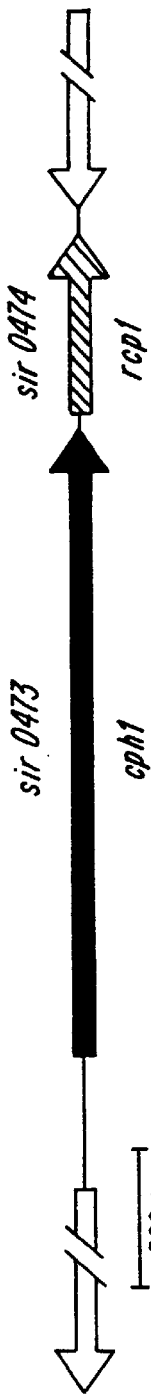

```
MATTVQLSDQSLRQLETLAIHTAHLIQPHSLVVVLQEPDLTISQISANCTGILSRSPEDLIGRTLGEVFDSFQID      75
PIQSRLTAGQISLNPSKLWARVMGDDFVIFDGVFHRNSDGLLVCELIPAYTSDNLPFLGFYHMANAALNRLRQQ      150
ANLRDFYDVIVEEVRRMLQFQRVMLYRRDENNHCDVIAQLHYPESDIPQARFIHNPIRVIPE                  225
DVYGVAVPLTPAVNPSTNRAVDLTESILRSAYHCHLTYLKNMGVASTTISLIKDGHLWGIIACHHQTPKVIPNE      300
LRKAQEPFGRVVFSNISAQEDTETFDYRVQLAEHEAVLIDKMTTAADFVEGLTNHPRLLGLTGSQQAAICFGEK      375
LILVGETRDEKAVQYLLQWLENREVQDVFFLSIQIYPDAVNFKSVASQLLAIPIARHNFLLAFPEVLQTVNW       450
GQDPNHAYEATQEDGKIELHPHQEDLWKLIVRLQSLPWQSVLIQSALALKKAIVNLILRQAEELAQLARNLERS      525
NADLKKFAYIASXDLQEPLNQVSNYVQLLEMRYSEALDEDAKDFIDFAVTGVSLMQTLIDDILTYAKVDTQYAQL    600
TFTDVQEVVDKALANLKQRIEESGAEIEVGSMPAVMADQIQLMOVFQNLIANGIKFAGDKSPKIKIWGDRQEDAW    675
VFAVQDNGIGIDPQFFERIFVIEQRLHTRDEYKGTGMLAICKKIIEGHQGQIWLESNPGEGSTFYFSIPIGN       748
```

FIG. 10A.

```
Rcp1  MSDESNPPFHVTLIMEDSKADSRLYQSVLKTSTIDHILILRLGIAAMAFLQQGEYENSPRPNLLLDLNLPKK    74
RcaF  -----MQTHRLLIIDDEETIQTVQFGIKMAA-GWIVFTASSLFEGIQAQ------TAKPDALLLDVMMPDM    61
CheY  ----MADKELKFLVVDDFSTMRRIMRNLLKELG-FNNVEEAEDIVDALNKLD------AGGYGFVISDWNMPNM    62
SpoOF ----MMNEKILIVDDQYGIRILLNEVFNKEG-----YQTFQAANLIQADLVT-----KERDIVLLDMKIPGM    60

Rcp1  DCREVIALKQNPDLKRLRVVLTTSHNEDVLASYLHVNCVLTKSRNLKDTFKMVQGIESFWLETVTLPAA      147
RcaF  DCIATFKLLQSHSETEQTRVILTAKAQTAEKRQFNDLGVSGVIEKPFNSIDIPEQISRILHW-------   124
CheY  DCLLKTRADGAMSALRVMLVTAEAKKENIIAAQAGASGVVKPFTAATLEEKLNKIFEKLGM--------    129
SpoOF DCLEILKRMKVID--ENRVIIMDYGEIDMIQESKFFGALTHFAKPFDIEIRDAYKKYLPKSN-----   124
```

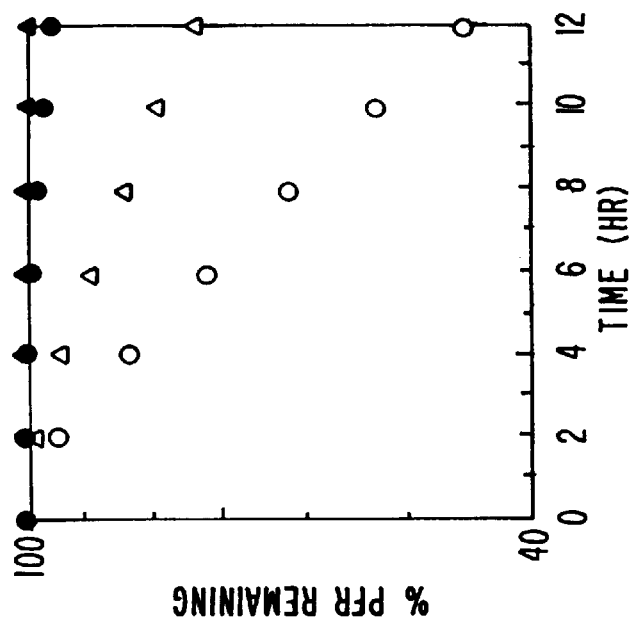
FIG. 11A.
FIG. 11D.
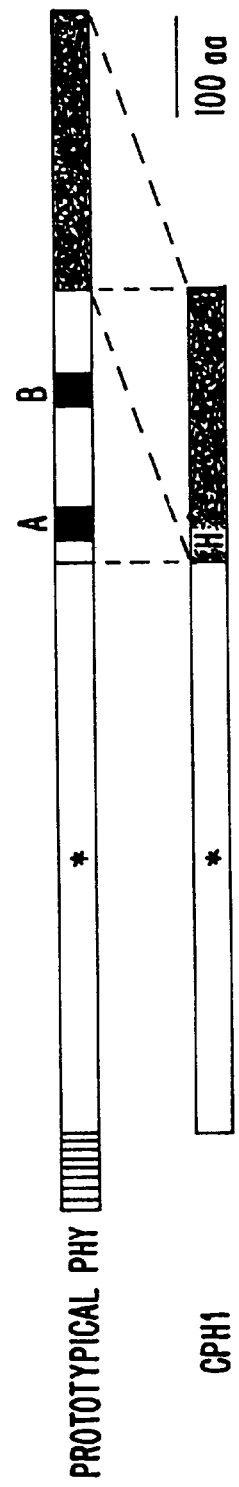
FIG. 11C.

PHYTOFLUORS AS FLUORESCENT LABELS

CROSS-REFERENCE TO RELATED APPLICATIONS

This is a continuation-in-part of U.S. Provisional Application No. 60/023,217, filed on Aug. 2, 1996, which is incorporated herein by reference for all purposes.

This work was supported by a grant (MCB 9206110) from the National Science Foundation, a grant (AMD9503140) from the US Department of Agriculture, and by NIH training grant (5 T32 GM07377-17). The Government of the United States of America may have certain rights in the invention.

FIELD OF THE INVENTION

The present invention relates to new fluorescent molecules useful for detection of target entities. In particular, it relates to fluorescent adducts comprising an apoprotein and a bilin.

BACKGROUND OF THE INVENTION

The phytochromes comprise a family of biliprotein photoreceptors which enable plants to adapt to their prevailing light environment (Kendrick and Kronenberg (1994) Kendrick, Pp. 828 in *Photomorphogenesis in Plants*, Dordrecht, The Netherlands: Kluwer Academic Publishers). All phytochromes possess the ability to efficiently photointerconvert between red light absorbing Pr and far red light absorbing Pfr forms, a property conferred by covalent association of a linear tetrapyrrole (or bilin) with a large apoprotein. Phytochromes from cyanobacteria, to green algae and higher plants consist of a well conserved N-terminal polypeptide, roughly 390–600 amino acids in length (see FIG. 6), to which the bilin prosthetic group phytochromobilin (PΦB) or phycocyanobilin (PCB) is bound.

The N-terminal domain of the phytochrome apoprotein is sufficient for spontaneous covalent attachment of ethylidene containing linear tetrapyrroles, a process requiring neither cofactors nor additional enzymes (Li et al. (1992) *J. Biol. Chem.*, 267: 19204–19210). In higher plants, PΦB is bound to a conserved cysteine residue within the phytochrome apoprotein via a linkage identical to that found in the phycobiliprotein photosynthetic antennae of cyanobacteria, red algae and cryptomonads. The ability of the phytochrome photoreceptor to self assemble with its bilin prosthetic group contrasts with the phycobiliprotein photoreceptors which require separate enzymes for proper bilin attachment (Glazer (1989) *J. Biol. Chem.*, 264: 1–4). Owing to the efficient photointerconversion between Pr and Pfr forms, phytochromes are poorly fluorescent molecules, unlike the phycobiliproteins which are intensely fluorescent and have been exploited as useful probes (see, e.g., U.S. Pat. Nos. 4,857,474, and 4,520,110).

Fluorescent markers have found uses in molecular biology as labels for nucleic acid probes, antibodies, and other specific binding ligands in the detection of particular target moieties (e.g., particular nucleic acid sequences, receptors, etc.). Labeled binding molecules are used both in vitro and in vivo as diagnostic indicators and as research tools. Consequently there has been considerable interest and research on the development of fluorescent indicators.

Typically biological macromolecules (e.g., proteins or oligonucleotides) are labeled with a fluorescent marker (e.g., fluorescein, rhodamine, umbelliferone, and lanthanide chelates) either directly through a covalent linkage (e.g., a carbon linker), or indirectly whereby the macromolecule is bound to a molecule such as biotin or dioxigenin, which, is subsequently coupled to a fluorescently labeled macromolecular binding moiety (e.g., streptavidin or a labeled monoclonal antibody). Fluorescein and rhodamine are among the most commonly used fluorophore since they are readily available in an activated form for direct coupling to antigens or antibodies. Both fluorescein and rhodamines show good chemical stability and have a proven record in actual use as labels. However, macromolecules labeled with these fluorophores suffer from chemical quenching of fluorescence, and it is difficult to control the labeling of discrete sites within the macromolecule.

These fluorescent labeling systems also suffer the disadvantage that the fluorescent complexes and/or their binding moieties are relatively large, and must be prepared and supplied from an exogenous source because most organisms are not capable of synthesizing these molecules. In addition, these molecules are often toxic to the subject organism.

With only one exception, the Green Fluorescent Protein (GFP) from the jellyfish *Aequorea victoria* (U.S. Pat. No. 5,491,084), the ability to synthesize a fully functional fluorescent macromolecule has been restricted to the host organism in which the protein naturally occurs. Because the nucleic acid encoding GFP can be cloned into a cell and expressed to yield a non-fluorescent protein precursor that spontaneously assembles its own fluorophore, GFP has gained widespread utility as a selectable marker and a probe of cellular events (Cubitt et al. (1995) *Trends In Biochem. Sci.* 20, 448–455). From many attempts to improve the properties of GFP through genetic engineering, it is clear that there is a finite spectral window within which GFP is useful as a fluorescent marker. The development of additional protein-based fluorescent markers that can be functionally expressed in various cell types by standard genetic engineering techniques with an extended fluorescence wavelength range, and a variety of useful biochemical properties is desirable.

A recent development in the field of fluorescent labeling has been the use of phycobiliprotein conjugates. Phycobiliproteins are a class of highly fluorescent proteins that form a part of the light-harvesting system in the photosynthetic apparatus of bluegreen bacteria and of two groups of eukaryotic algae, red algae and the cryptomonads. A particularly useful variation of their use comprises preparation of a phycobiliprotein tandem conjugate with a large Stokes shift. An example of such a conjugate is the covalent attachment of the phycobiliproteins, phycoerythrin and allophycocyanin. The resulting tandem conjugate has a large Stokes shift with an emission maximum at 660 nm and an excitation waveband that starts at about 440 nm. However, production of such tandem complexes requires human intervention in the formation of a covalent or other chemical bond between the two components, therefore increasing the complexity of the production of the final conjugate.

Despite these advances, the art fails to provide fluorescent markers that can be easily produced and readily engineered to provide strong fluorescent signals over a wide range of wavelengths. The present invention addresses these and other needs.

SUMMARY OF THE INVENTION

This invention provides a new class of fluorescent protein adducts (phycobilin conjugates) that are generally suitable for use as fluorescent markers. Owing to their long wavelength absorption maxima, their high molar absorption coefficients and the ability of recombinant phytochrome apoproteins to spontaneously assemble with a variety of bilin chromophore precursors, the phytochromes are potentially ideal fluorescent markers.

Phytochromes perform a key role as light sensors in most photosynthetic organisms, via photoisomerization of the covalently bound phytochromobilin or phycocyanobilin prosthetic group which induces a protein conformational change and subsequent signal transduction cascade. The adduct between recombinant apophytochrome and phycoerythrobilin (PEB), the natural chromophore precursor of phycoerythrin, is highly fluorescent because it lacks the double bond required for photoisomeration. This invention demonstrates that fluorescent apophytochrome-bilin conjugates (e.g., apophytochrome-PEB adducts), which are referred to herein as the "phytofluors", are intensely fluorescent, photostable proteins useful as probes for biological research.

In a preferred embodiment, the fluorescent adducts (i.e., phytofluors) of this invention comprise a protein component (an apoprotein) and a nitrogen heterocyclic compound (e.g., a polypyrrole). In a preferred embodiment the nitrogen heterocycle is a dipyrrole, tripyrrole, tetrapyrrole, or analogues thereof, with linear tetrapyrroles and analogues thereof being most preferred. In some embodiments, higher order pyrroles and their analogues can also be used. One particularly preferred bilin is phycoerythrobilin (PEB). The apoprotein is preferably an apophytochrome or analogue thereof. Preferred analogues are recognized by and thus comprise the consensus sequence of FIG. 6. The apoprotein can be derived from vascular and non-vascular plants, green alga, bacteria or cyanobacteria, or can be chemically synthesized de novo. Thus, preferred apoproteins are encoded by plant genes, algal genes, bacterial genes, or cyanobacterial genes. Particularly preferred apoproteins include any of the apoproteins described herein or those listed in the sequence listing or conservative substitutions of these sequences, while most preferred apoproteins include apoproteins from plants (e.g., oats with an apoprotein having about 1100 amino acid residues), green algae (e.g., *Mesotaenium caldariorum*), or cyanobacteria (as illustrated in the sequence listing), or related, proteins having conservative substitutions. Truncated apoproteins consisting of a chromophore domain; the apoprotein N-terminal subsequence sufficient for lysase activity are particularly preferred. One preferred N-terminal subsequence consists of less than about 600 N-terminal amino acids, more preferably less than about 515 N-terminal amino acids, and most preferably less than about 400 N-terminal amino acids.

In one preferred embodiment, this invention provides for a moiety that is labeled with one or more of the fluorescent adducts of this invention. The fluorescent adduct is attached covalently, or non-covalently, directly, or through a linker to a moiety that is to be labeled. The moiety can be virtually any composition, including for example, a biological molecule (biomolecule), an organelle, a cell, a tissue, virtually any naturally occurring natural or synthetic material that is chemically compatible with the fluorescent adduct, and even an article of manufacture. In a particularly preferred embodiment, the fluorescent adducts of this invention are attached to biological molecules including, but not limited to proteins, carbohydrates, lipids, and nucleic acids. Particularly preferred biological molecules are members of binding pairs (binding partners) that specifically bind to a target molecule. Preferred members of binding pairs include antibodies, nucleic acids, lectins, enzymes, ligands, receptors, and the like.

The fluorescent adduct can be joined to the moiety to be labeled either by attachment to the bilin or by attachment to the apoprotein, with attachment to the apoprotein being most preferred. The apoprotein can be chemically conjugated to the subject (labeled) molecule or, where the subject moiety is a protein or contains a protein component, the apoprotein can be fused to the amino or carboxyl terminus of the protein or protein component through a peptide bond thereby forming a fusion protein. The fusion protein can also be a recombinantly expressed fusion protein. Alternatively, the apoprotein can be joined to the protein or protein component of the subject moiety through linkages between side chains (e.g., a disulfide linkage between cysteines).

This invention also provides methods of use for the above-described fluorescent adducts and for the compositions comprising a moiety joined to any of the fluorescent adducts described above or herein. Thus, for example, in one embodiment, this invention provides for a method of testing the presence of a biomolecule in a sample. The method involves providing a sample comprising a biomolecule linked to a fluorescent adduct consisting of an apoprotein and a bilin chromophore and contacting the sample with light which causes the fluorescent adduct to emit light, and detecting the emitted light thereby detecting the presence of the biomolecule. In one particularly preferred embodiment, the sample is contacted with light having a wavelength of about 570 nm. The step of detecting the emitted light may include detecting light having a wavelength of about 590 nm. In a particularly preferred embodiment, the biomolecule is one or more of any of the above-identified biomolecules.

This invention also provides methods of expressing and detecting a selectable marker. These methods include providing a nucleic acid that encodes a protein of interest and any of the apoproteins described above and herein. The expressed apoprotein is contacted with a bilin, more preferably one of the bilins described above or herein to form a fluorescent adduct. Finally, the fluorescent adduct is contacted with light which causes the fluorescent adduct to fluoresce emitting light which is then detected thereby indicating the presence of the selectable marker.

In still yet another embodiment, this invention provides a method of detecting and/or quantifying protein-protein interactions. The two subject proteins are expressed in fusion with or conjugated to an apoprotein. The apoproteins are selected such that, when combined with their respective bilins, they form a first and a second fluorescent adduct, respectively. The first adduct fluoresces at a wavelength absorbed by the second adduct which then emits at a different wavelength. Exposure of the proteins with light causes the first fluorescent adduct to emit light that is transferred to the second fluorescent adduct which then emits light at a different wavelength thereby indicating that the two proteins are in close proximity. This invention also provides for numerous other variants of this assay which are disclosed herein.

DEFINITIONS

The term "fluorescent adduct" refers to a fluorescent molecule (i.e., one capable of absorbing light of one wavelength and emitting light of a second wavelength) comprising an "apoprotein" (also referred to as an apophytochrome) component joined to a "bilin" component, both of which are described below. The fluorescent phytochrome-bilin conjugates (e.g., phytochrome-PEB adducts), are also referred to herein as "phytofluors". The manner in which the two components are joined to form an adduct is irrelevant to the present invention. Typically, the two components spontaneously form an adduct through covalent interactions. The components may also be deliberately linked through covalent bonds (e.g., through the use of crosslinking reagents). The fluorescent adducts of this invention do not require pairing of an apoprotein with its corresponding native bilin. To the contrary, the invention contemplates adducts consisting of naturally occurring or engineered apoproteins with bilins derived from different organisms, or with non-naturally occurring synthetic linear pyrroles.

The terms "apoprotein", "apophytochrome", or "apoprotein polypeptide", as used herein, refer to polypeptides derived from eukaryotes, such as vascular plants, non-vascular plants, and algae, or from prokaryotes, such as cyanobacteria. The term encompasses both naturally occurring apoproteins and variant polypeptides derived through mutagenesis. The apoproteins have a hydrophobic pocket, referred to as chromophore binding site, capable of forming an adduct with a bilin component. The apoproteins of the invention are typically homodimeric proteins about 1100 amino acids in length, each subunit being composed of two major domains. The globular 70 kD N-terminal domain contains the hydrophobic pocket, while the more elongated 55 kD carboxyl terminal domain contains the sites at which the two subunits are associated. Apophytochromes can be readily identified by one of skill in the art by comparison of the polypeptide sequence in question with the apophytochrome consensus sequence provided in FIG. 6 using standard sequence comparison methodologies. For a general discussion of apoprotein structure and function, see, Quail et al. (1997) in *Plant Cell and Environment*, 20: 657–665.

The "bilin" components of the adducts of the invention are linear polypyrroles (e.g., di-, tri-, or tetrapyrroles) capable of fluorescing when associated with an apoprotein. Typically, the bilin components of the invention are isolated from vascular plants, algae, or cyanobacteria according to standard techniques. The bilin components can also be synthesized de novo. For a general discussion of bilins useful in the present invention see, Falk (1989) Pp.355–399 in: *The Chemistry of Linear Oligopyrroles and Bile Pigments*. pp 355–399. Springer-Verlag, Vienna.

The term "chromophore domain" or "minimal chromophore domain" refers to the apoprotein N-terminal subsequence sufficient for lyase activity; the ability to spontaneously assemble in the presence of a bilin to form a phytofluor. Chromophore domains typically comprise less than 600 amino acids of the N terminus of the apoprotein, preferably less than about 515 amino acids, more preferably less than about 450 amino acids and most preferably less than about 400, 390, or even 350 N-terminal amino acids. One preferred chromophore domain comprises the 514 N-terminal amino acids of a cyanobacterial phytochrome.

The phrase "nucleic acid" refers to a single or double-stranded polymer of deoxyribonucleotide or ribonucleotide bases read from the 5' to the 3' end. It includes cDNA, self-replicating plasmids, infectious polymers of DNA or RNA and non-functional DNA or RNA.

The term "subsequence" when referring to a nucleic acid refers to a nucleic acid sequence that comprises a part of a longer sequence of a nucleic acid, and when referring to a peptide refers to an amino acid sequence that comprises part of a longer sequence of a peptide, polypeptide or protein.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms such as CLUSTALW, GAP, BESTFIT, BLAST, FASTA, and TFASTA (Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BLAST) using standard parameters. In one embodiment, 25% sequence identity over a window of 200 amino acids coupled with information regarding the apophytochrome consensus sequence is sufficient to identify a new apophytochrome. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two nucleic acid molecules hybridize to each other, or to a third nucleic acid, under stringent conditions. Stringent conditions are sequence dependent and will be different in different circumstances. Generally, stringent conditions are selected to be about 5 C. lower than the thermal melting point ($T_m$) for the specific sequence at a defined ionic strength and pH. The $T_m$ is the temperature (under defined ionic strength and pH) at which 50% of the target sequence hybridizes to a perfectly matched complementary nucleic acid sequence. Typically, stringent conditions will be those in which the salt concentration is about 0.02 molar at pH 7 and the temperature is at least about 60 C. Stringent conditions for a standard Southern hybridization will include at least one wash (usually 2) in 0.2× SSC at a temperature of at least about 50 C., usually about 55 C., for 20 minutes, or equivalent conditions.

The term conservative substitution is used herein to refer to replacement of amino acids in a protein with different amino acids that do not substantially change the functional properties of the protein. Thus, for example, a polar amino acid might be substituted for a polar amino acid, a non-polar amino acid for a non-polar amino acid, and so forth. The following six groups each contain amino acids that are conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W).

A biological "binding partner" or a member of a binding pair refers to molecules that specifically bind other molecules to form a binding complex such as antibody-antigen, lectin-carbohydrate, nucleic acid-nucleic acid, biotin-avidin, etc.

The term "specifically binds", as used herein, when referring to a biomolecule (e.g., protein, nucleic acid, antibody, etc.), refers to a binding reaction which is determinative of the presence of a specific biomolecule within a heterogeneous population of proteins and/or other biologics. Thus, under designated conditions (e.g. immunoassay conditions in the case of an antibody), the specified ligand or antibody binds to its particular "target" biomolecule (e.g. a receptor protein) and does not bind in a significant amount to other proteins or other biomolecules present in the sample, or to other proteins or other biomolecules with which the ligand or antibody may come in contact in an organism.

The term "antibody", as used herein, includes various forms of modified or altered antibodies. Such forms include, but are not limited to, an intact immunoglobulin, an Fv fragment containing only the light and heavy chain variable regions, an Fv fragment linked by a disulfide bond (Brinkmann, et al. (1993) Proc. Natl. Acad. Sci. USA, 90: 547–551), an Fab or (Fab)'₂ fragment containing the variable regions and parts of the constant regions, a single-chain antibody and the like (Bird et al (1988) Science 242: 424–426; Huston et al. (1988) Proc. Nat. Acad. Sci. USA 85: 5879–5883). The antibody may be of animal (especially hamster, mouse, rat, rabbit, pig, or goat) or human origin or may be chimeric (Morrison et al., Proc Nat. Acad. Sci. USA 81: 6851–6855 (1984)) or humanized (Jones et al. (1986) Nature 321: 522–525, and published UK patent application No: 8707252). Methods of producing antibodies suitable for use in the present invention are well known to those skilled in the art and can be found described in such publications as Harlow & Lane, Antibodies: A Laboratory Manual, Cold Spring Harbor Laboratory (1988), and Asai, Methods in Cell Biology Vol. 37: Antibodies in Cell Biology, Academic Press, Inc. N.Y. (1993).

BRIEF DESCRIPTION OF THE DRAWINGS

FIG. 1 shows the structure of three bilins useful in the present invention, phytochromobilin (PΦB), phycocyanobilin (PCB), and phycoerythrobilin (PEB) as bound to the conserved cysteine residue in apophytochrome.

FIG. 6 shows the phytochrome consensus sequence (SEQ ID NO: 1). Shaded residues are residues totally conserved in all known phytochromes including vascular and non-vascular plants, cyanobacteria, and algae. Upper-case letters indicate residues conserved in all phytochromes and in rcaE, a putative phytochrome regulator of chromatic adaptation in cyanobacteria (Kehoe et al. (1996) *Science*, 273: 1409–1412). Definitions: Asphya, *Avena sativa* phyA; AtphyA, Arabidopsis phyA (SEQ ID NO: 2); AtphyA, Arabidopsis phyA (SEQ ID NO: 3), Mcphylb, *Mesotaenium caldariorum* phylb (green alga) (SEQ ID NO: 4), S6803 phy1; Synechocystis sp 6803 phy1 (a cyanobacterium) (SEQ ID NO: 5).

FIGS. 9A–D. Phytofluor fluorescence in Arabidopsis plant seedlings. Dark grown hy1 (A and B), wild type (C), and hy1 phyA phyB (D) seedlings were incubated with PEB and imaged by confocal microscopy with 10× (A, C, D) and 40× (B) magnification as described in the Examples. Phytofluor fluorescence emission only (590–610 nm) is shown on the left, while chlorophyll fluorescence emission (670–800 nm) is shown on the right.

FIGS. 10A–C illustrate a phytochrome operon of Synechocystis sp PCC6803. (A) Genomic organization of the phytochrome-related gene cph1 (locus slr0473; GB:D64001, locus 1001165) and the adjacent small response regulator gene rcp1 (locus slr0474; GB:D64001, locus 1001166). (B) Deduced amino acid sequence of Cph1 (SEQ ID NO: 6). Highlighted residues are 100% conserved between Cph1 and 21 full length eukaryotic phytochrome sequences in the nonredundant GenEMBL databases. The conserved cysteine for bilin attachment for eukaryotic phytochromes is shown with a black box. Underlined protein sequences represent the five conserved motifs of transmitter modules (Parkinson and Kofoid (1992) *Annu. Rev. Genet.* 26: 71–112). The outlined H represents the conserved histidine "autophosphorylation" site. (C) Multiple sequence alignment of Rcp1 (SEQ ID NO: 7) and the response regulators, RcaF (SEQ ID NO: 8) (Kehoe and Grossman (1997) J. Bacteriol.179, 3914–3921), CheY (SEQ ID NO: 9) (Mutoh and Simon (1986) *J. Bacteriol.*, 165: 161–666) and SpoOF (Perego et al. (1994) *Cell* 79: 1047–1055). Invariant aspartate, threonine and lysine residues of the CheY superfamily are boxed, and conserved residues are highlighted.

FIGS. 11A–D illustrate the spectroscopic and biochemical properties of bilin adducts of recombinant Cph1. (A) Phytochrome difference spectra of 40% ammonium sulfate-fractionated, Cph1-containing protein (ASP) extracts (Li and Lagarias (1992) *J. Biol. Chem.* 267: 19204–19210) following incubation with PΦB (short dashes), PCB (solid line) or PEB (long dashes). (B) Visualization of PΦB-, PCB- and PEB-adducts of Cph1 and N514 mutant on PVDF membranes treated with zinc acetate or alkaline phosphatase conjugated to streptavidin. Molecular mass markers at 119, 83, and 47 kDa are indicated with dots. (C) A structural model for prototypical eukaryotic and Synechocystis phytochromes. Both phytochromes share a similarly sized photosensory domain (open rectangle) containing a conserved cysteine chromophore binding site (*) and a C-terminal transmitter-related module (dark shaded rectangle). Prototypical phytochromes also contain a small N-terminal extension and a second transmitter-related module (light shaded rectangle) that contains the PAS A and B repeats (Lagarias et al. (1995) *Plant Mol. Biol.* 29, 1127–1142). (D) Dark reversion of PCB- and PΦB-adducts of full length Cph1 (J and E, respectively) and N514 mutant (H and C, respectively) (Litts et al. (1983) *J. Biol. Chem.* 258: 11025–11031).

DETAILED DESCRIPTION

Figure 2:
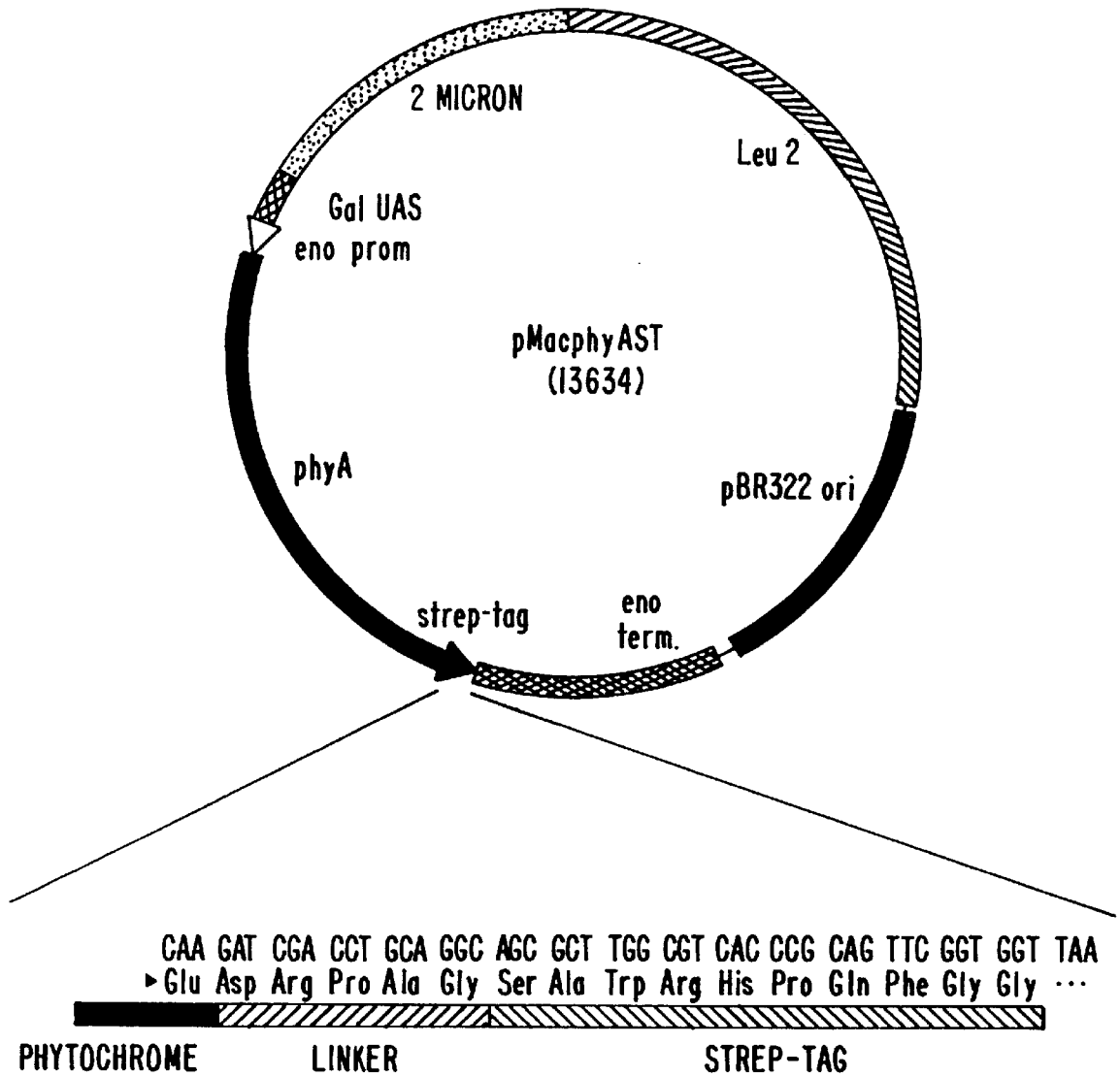
FIG. 2 shows a schematic diagram of the pMacphyAST plasmid used for expression of Strep Tagged Phytochrome ASPHYAST in the yeast S. cerevisiae. The plasmid is composed of 13634 base pairs. Salient features of the plasmid are indicated: 2 micron is the yeast origin of replication, Leu2" allows rescue of leucine deficient auxotrophs, pBR322" is the origin of replication for E. coli, eno term. is the enolase transcription terminator, phytochrome cDNA (phyA) and Strep Tag are indicated, eno prom. is the enolase promoter, and Gal UAS is the upstream activating sequence of the galactose inducible promoter. The expanded region shows the protein sequence of the APHYSAST carboxy terminus from the last phytochrome amino acid (gln), through the 5 amino acid linker to the 10 amino acid Strep-Tag peptide.

This invention is directed to fluorescent adducts, referred to herein as phytofluors, and their use as fluorescent markers or labels in a variety of contexts. The phytofluors comprise an apoprotein component (e.g. an oat or cyanobacterial apophytochrome) joined to a bilin component (e.g., phycoerythrobilin (PEB)). The phytofluors (fluorescent adducts) may be chemically conjugated or fused (i.e. recombinantly expressed as a fusion protein) to a subject moiety that is to be so labeled. In a preferred embodiment the labeled moiety is a member of a biological binding pair for use in any known or later discovered technique involving fluorescent labeling of analytes or other moieties.

The apoproteins and bilins forming the fluorescent phytofluors of this invention are available from natural sources or can be modified to provide novel complexes having different absorbance, emission, or labeling characteristics. These compositions find use for labeling of virtually any molecule or material that is chemically compatible with the fluorescent adducts. The phytofluors are well suited for labeling biological molecules and are particularly used to label a biochemical binding-pair member so that the resulting conjugates or fusions can be used in assays involving non-covalent binding to the complementary member of the specific binding pair. A wide variety of methods involve competitive or non-competitive binding of ligand to receptor for detection, analysis, or measurement of the presence of ligand or receptor.

Thus, for example, in one embodiment, this invention provides for antibodies or antibody fragments to which the fluorescent adducts (phytofluors) of this invention are joined (either covalently or non-covalently). The antibodies are capable of specifically binding to the antigen to which they are directed. Detection of the presence, absence, or amount of fluorescence of the antibody-bound fluorescent adduct of this invention provides an indication of presence, absence, or amount of analyte to which the antibody is directed.

Similarly phytofluor labeled antibodies, or other ligands, can be used in immunohistochemical applications. In this context, fluorescent adduct labeled antibodies are used to probe cells, tissues, and sections thereof. When the subject sample is contacted with the labeled ligand, the ligand binds and localizes to specific regions of the sample in which the target molecule (the molecule or moiety recognized by the ligand) is located. Localization and/or quantification of the fluorescent signal produced by the attached phytofluor provides information concerning the location and/or quantity of the target molecule in the sample. One of skill in the art will appreciate that the phytofluors of this invention are also well suited for in situ and in vivo labeling of molecules, cells, and cellular components.

The phytofluor labels of this invention can be attached to a wide variety of biological molecules in addition to antibodies. This may include proteins, in particular proteins recognized by particular antibodies, receptors, enzymes, or other ligands, nucleic acids (e.g., single or double stranded DNA, cDNA, mRNA, cRNA, rRNA, tRNA, etc.) various sugars and polysaccharides, lectins, enzymes, and the like. Uses of the various labeled biomolecules will be readily apparent to one of skill in the art. Thus, for example, labeled nucleic acids can be used as probes to specifically detect and/or quantify the presence of the complementary nucleic acid in, for example, a Southern blot.

The phytofluors of this invention can be attached to non-biological molecules and various articles of manufacture. Thus, for example where it is desired to associate an article of manufacture with a particular manufacturer, distributor, or supplier, the phytofluor, or simply one component of the phytofluor can be attached to the subject article. Later development (e.g., by addition of the second component such as bilin or apoprotein) and exposure to an appropriate light source will provide a fluorescent signal identifying the article as one from a source of such labeled articles.

In another embodiment, the phytofluors of this invention can be used for probing protein-protein interactions. In a preferred embodiment, two apoprotein cDNA constructs are used. The first construct will encode a apoprotein species whose assembly with a given bilin emits at a well defined wavelength (donor). The second construct will encode an apoprotein species whose assembly with the same, or different, bilin produces a fluorescent species that both absorbs and emits light to longer wavelengths (acceptor). Protein-protein interaction between two proteins of interest (e.g. protein X and protein Y) is identified following their co-expression as translational fusions with apoprotein in constructs 1 (donor) and 2 (acceptor) using fluorescence energy transfer from the shorter wavelength-absorbing donor species to the longer wavelength-absorbing acceptor species. In a preferred embodiment, the fluorescent phytochrome species are selected to have good spectral overlap. proximity caused by the protein-protein interaction between the translational fused proteins X and Y will then permit fluorescence energy transfer thereby providing an indication of proximity between protein X and protein Y. This application can utilize the uptake of exogenous bilin pigment into living cells, or alternatively, may use endogenously expressed bilins in various organisms and cell types.

In a specific application, a yeast or $E.$ $coli$ strain containing donor construct 1, engineered to produce a fluorescent chimeric protein bait with a known cDNA sequence, will be co-transformed, simultaneously or sequentially, with a prey cDNA library (i.e., plasmid or phage). The prey cDNA library will be constructed using acceptor construct 2 for expression of apoprotein-protein fusions which yield fluorescent tagged protein products in the presence of the correct bilin. Co-transformation events which express prey proteins in the library that interact with the expressed bait polypeptide can be identified by illuminating the shorter wavelength absorbing donor phytofluor species and viewing emission from the longer wavelength acceptor phytofluor emitting species. Actinic illumination for this screen can either be obtained with a quartz halogen projector lamp filtered through narrow bandpass filters or with a laser source and fluorescence detection of colonies using digital imaging technology (Arkin et al. (1990) $Bio$-$Technology$ 8: 746–749). Fluorescent activated cell sorting (FACS) can also be used to identify cells co-expressing interacting donor and acceptor proteins.

In another application of this invention, the apoprotein cDNA in donor construct 1 "prey" is substituted with a green fluorescent protein (GFP) cDNA or construction of GFP-tagged cDNA expression libraries. By co-expression of apoprotein-tagged bait construct (Construct 2 above) with the GFP-tagged "prey" library, proteins which interact with the bait polypeptide will be visualized by energy transfer from GFP to the phytochrome tagged bait using, for example, digital imaging technology or FACS. The ability of GFP to spontaneously assemble its fluorophore makes it unnecessary to make two apoprotein constructs which have different fluorescence properties.

In a third specific application, chimeric apoprotein-protein X cDNA (where protein X is any protein of interest) are expressed in transgenic eukaryotes (yeast, plants, Drosophila, etc.) in order to study the subcellular localization of protein X in situ. Following feeding of exogenous bilin, subcellular localization can be performed using fluorescence microscopy (e.g., laser confocal microscopy).

In one particularly preferred embodiment, the phytofluors of this invention are used as in vitro or in vivo labels in a manner analogous to the use of Green Fluorescent Protein (GFP). This typically involves transfecting a cell with a nucleic acid encoding an apoprotein in such an manner that the cell expresses the apoprotein (e.g., the nucleic acid is a component of an expression cassette). When the apoprotein is contacted with the appropriate bilin, supplied either exogenously or produced endogenously, the phytofluor (fluorescent adduct) self assembles and thereby produces a fluorescent marker.

Uses of such a marker are well known to those of skill in the art (see, e.g., U.S. Pat. No. 5,491,084 which describes uses of GFP). In one preferred embodiment, the phytofluor can be used as a marker to identify transfected cells. In the simplest approach, a nucleic acid expressing an apoprotein such as that described in Example 1 can be provided as a marker in a vector. The apoprotein, along with the cloned protein of interest, will be expressed in the transfected host. Application of the appropriate exogenous bilin will cause formation of the fluorescent adduct permitting ready detection of the transformed cell. Alternatively, the apoprotein can form an adduct with an endogenous bilin produced by the transformed organism (e.g., a plant cell). In this embodiment, the apoprotein will be a variant which forms fluorescent adduct when combined with the naturally occurring bilin.

Based on the disclosure provided herein, one of skill will readily appreciate that there are numerous other uses to which the phytofluors (fluorescent adducts) of this invention can be applied.

Preparation of apoprotein polypeptides.

Apoprotein polypeptides used in the phytofluors of this invention can be expressed recombinantly or isolated from natural sources according to standard techniques. The polypeptides or nucleic acids encoding them can be prepared from a wide range of organisms including vascular plants, algae, and cyanobacteria.

In higher plants, apoprotein polypeptides are encoded by a gene family of at least five structurally related members designated PHYA–PHYE (see, Terry et al. (1993) $Arch.$ $Biochem.$ $Biophys.$ 306:1–15 and Scharrock et al. (1989)

*Genes Dev.* 3:1745–1757). The primary structures of all apoproteins are very similar, with a polypeptide of about 1100 amino acids in length (Quail et al. in Phytochrome Properties and Biological Action (Thomas and Johnson eds.) pp13–38, (Springer-Verlag, Berlin 1991)). The native protein is a homodimer; the individual subunits being composed of two major domains. The globular 70 kD N-terminal domain contains the hydrophobic pocket in which the bilin chromophore resides (Gabriel et al.. (1993) *J. Theor. Biol.* 44:617–645. The more elongated 55 kD carboxyl terminal domain contains the sites at which the two subunits are associated (Edgerton et al. (1992) *Plant Cell* 4:161–171). This domain is also responsible for phytochrome function, although both domains are thought to participate in the signal transmission process in native phytochrome.

Phytofluor apoproteins can be isolated from natural sources, most preferably from bilin-deficient natural sources including, vascular and nonvascular plants, algae and cyanobacteria using standard protein isolation techniques well known to those of skill in the art. Generally, these methods involve standard techniques well known in the art, including selective precipitation with such substances as ammonium sulfate, column chromatography, immunopurification methods, and others. See, for instance, R. Scopes, *Protein Purification: Principles and Practice,* Springer-Verlag: New York (1982).

In preferred embodiments, the polypeptides are produced recombinantly. Standard methods for preparation of recombinant proteins can be used for this purpose. For a discussion of the general laboratory procedures required for this purpose see, Sambrook, et al., (1989) *Molecular Cloning: A Laboratory Manual* (2nd Ed.), Vol. 1–3, Cold Spring Harbor Laboratory, Cold Spring Harbor, N.Y.

Nucleic acids encoding apoprotein polypeptides can be isolated from a number of organisms according to standard techniques. Exemplary genes are those isolated from higher plants (e.g., AsphyA (SEQ ID NO: 11) and AtphyA), and the green alga *Mesotaenium caldariorum* (i.e. Mcphy1b), SEQ ID NO: 12). In addition, genes encoding apophytochrome can be obtained from cyanobacteria. It was a discovery of this invention that the cyanobacteria Synechocystis sp. produces an apophytochrome. In particular, the open reading frame listed in GenBank D64001, locus 1001165 and designated herein as S6803phy1 (SEQ ID NO: 13) was determined to be an apophytochrome by sequence alignment methods. Having identified herein that cyanobacteria produce apophytochromes, identification of other cyanobacterial apophytochromes can be accomplished using routine methods available to one of skill in the art. Sequences for these apoproteins are provided in the sequence listing below. The corresponding nucleic acid sequences are known to those of skill in the art. One of skill will recognize that these sequences can be used to determine the design primers and probes for isolation of related genes in other organisms.

Generally, recombinant expression techniques involve the construction of recombinant nucleic acids and the expression of genes in transfected cells. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology,* F. M. Ausubel et al., eds., Current Protocols, a joint venture between Greene Publishing Associates, Inc. and John Wiley & Sons, Inc., (1994 Supplement) (Ausubel).

The polypeptides are expressed in a recombinantly engineered cell such as plants, bacteria, yeast, insect (especially employing baculoviral vectors), and mammalian cells. It is expected that those of skill in the art are knowledgeable in the numerous expression systems available for expression of the DNA encoding apoprotein polypeptides. No attempt to describe in detail the various methods known for the expression of proteins in prokaryotes or eukaryotes will be made.

In brief, the expression of natural or synthetic nucleic acids encoding the polypeptides will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the binding domains. To obtain high level expression of a cloned gene, it is desirable to construct expression plasmids which contain, at the minimum, a strong promoter to direct transcription, a ribosome binding site for translational initiation, and a transcription/translation terminator.

Expression in Prokaryotes

Examples of regulatory regions suitable for this purpose in *E. coli* are the promoter and operator region of the *E. coli* tryptophan biosynthetic pathway as described by Yanofsky (1984) *J. Bacteriol.,* 158: 1018–1024 and the leftward promoter of phage lambda ($P_L$) as described by Herskowitz and Hagen (1980) *Ann. Rev. Genet.,* 14: 399–445. The inclusion of selection markers in DNA vectors transformed in *E. coli* is also useful. Examples of such markers include genes specifying resistance to ampicillin, tetracycline, or chloramphenicol. See Sambrook et al. for details concerning selection markers for use in *E. coli*.

Expression systems for expressing the polypeptides are available using *E. coli,* Bacillus sp. (Palva et al. (1983) *Gene* 22:229–235; Mosbach et al. *Nature,* 302:543–545) and Salmonella. *E. coli* systems are preferred.

The apoprotein polypeptides produced by prokaryote cells may not necessarily fold properly. During purification from *E. coli,* the expressed polypeptides may first be denatured and then renatured. This can be accomplished by solubilizing the bacterially produced proteins in a chaotropic agent such as guanidine HCl and reducing all the cysteine residues with a reducing agent such as beta-mercaptoethanol. The polypeptides are then renatured, either by slow dialysis or by gel filtration (see, e.g. U.S. Pat. No. 4,511,503).

Expression in Eukaryotes

A variety of eukaryotic expression systems such as yeast, insect cell lines and mammalian cells, are known to those of skill in the art. As explained briefly below, the apoprotein polypeptides may also be expressed in these eukaryotic systems.

Expression in Yeast

Synthesis of heterologous proteins in yeast is well known and described. *Methods in Yeast Genetics,* Sherman et al., Cold Spring Harbor Laboratory, (1982) is a well recognized work describing the various methods available to produce the polypeptides in yeast.

Preferred yeast expression systems are described in Wahleithner et al. (1991) *Proc. Natl. Acad. Sci. USA* 88:10387–10391, Murphy and Lagarias (1997) *Photochem. Photobiol.,* 65: 750–758, and Wu et al. (1996) *Proc. Natl.*

Acad. Sci., USA, 93: 8989–8994. Further examples of yeast expression are described below. A number of yeast expression plasmids like YEp6, YEp13, YEp4 can be used as vectors. A gene of interest can be fused to any of the promoters in various yeast vectors. The above-mentioned plasmids have been fully described in the literature (Botstein et al. (1979) *Gene,* 8: 17–24; Broach et al. (1979) *Gene,* 8: 121–133).

The polypeptides can be isolated from yeast by lysing the cells and applying standard protein isolation techniques to the lysates. The monitoring of the purification process can be accomplished by using spectroscopic techniques, or by using Western blot techniques or radioimmunoassays, or other standard immunoassay techniques.

Expression in Plants

The apoprotein polypeptides of this invenion can also be expressed in plants or plant tissues. Plant tissue includes differentiated and undifferentiated tissues of plants including, but not limited to, roots, shoots, leaves, pollen, seeds, tumor tissue, such as crown galls, and various forms of aggregations of plant cells in culture, such as embryos and calli. The plant tissue may be in plants, cuttings, or in organ, tissue, or cell culture.

The recombinant DNA molecule encoding the apoprotein polypeptide under the control of promoter sequences may be introduced into plant tissue by any means known to the art. The technique used for a given plant species or specific type of plant tissue depends on the known successful techniques. The various DNA constructs described above may be introduced into the genome of the desired plant by a variety of conventional techniques. For example, the DNA construct may be introduced directly into the genomic DNA of the plant cell using polyethylene glycol precipitation (Paszkowski et al. (1984) *Embo J.* 3: 2717–2722) electroporation and microinjection of plant cell protoplasts (Fromm et al. (1985) *Proc. Natl. Acad. Sci. USA* 82: 5824), or the DNA constructs can be introduced into plant tissue using ballistic methods, such as DNA particle bombardment (Klein et al. (1987) *Nature* 327: 70–73). Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker gene(s) (if present) into the plant cell DNA when the cell is infected by the bacteria. For a review of gene transfer methods for plant and cell cultures see, Fisk et al. (1993) *Scientia Horticulturae* 55: 5–36 (1993) and Potrykus (1990) *CIBA Found. Symp.* 154: 198.

*Agrobacterium tumefaciens*-meditated transformation techniques are the most commonly used techniques for transferring genes into plants. These techniques are well described in the scientific literature. See, for example Horsch et al. (1984) *Science* 233: 496–498, Fraley et al. (1983) *Proc. Natl. Acad. Sci. USA* 80: 4803, and Hooykaas (1989) *Plant Mol. Biol.* 13: 327–336, Bechtold et al. (1993). *Comptes Rendus De L Academie Des Sciences Serie Iii-Sciences De La Vie-Life Sciences* 316: 1194–1199, Valvekens et al. (1988) *Proc. Natl. Acad. Sci. USA* 85: 5536–5540.

All species which are natural plant hosts for Agrobacterium are transformable in vitro. Most dicotyledonous species can be transformed by Agrobacterium. Monocotyledonous plants, and in particular, cereals, have not previously been regarded as natural hosts to Agrobacterium. There is, however, growing evidence that monocots can be transformed by Agrobacterium. Using novel experimental approaches cereal species such as rye (de la Pena et al. (1987) *Nature* 325: 274–276), corn (Rhodes et al. (1988) *Science* 240: 204–207), and rice (Shimamoto et al., (1989) *Nature* 338: 274–276) may now be transformed.

Transformation of a number of woody plants using Agrobacterium and other methods has been described. (Shuerman et al. (1993) *Scientia Horticulturae* 55: 101–124). For instance, regeneration and transformation of apples is described in James et al. (1989) *Plant Cell Rep.* 7: 658–661. Tissue culture procedures for apple including micropropagation, (Jones (1976) *Nature* 262: 392–393; Zimmerman (1983) Pp 124–135 In *Methods in Fruit Breeding,*) and adventitious bud formation (James (1987) *Biotechnology and Genetic Engineering Reviews,* 5: 33–79) have also been described. After transformation, transformed plant cells or plants comprising the introduced DNA must be identified. A selectable and/or scorable marker gene is typically used. However, the apoproteins can be detected directly through the formation of a fluorescent adduct with a bilin. In another embodiment, the apophytochrome (apoprotein) can be modified to utilize the endogenous or modified bilins produced in plants. Transformed plant cells can be selected by growing the cells on growth medium containing the appropriate antibiotic. In some instances, the presence of opines can also be used if the plants are transformed with Agrobacterium. After selecting the transformed cells, one can confirm expression of the introduced apoprotein gene(s). Simple detection of mRNA encoded by the inserted DNA can be achieved by well known methods in the art, such as Northern blot hybridization. The inserted sequence can be identified using the polymerase chain reaction (PCR) and Southern blot hybridization, as well (see, e.g., Sambrook, supra.).

Transformed plant cells (e.g., protoplasts) which are derived by any of the above transformation techniques can be cultured to regenerate a whole plant which possesses the transformed genotype and thus expresses the desired apoprotein. Such regeneration techniques rely on manipulation of certain phytohormones in a tissue culture growth medium. Plant regeneration from cultured protoplasts is described in Evans et al. (1983) pp. 124–176 In: *Protoplasts Isolation and Culture, Handbook of Plant Cell Culture,* MacMillan Publishing Company, New York; and Binding, *Regeneration of Plants, Plant Protoplasts,* pp. 21–73; CRC Press, Boca Raton, 1985. Regeneration can also be obtained from plant callus, explants, organs, or parts thereof Such regeneration techniques are described generally in Klee et al. (1987) *Ann. Rev. of Plant Phys.* 38: 467–486.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Expression in Mammalian and Insect Cell Cultures

Illustrative of cell cultures useful for the production of the apoprotein polypeptides are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, W138, BHK, Cos-7 or MDCK cell lines.

When the host cell is of insect or mammalian origin illustrative expression control sequences are obtained from the SV-40 promoter (*Science,* 222:524–527, 1983), the CMV I.E. Promoter (*Proc. Natl. Acad. Sci.* 81:659–663, 1984) or the metallothionein promoter (*Nature* 296:39–42, 1982). The cloning vector containing the expression control sequences is cleaved using restriction enzymes and adjusted in size as necessary or desirable and ligated with DNA coding for the apoprotein polypeptides by means well known in the art.

Expression of variant apoprotein polypeptides

The nucleotide sequences used to transfect the host cells described above and used for production of recombinant binding domain polypeptides can be modified according to standard techniques to yield polypeptides with a variety of desired properties. The binding domain polypeptides of the present invention can be readily designed and manufactured utilizing various recombinant DNA techniques well known to those skilled in the art. For example, the binding domain polypeptides can vary from the naturally-occurring sequence at the primary structure level by amino acid insertions, substitutions, deletions, and the like. These modifications can be used in a number of combinations to produce the final modified protein chain.

The amino acid sequence variants can be prepared with various objectives in mind, including facilitating purification and preparation of the recombinant polypeptide, biological stability, and/or fluorescence quantum yields of the adducts of the invention.

In general, modifications of the sequences encoding the apoprotein polypeptides may be readily accomplished by a variety of well-known techniques, such as site-directed mutagenesis (see, Giliman and Smith (1979) *Gene* 8:81–97 and Roberts et al. (1987) *Nature* 328:731–734), or chemical modification (Glazer et al. (1975) Pp, 205 in *Chemical Modification of Proteins*, Elsevier, N.Y.).

One of ordinary skill will appreciate that the effect of many mutations is difficult to predict. Thus, most modifications are evaluated by routine screening in a suitable assay for the desired characteristic. A particularly useful assay using expression in the yeast, *Pichia pastoris* is described below and in the examples. For instance, this assay can be used to test random genetic approaches to identify 'gain-of-function' mutations which affect the spectroscopic properties of phytochrome.

Fluorescence-based screens of the phytochrome mutant expressing cell population are particularly useful in the Pichia system because these cells synthesize PΦB (Wu et al (1996) *Proc. Natl. Acad. Sci. USA*, 93: 8989–8994). In this way, mutations affecting the primary photochemical step in the conversion of Pr to Pfr (i.e. 15Z to 15E photoisomerization) will exhibit enhanced fluorescence. Fluorescence-activated cell sorting (FACS) is particularly useful in this assay. The introduction of a bulky amino acid side chain near the D-ring of the chromophore is one example of the type of mutation which can be isolated by this screen.

Specific amino acid residues important to chromophore-protein interactions in phytochrome can be identified. For instance, epitope-tagged versions of recombinant phytochromes derived from higher plants (i.e. AsphyA-ST and AtphyA-ST), the green alga *Mesotaenium caldariorum* (i.e. Mcphy1b-ST) and the cyanobacterium Synechocystis sp. PCC6803 (i.e. S6803phy1-ST)—all four of which have been successfully expressed and assembled with bilins can be used to identify useful variants.

Phytochromes can be used in these methods. The HPLC analyses are greatly simplified by the use of a chromophore domain fragment. The expression and purification of such mutants of AsphyA or Mcphy1b is based on chromophore domain mutant expression studies of other species (see, e.g., Deforce et al. (1991) *Proc Natl Acad Sci USA* 88:10392–10396 and Schmidt et al. (1996) *J. Photochem. Photobiol., B: Biology* 34: 73–77.

In one embodiment, a preferred apoprotein consists of the chromophore domain; the N terminus of the apoprotein sufficient for lyase activity. In a particularly preferred embodiment, the apoprotein consists of the minimal chromophore domain. Such minimal domains are readily determined by performing apoprotein truncations and assaying the ability of the aproprotein to reassemble with an added bilin as described herein. One such shortened apoprotein is N514, described in the Examples.

Particular amino acid sites can also be modified. One such site is the chromophore binding site cysteine residue (i.e. $cys_{322}$ of AsphyA or $cys_{324}$ of Mcphy1b). These residues can be modified with a sulfhydryl-specific bifunctional photoaffnity crosslinking reagent such as p-azidophenacyl bromide or N(4-azidophenylthio)phthalimide (APTP). The bifunctional photoaffinity crosslinking reagent will be introduced into the molecule via reaction with $cys_{322}$ followed by UV crosslinking. Having identified putative chromophore binding site residues with this approach, saturation site-specific mutagenesis experiments will be undertaken to evaluate the importance of these residues to bilin attachment, photoactivity and/or holoprotein conformation. Control experiments to determine whether chemical modification grossly alters the apoprotein's conformation will also be performed with each sulfhydryl reagent.

Based on multiple sequence alignment of the chromophore domains of phytochromes directed mutagenesis can be carried out. In one embodiment, a "chemical rescue" approach can be employed to help distinguish specific local effects from gross structural perturbations caused by individual mutations (see, Toney et al. (1989) *Science* 243:1485–1488). Using this technique, site-directed mutations at conserved arg and trp residues can be introduced within the chromophore domain of phytochrome. $Arg_{237}$ of AsphyA is an example of a good target for mutagenesis because it is the only conserved arg residue in the chromophore domain, and thus is a potential candidate for tethering the propionic acid side chains of the bilin chromophore.

A similar approach is used to examine the importance of conserved tryptophan residues, beginning with the two universally invariant $trp_{366}$ and $trp_{475}$ of AsphyA. In this case, chemical rescue will employ indole prosthesis. The potential importance of trp residues to the phytochrome photocycle has already been implicated by resonance Raman spectroscopy (see, e.g., Mizutani et al. (1991) Biochemistry 30:10693–10700).

Other cysteine residues in the chromophore domain can also be mutagenized. First, there are relatively few cysteine residues in phytochrome with as few as 6 cysteines in the chromophore domain of S6803phy1. In addition, aside from the site of chromophore attachment, only one other cysteine (i.e. $cys_{387}$ on AsphyA) is found on almost all of the known phytochromes, the notable exception being rcaE. This suggests that most, if not all of the cysteines are dispensable, and could be substituted with isosteric serine residues without any significant structural or functional effect. For instance, the five cysteine residues in the chromophore domain of S6803phy1 can be substituted with serine residues. The photochemical properties of these mutant constructs can be examined to ascertain if the absorption coefficient, photoequilibrium and/or photochemical quantum yields are altered by mutagenesis. Another preferred embodiment is a cysteine-deficient (except for $cys_{259}$ of S6803phy1), photoactive phytochrome mutant. This mutant is particularly useful for structural studies such as crosslinking experiments proposed above. Moreover, re-introduction of cysteine residues at selected positions in this cysteine-deficient mutant can be used for structural analyses, and for specific cross-linking to other macromolecules.

Preparation of bilins

The bilin component of the adducts of the invention can be isolated from the appropriate natural source or synthesized according to techniques known in the art. Methods for synthesis of the dimethyl ester of phytochromobilin are described for instance in Weller et al. (1980) *Chem. Ber.* 113:1603–1611. Conversion of the dimethyl ester to the free acid can be accomplished according to known techniques (see, e.g., Greene and Wuts, *Protective Groups in Organic Synthesis* 2d ed. (John Wiley and Sons, 1991).

Methods for isolating bilins including phytochromobilin, phycocyanobilin (PCB), and phycoerythrobilin (PEB) from natural sources are also described in the art. For instance crude phycocyanobilin can be prepared from *Spirulina platensis* as described by Terry et al. (1993) *J. Biol. Chem.* 268:26099–26106. Crude phytochromobilin and PEB can be prepared by methanolysis of *Porphyridium cruentum* cells as described by Cornejo et al. (1992) *J. Biol. Chem.* 267: 14790–14798. The structures of phytochromobilin, PCB, and PEB are shown in FIG. 1.

Attachment of fluorescent adducts to subject molecules.
Tagged moiety.

The conjugates of the subject invention are fluorescent adducts bound either covalently or non-covalently, normally covalently, to a particular moiety to be detected. Virtually any moiety to which it is desired to attach a fluorescent label is suitable. The moiety can be a macroscopic article such as an article of manufacture that is to be fluorescently tagged, or alternatively, the moiety can be microscopic, such as cell, an organelle, or a single molecule.

Again, virtually any molecule can be tagged. Typically, however, the moiety to be tagged and detected will be a biomolecule such as a polypeptide, oligopeptide, nucleic acid, polysaccharide, oligosaccharide, lipid, and the like. For instance, the subject molecule may be a ligand or receptor. A "ligand", as used herein, refers generally to all molecules capable of reacting with or otherwise recognizing or binding to a second biological macromolecule e.g., a receptor, antigen, or other molecule on a target cell. Specifically, examples of ligands include, but are not limited to antibodies, lymphokines, cytokines, receptor proteins (e.g., CD4, CD8), solubilized receptor proteins (e.g. solubilized T-cell receptor, soluble CD4), hormones, growth factors, and the like which specifically bind particular target cells. A "growth factor" as used herein refers to a protein ligand that stimulates cell division or differentiation or inhibits cell division or stimulates or inhibits a biological response like motility or secretion of proteins. Growth factors are well known to those of skill in the art and include, but are not limited to, platelet-derived growth factor (PDGF), epidermal growth factor (EGF), insulin-like growth factor (IGF), transforming growth factor β (TGF-β), fibroblast growth factors (FGF), interleukin 2 (IL2), nerve growth factor (NGF), interleukin 3 (IL3), interleukin 4 (IL4), interleukin 1 (IL 1), interleukin 6 (IL6), interleukin 7 (IL7), granulocyte/macrophage colony-stimulating factor (GM-CSF), granulocyte colony-stimulating factor (G-CSF), macrophage colony-stimulating factor (M-CSF), erythropoietin and the like. One of skill in the art recognizes that the term growth factor as used herein generally includes cytokines and colony stimulating factors.

Attachment of the phytofluor to the moiety.

The proteinaceous portions of the fluorescent adducts (phytofluors) referred to here as the apoproteins provide a wide range of functional groups for conjugation to proteinaceous and non-proteinaceous molecules. Functional groups which are present include, but are not limited to amino, thio, hydroxyl, and carboxy. In some instances, it may be desirable to introduce, delete, or modify functional groups, particularly thio groups where the apoprotein is to be conjugated to another protein.

Depending upon the nature of the molecule (e.g., member of a specific binding pair) to be conjugated to the phytofluor complex, the ratio of the two moieties will vary widely, where there may be a plurality of subject molecules to one phytofluor or apoprotein or, conversely, where there may be a plurality of phytofluors or apoproteins to one subject molecule. Of course, the molar ratio of the molecule (moiety) to be labeled to the phytofluor or apoprotein may be about 1:1. In addition, in some instances, initial intermediates are formed by covalently conjugating a small ligand to a fluorescent adduct and then forming a specific binding pair complex with the complementary receptor, where the receptor then serves as a ligand or receptor in a subsequent complex or is itself covalently attached to a ligand or receptor intended for use in a subsequent complex.

The procedure for attaching a subject molecule to the phytofluor or an apoprotein of the fluorescent adduct will vary according to the chemical structure of the agent. As indicated above, the apoproteins contain a variety of functional groups (e.g., —OH, —COOH, —SH, or —NH2) groups, which are available for reaction with a suitable functional group on an agent molecule to bind the agent thereto. Alternatively, the apoprotein may be derivatized to expose or attach additional reactive functional groups. The derivatization may involve attachment of any of a number of linker molecules such as those available from Pierce Chemical Company, Rockford Ill. A bifunctional linker having one functional group reactive with a group on a particular agent, and another group reactive with an antibody, may be used to form the desired immunoconjugate.

Alternatively, derivatization may involve chemical treatment of the antibody; e.g., glycol cleavage of the sugar moiety of the glycoprotein antibody with periodate to generate free aldehyde groups. The free aldehyde groups on the antibody may be reacted with free amine or hydrazine groups on an agent to bind the agent thereto (see, e.g. U.S. Pat. No. 4,671,958). Procedures for generation of free sulfhydryl groups on antibodies or antibody fragments are also known (see, e.g., U.S. Pat. No. 4,659,839). Many procedure and linker molecules for attachment of various compounds including radionuclide met al chelates, toxins and drugs to proteins (e.g., to antibodies) are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071–4075).

Linking agents suitable for joining the adducts of this invention to nucleic acids are also well known. For example, linking agents which are specific to the free secondary hydroxyl normally present at the 3' end include phosphites, succinic anhydride and phthalamide. Linking agents which are specific to the phosphate normally present on the sugar at the 5' end (at least for most naturally occurring polynucleotides or products of most cleavage reactions) include carbodiimides such as 1-ethyl-,3'dimethylamino propylcarbodiimide, with or without imidazole or 1-methylimidazole. See Chu et al. (1983) *Nucleic Acids Res.* 11: 6513–6529.

EXAMPLES

The following examples are offered to illustrate, but not to limit the present invention.

EXAMPLE 1

High Efficiency Purification and Properties of Recombinant Epitope-Tagged Oat Phytochrome A Although recombinant systems provide powerful tools for molecular analysis of phytochrome, purification of the recombinant protein is desirable for proper assessment of the structural basis of various phytochrome functions. Purification facilitates assessment of the structural integrity of modified recombinant phytochromes, minimizing misidentification of catalytic function for residues which play a structural role in the protein. Expression of PHYA in heterologous organisms inherently separates phytochrome away from plant cofactors and competing enzymatic activities. Therefore, isolation of recombinant phyA from the host expression organism may provide a level of purity not possible from plants. Plant derived preparations of phyA most likely contain other phytochromes in addition to potential phytochrome associated molecules (Elich & Chory (1994) *Plant Molecular Biology*, 26: 1315–1327). These impurities may hinder formation of crystals required for high resolution X-ray analysis, and may complicate in vitro analysis of potential phytochrome biochemical activities. In addition recombinant apoprotein and/or non-natural chromophore adducts may crystallize more readily than the native photoreceptor.

This example provides a method for the efficient purification of recombinant oat PHYA from *Saccharomyces cerevisiae* using a C-terminal epitope tag. Full length oat phyA containing the 10 amino acid "strep-tag" can be expressed and purified to apparent homogeneity by its high affinity for streptavidin (Skerra, A. (1994) *Gene* 141: 79–84). The ability to purify epitope tagged phytochrome allows assessment of the integrity of the recombinant molecule with respect to phyA purified from oats.

Materials and Methods

Reagents and Enzymes.

The pASK75, Strep-tag vector was purchased from Biometra (Tampa, Fla.). DNA modifying enzymes were purchased from Gibco BRL (Grand Island, N.Y.) except for DNA ligase which was purchased from Takara/Pan Vera (Madison Wis., USA). All enzymes were used according to manufacturer's instructions. Streptavidin agarose was purchased from Sigma (St. Louis, Mo., USA).

Construction of Plasmids.

ASPHYA-HPT plasmid was obtained by mutagenesis of the stop codon of the oat phytochrome A cDNA, from the vector pGphyA3 (Wahleithner et al. (1991) *Proc. Natl. Acad. Sci. USA*, 88: 10387–10391), to produce a BglII restriction site. The modified pASK75 vector, pASK75B, was constructed by restriction of pASK75 with HindIII, ligation of the Hind2Bgl oligomer (5'-AGCTTCAGATCTGA-3' SEQ ID NO: 14)), restriction with BglII, and religation. The cDNA encoding oat phytochrome A3 (Hershey, et al. (1987) *Gene* 61: 339–348) was prepared by restriction of ASPHYA-HPT with BglII, partial fill in of the recessed 3' termini with Klenow fragment in the presence of GTP and ATP, restriction with BamHI, and agarose gel purification using the Geneclean kit from Bio 101 (Vista, Calif.).

This phyA fragment was ligated into the pASK75B vector which was prepared by restriction with SalI, partial fill in of the recessed 3' termini with Klenow fragment in the presence of CTP and TTP, and restriction with BamHI to produce plasmid pASKphyAL. The yeast expression vector, pMACPHYA-ST, was constructed by restriction of pASK-phyAL with BamHI and BglII, separation of the oat PHYA-ST cDNA fragment by agarose gel electrophoresis/geneclean, and ligation of this fragment with the pMAC106 vector (Wahleithner et al. (1991) supra.) which had been linearized with BamHI.

Expression of strep-tagged oat phytochromeA.

Strep-tagged oat phytochromeA (PHYA-ST) was expressed from the pMacphyAST plasmid in *Saccharomyces cerevisiae* strain 29A (MATa, leu2–3, leu2–112, his3–1, ade1–101, trp1–289) (Wahleithner et al. (1991) supra.). All cultures were incubated at 30° C. with shaking at 300 rpm. A few colonies were transferred from petri plates to 15 ml SD (2% dextrose, and 0.67% yeast nitrogen base without amino acids), which was supplemented with adenine, histidine, and tryptophan (at 40 mg/ml each( and grown overnight to $OD_{580}>1.0$. These precultures were used to inoculate 1 liter SR media (2% raffinose, and 0.67% yeast nitrogen base without amino acids) which was supplemented with adenine, histidine, and tryptophan (at 40 mg/ml each) in 2.8 L Fernback flasks. After incubation for 12–16 h to $OD_{580}=1.0$, ASPHYAST expression was induced by dilution of two 1 L cultures with an equal volume of SR +his+trp+ade, transfer of 1 L cell suspension to four Fernback flasks, and addition of sterile galactose to a final concentration of 1% (w/v). Induction was allowed to proceed for 24–30 hours.

ASPHYA-ST purification.

Four L of cell culture was harvested by centrifugation for 5 minutes at 5000×g. This and all subsequent steps were carried out at 4° C. The pellet was resuspended in 500 ml Milli Q water and recentrifuged as above. The washed pellet was resuspended in YH buffer (50 mM Tris HCl pH 8.0, 100 mM NaCl, 1 mM EDTA, 1 mM EGTA, 1 mM DTT, 1% DMSO, 1.5 mg/ml leupeptin, 3 mg/ml pepstatin A, 1 mM benzamidine, 1 mM PMSF) at a ratio of 1 ml per 1 g fresh cell weight. This suspension was frozen by slowly dripping into liquid nitrogen. This cell suspension was thawed, transferred to an 80 ml bead mill chamber (Biospec products; Bartlesville, Okla.), which was half filled with 0.5 mm glass beads, and the remaining volume was filled with YH buffer. Cells were lysed using 3×30 s pulses with chilling on ice for 60 s between pulses. The homogenate was clarified by centrifugation for 30 min at 100,000×g and the resulting soluble extract was transferred to a polypropylene bottle. Solid $(NH_4)_2SO_4$ was added at a ratio of 0.23 g/ml. After incubation for 16 hour on ice the protein precipitate was collected by centrifugation for 20 min at 17,000×g, dissolved in 10–15 ml buffer W (100 mM Tris HCl pH 8.0, 1 mM EDTA, 1 mM DTT), and clarified by centrifugation for 15 min at 38,000×g. The resulting ASPI fraction was incubated with 40 mg/ml avidin (Sigma, cat # A9275) to bind biotinylated proteins in the extract for at least 20 min. During this blocking step, bilins were added to initiate phytochrome assembly (see "Holophytochrome assembly and photoassay" below). ASPI fractions were then passed over a streptavidin agarose column. The column bed volume was adjusted according to the quantity of phytochrome in the ASPI such that the empirically determined capacity of 200 mg ASPHYA-ST per ml of streptavidin agarose was not exceeded. After washing with 10 volumes of buffer W, ASPHYA-ST was eluted in 1 ml fractions of buffer E (100 mM Tris HCl pH 8.0, 1 mM EDTA, 1 mM DTT, and 3 mM diaminobiotin). Phytochrome containing fractions were concentrated to 100 ml volume by centrifugation for 120 min at 3000×g with an Amicon centriplus 100 concentrator (Beverly, Mass.). Concentrated phytochrome fractions were diluted in 1 ml TEGE buffer (25 mM Tris-HCl pH 8.0, 25% ethylene glycol, 1 mM EDTA, 1 mM DTT) and stored at −80° C. until further analysis.

Bilin Preparations.

PCB was prepared from lyophilized *Spirulina platensis* (Sigma, cat# S9134) as described previously (Terry et al. (1993) *J. Biol. Chem.*, 268: 26099–26106). PΦB and PEB were prepared by methanolysis of acetone treated *Porphyridium cruentum* cells (Cornejo et al. (1992) *J. Biol. Chem.* 267: 14790–14798). All three bilins were purified by HPLC, and quantitated as described previously (Li et al. (1995) *Biochem.* 34: 7923–7930).

Holophytochrome assembly and photoassay.

The following procedures were carried out under green safelight essentially as described previously (Li and Lagarias (1992) *J. Biol. Chem.* 267: 19204–19210). Assembly with PΦB or PCB was performed by incubation of the ASPI protein fraction with 2 mM bilin for 40 min at room temperature. Assembly with PEB occurred using similar conditions except that bilin was adjusted to 5 mM final concentration. Assembled ASPI fractions were added directly to a 0.5 ml glass cuvette and absorbance difference assay was performed with an HP8450A UV-visible spectrophotometer. Purified phytochromes were assayed using 1 ml quartz cuvettes. Difference spectra of ASPHY(PΦB)-ST were obtained as described previously (Litts et al. (1983) *J. Biol. Chem.* 258: 11025–11031) and difference spectra for PHY(PCB)-ST utilized a 650±11 nm bandpass filter for red actinic illumination (Elich and Lagarias (1989) *J. Biol. Chem.* 264: 12902–12908).

SDS-PAGE, Zinc-Blot, and Western blot analysis.

SDS-polyacrylamide gel electrophoresis was performed using 10% acrylamide gels cast in 1 mm thick minigels (Bio-Rad; Hercules, Calif.) and the Laemmli buffer system (Laemmli (1970) *Nature* 227: 680–685). Following electrophoresis, gels were either stained with Brilliant Blue R-250 or proteins were transblotted to Immobilon P polyvinylidene difluoride (PVDF) membranes (Millipore; Bedford, Mass.; cat# IPVH10) at 100 V for 60 min. The same PVDF membrane was used for zinc-blot, and western blot analysis. Western blots were probed with streptavidin-alkaline phosphatase conjugate (Amersham; Arlington Heights, Ill.; cat# RPN1234), after preblocking the membrane with bovine serum albumin and avidin (Schmidt & Skerra (1993) *Prot. Eng.* 6: 109–122). Zinc blot detection was performed as described previously (Li and Lagarias (1992) supra.). Molecular weight standards for Coomassie stained gels were obtained from Sigma (cat# SDS-6H) with $M_r$ values of 29, 45, 66, 97.4, 116, and 205 kDa. Molecular weight standards for blots were obtained from Bio-Rad (cat# 161-0309) with $M_r$ values of 48, 87, 120, and 199 kDa.

SEC-HPLC analysis of ASPHYA-ST

All SEC-HPLC separations were performed using a Dionex BioLC gradient pump equipped with a Dionex variable wavelength detector interfaced to a Hewlet Packard UV-Visible chemstation. Two 0.46×25 cm hydropore SEC columns (Rainin; Emeryville, Calif.; cat#83-S03-C5) were connected directly in series and maintained at ambient temperature (25° C.). The mobile phase buffer (50 mM Tris-HCl, 100 mM $(NH_4)_2SO_4$, 25% (v/v) ethylene glycol, 0.1 mM EDTA, 0.5 mM DTT, pH 7.8) was prefiltered through a 0.4 mM HA filter (Millipore, cat# HATF047X). Between 0.04 and 0.05 $A_{280}$ units of phytochrome samples in TEGE buffer were loaded per injection. Column calibration utilized Biorad gel filtration standards (cat# 151-1901) containing bovine thyroglobulin, 670 kDa; bovine gamma globulin, 158 kDa; chicken ovalbumin, 44 kDa; horse myoglobin, 17 kDa; and vitamin B12, 1.35 kDa. Cow pea mosaic virus (>1000 kDa) was used for void volume calibration.

Fluorescence spectroscopy.

Fluorescence excitation and emission spectra were obtained with a SLM Aminco Bowman AB2 fluorimeter equipped with a continuous wave Xenon lamp. Samples in polystyrene cuvettes (Fisher, Pittsburgh, Pa.; cat# 14385991F) were excited through the 1 cm path length direction. For emission scans the excitation was set at 535 nm. For excitation scans, fluorescence emission was monitored at 610 nm. Both monochrometers were adjusted to 2 nm bandpass for all measurements.

Protein assays.

Prior to protein assay, thiol reducing agents were removed from all phytochrome samples by extraction with chloroform/methanol (Wessel and Flugge (1984) *Analyt. Biochem.* 138: 141–143), speed vac lyophilization, and resuspension in 50 mM Tris HCl pH 6.8, 1% SDS. Protein concentrations were determined using the BCA protein assay (Pierce; Rockford, Ill.) with BSA as standard (Smith et al. (1985) *Analyt. Biochem.* 150: 76–85).

Results and Discussion

Purification methodology and efficiency.

The choice of purification method for recombinant phytochrome was influenced by the desire to purify different structural forms of the photoreceptor using a uniform methodology. Since conventional purification protocols are strongly dependent on the structural characteristics of the desired product, an affinity "tagging" system was sought. Such tagging can be achieved by recombinant expression of an in frame protein fusion between phytochrome and a commercially available peptide for which affinity purification protocols have been developed. Initially fusion proteins having glutathione-S-transferase (GST, Pharmacia) or maltose binding protein (MBP, New England Biolabs) fused to the amino terminus of phytochrome were expressed and purified. In both cases the expressed fusion protein was soluble and displayed the expected size on western blots probed with phytochrome antibodies. Both fusion proteins could be purified using the appropriate affinity matrix as directed by the manufacturer. However, in neither case was the fusion protein competent to assemble with chromophore precursors using protocols established for assembly of native length recombinant apoprotein.

It has been shown that the amino terminal 10 kDa peptide of oat phyA is important in maintaining spectrophotometrically detectable integrity of the chromophore (Cherry et al. (1992) *Proc. Natl. Acad. Sci. USA*, 89: 5039–5043; Vierstra and Quail (1982). As a consequence of these results, the Strep Tag system was used.

The strep-tagged oat phytochrome A (ASPHYA-ST) expressed in yeast contains all of the amino acids coded by the cDNA from oats with the addition of fifteen amino acids at the carboxy terminus (FIG. 2). The ASPHYA-ST protein was engineered to include the entire native phytochrome sequence in order to minimize the possibility of structural perturbance or loss of phytochrome activity. The ten amino acids at the extreme C-terminus of ASPHYA-ST constitute the minimal strep-tag sequence required for interaction with streptavidin. This peptide was able to bind to streptavidin in a competitive manner with respect to biotin binding (Schmidt and Skerra (1993) *Prot. Eng.* 6: 109–122). This reversible interaction has been exploited for the commercial development of a streptavidin based affinity purification system for tagged proteins (Biometra). The five amino acid linker between the last native phytochrome amino acid and the Strep Tag in ASPHYA-ST is a result the subcloning procedure.

Although the Strep-Tag system was developed for expression and purification from *E. coli*, higher yields of phytochrome were obtained from *S. cerevisiae*. The majority of the soluble ASPHYA-ST expressed in bacteria was found in fragments smaller than 120 kDa on western blots probed with phytochrome antibodies. However, expression in yeast from the pMacphyAST plasmid (FIG. 2) yielded primarily full length ASPHYA-ST. Low yields and instability of oat phytochrome expressed in bacteria were observed for a number of native length phytochrome plasmid constructs as well as for the MBP and GST fusions. However, as with ASPHYA-ST, expression of these proteins in yeast results in primarily full length protein and higher yields. Yields of ASPHYA-ST reported here compare favorably to published yields for native length phytochrome expressed in *S. cerevisiae* (Kunkel et al. (1995) *J. Biol. Chem.* 270: 20193–20200). Recently yields have been shown to be ten fold higher than those obtained for *S. cerevisiae* expression systems.

The binding of ASPHYA-ST from the resolubilized and cleared ammonium sulfate pellet (ASP) to streptavidin-agarose occurs with an efficiency of 86%. Single step purification of ASPHYA-ST from the yeast soluble fraction is possible with streptavidin agarose, however addition of an ammonium sulfate precipitation step was found to improve the purification efficiency. The primary advantage of ammonium sulfate precipitation is concentration of the ASPHYA-ST protein and increase in its specific activity. A second advantage is the increased proteolytic stability of ASPHY-ST in the ASP fraction relative to the soluble fraction. This is important since the ASPHYA-ST sample must be incubated at room temperature with the appropriate chromophore precursor for 40 minutes prior to affinity chromatography for full assembly to occur. Chromophore assembly was performed at this stage to allow separation of free chromophore from holophytochrome during the affinity chromatography step. Avidin preincubation was performed during chromophore assembly to block biotinylated proteins from binding the streptavidin agarose in the subsequent affinity chromatography step. The strep-tag will not interact with avidin and is therefore free to bind the immobilized streptavidin. Using the above conditions a binding capacity of 200 $\mu$g ASPHYA-ST per milliliter bed volume of Sigma brand streptavidin-agarose was observed.

ASPHYA-ST is eluted from the affinity column with diaminobiotin which binds reversibly to streptavidin. A centrifugal concentrator is used to both concentrate ASPHYA-ST and to transfer the protein to a buffer containing ethylene glycol which is a cryoprotectant. The dilute nature of the eluate made assessment of specific activity and percent yield difficult to measure for this fraction. Therefore the combined efficiency of the elution and concentration step was measured, giving 53% recovery from the bound fraction. Thus the overall efficiency of the affinity chromatography step was 45%. The reversible nature of diaminobiotin binding to the immobilized streptavidin facilitates re-use of the column. Similar chromatographic efficiency was found between a first and second use of streptavidin agarose. The column was regenerated by washing with 20 column volumes of buffer W and stored at 4° C. in buffer W containing 0.02% azide.

Affinity purified ASPHYA-ST adducts are full length and pure to apparent homogeneity. Lanes on a Coomassie blue stained polyacrylamide gel were loaded with equivalent quantities of spectrophotometrically detected phytochrome. The reduction of total protein in each lane demonstrated the degree of purity achieved by ammonium sulfate precipitation and affinity chromatography. The purified ASPHYA-ST, had the same mobility as phytochrome purified from oats indicating that purified recombinant phytochrome is full length. The purity of ASPHYA-ST was demonstrated in one lane of the gel which showed no visible impurities despite a load of 1 mg pure ASPHYA-ST. Similar analysis with silver stained gels indicate no protein impurities in the affinity purified fractions.

Apoprotein and all three chromophore adducts yield similar purity and proteolytic stability as judged from PAGE analysis. A second measure of phytochrome purity is the specific absorbance ratio (SAR) between the $P_r$ absorbance peak intensity and the protein peak intensity at 280 nm for spectra obtained after illumination with saturating red light. An SAR of 1.0–1.1 has been shown to indicate the best purity for phytochrome isolated from oats to date (Lapko and Song (1995) supra.). The SAR for affinity purified ASPHYA-ST-P$\Phi$B ranges from 0.71–0.81. The reduced SAR for pure ASPHYA-ST may be due to the addition of a single tryptophan, within the strep-tag peptide, to the ten tryptophans already present in the native phytochrome sequence. Since tryptophan has the most significant molar absorption coefficient at 280 nm among the 20 amino acids (Segel, I. H. (1976) *Biochemical calculations, second ed., John Wiley and Sons, New York*) it was expected that tryptophan in the strep-tag contributed approximately 10% to the 280 nm peak therefore reducing the SAR of ASPHYA-ST by roughly 10%. Further small contributions to the 280 nm peak and reduction in SAR may occur due to an extra histidine and phenylalanine in the Strep-Tag.

Contribution of un-assembled phytochrome to the lower SAR cannot be completely dismissed but are most likely insignificant.

Photochemical comparison of ASPHYA(P$\Phi$B)-ST to oat phyA.

Figure 3A:
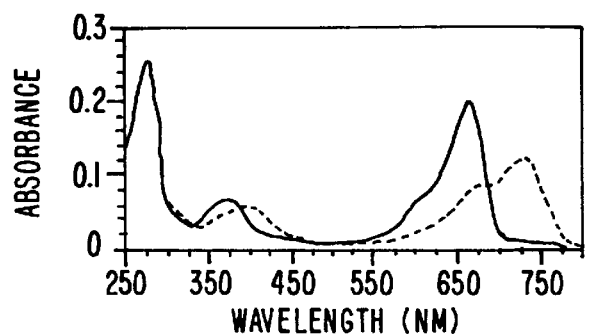
FIGS. 3A–D show the UV-VIS absorbance spectroscopy of three ASPHYAST species. Spectra A, B, and C are plotted on the same wavelength scale indicated below C. A) PΦB-ASPHYAST adduct: Pr spectrum (solid line) following 2 min irradiation with 660 nm actinic light, Pfr spectrum (dashed line) following 2 min irradiation with 738 nm actinic light. B) PCB-ASPHYAST adduct: Pr spectrum (solid line) following 2 min irradiation with 650 nm actinic light, Pfr spectrum (dashed line) following irradiation with 738 nm actinic light. C) apophyST species. D) Difference spectra obtained from the spectra shown in parts A, B, and C. PΦB-ASPHYAST (dotted line), PCB-ASPHYAST (solid line), and apoASPHYAST (dashed line). I-Bar length represents 0.05 absorbance units.

An important concern, with regard to the strep-tagged phytochrome, is that ASPHYA(P$\Phi$B)-ST have structure and function characteristics similar to native phyA. The well studied spectrophotometric properties of oat phytochrome A provide a sensitive method for comparison between the recombinant and native photoreceptor. The raw $P_r$ and $P_{fr}$ spectra shown in FIG. 3A and the difference spectra in FIG. 3D (dotted line) are visually indistinguishable from similar spectra for native phytochrome. A more quantitative comparison is provided in Table 1. For recombinant and native photoreceptor the

TABLE 1

Comparative properties of photoreversible adducts of recombinant phytochrome and phytochrome purified from oats. The parameter $A_\lambda^{Pfr}{}_{max}/A_{red\ shoulder}$ represents the ratio of absorbance of the far red maximum of $P_{fr}$ to the absorbance of the red shoulder for the same spectrum. The parameter $A_\lambda^{Pfr}{}_{max}/A_\lambda^{Pr}{}_{max}$ represents the ratio of peak maxima on the $P_r$ and $P_{fr}$ spectra respectively. The parameter $\Delta A_{max}/\Delta A_{min}$ refers to the ratio of the absorbance values of the peak maxima to the peak minima for the difference spectrum. *Data from Lagarias et al. (1987) Photochem. and Photobiol., 46: 5–13.

|  | Native phytochrome* | PhyST-P$\Phi$B | PhyST-PCB |
|---|---|---|---|
| Absorption Spectra |  |  |  |
| $P_r\lambda_{max}$(red) | 668 | 668 | 654 |
| $P_r\lambda_{max}$(blue) | 381 | 381 | 359 |
| $P_{fr}\lambda_{max}$(red) | 730 | 730 | 720 |
| $P_{fr}\lambda_{max}$(blue) | 402 | 400 | 377 |
| $A_\lambda^{Pfr}{}_{max}/A_{red\ shoulder}$ | 1.33 | 1.47 | 1.36 |
| $A_\lambda^{Pfr}{}_{max}/A_\lambda^{Pr}{}_{max}$ | 0.560 | 0.613 | 0.575 |

TABLE 1-continued

Comparative properties of photoreversible adducts of recombinant phytochrome and phytochrome purified from oats. The parameter $A_\lambda^{Pfr}{}_{max}/A_{red\ shoulder}$ represents the ratio of absorbance of the far red maximum of $P_{fr}$ to the absorbance of the red shoulder for the same spectrum. The parameter $A_\lambda^{Pfr}{}_{max}/A_\lambda^{Pr}{}_{max}$ represents the ratio of peak maxima on the $P_r$ and $P_{fr}$ spectra respectively. The parameter $\Delta A_{max}/\Delta A_{min}$ refers to the ratio of the absorbance values of the peak maxima to the peak minima for the difference spectrum. *Data from Lagarias et al. (1987) Photochem. and Photobiol., 46: 5–13.

|  | Native phytochrome* | PhyST-PΦB | PhyST-PCB |
| --- | --- | --- | --- |
| Difference Spectra |  |  |  |
| λ(ΔA$_{max}$) | 668 | 668 | 656 |
| λ(ΔA$_{min}$) | 732 | 732 | 720 |
| ΔA$_{max}$/ΔA$_{min}$ | 1.14 | 1.07 | 1.08 | wavelengths of peak maxima and minima are comparable, within the 2 nm resolution of the spectrophotometer. Interestingly, the ratios $A_\lambda^{Pfr}{}_{max}/A_\lambda^{Pr}{}_{max}$ and $A_\lambda^{Pfr}{}_{max}/A_{red\ shoulder}$ are higher for recombinant than for native phytochrome. Thus a larger fraction of recombinant phytochrome populates the $P_{fr}$ state at photoequilibrium than that seen for native oat phytochrome. One possibility is that the recombinant phytochrome may contain different post-translational modifications from those present in native phytochrome. This becomes interesting in light of the observation that phytochrome can be phosphorylated differentially in the $P_r$ and $P_{fr}$ states (Wong et al. (1986) J. Biol. Chem. 261: 12089–12097). It is possible that yeast cannot modify ASPHYA-ST because it is present as the apoprotein or because molecules required for modification of phytochrome are not present in yeast.

Figure 5:
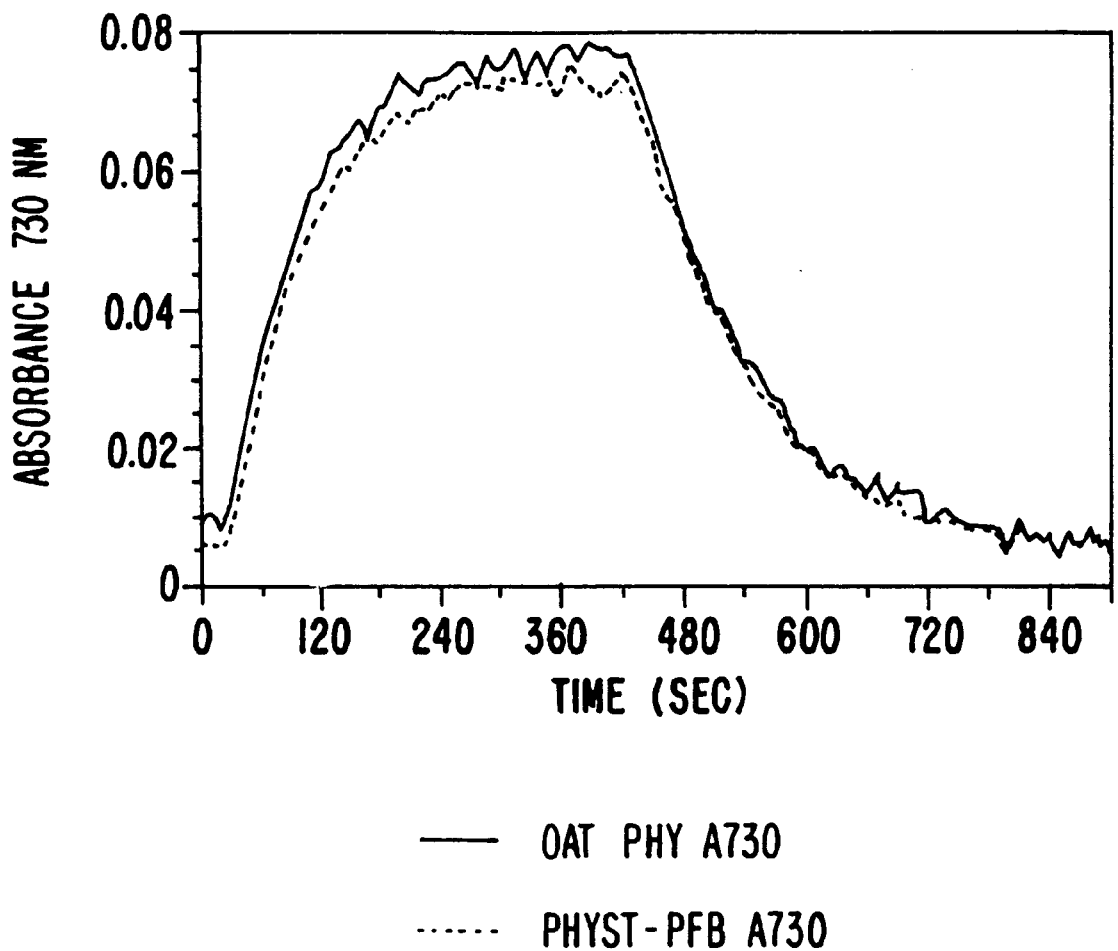
FIG. 5 shows a comparison of the phototransformation rates for native and recombinant oat phytochrome A (ASPHYAST). Phytochrome purified from oats (SAR=0.78) was diluted to optical density of 0.126 at 668 nm for Pr and strep-tagged phytochrome affinity purified from recombinant yeast (SAR=0.80) was diluted to an optical density of 0.121 at 668 nm for Pr. Both samples were irradiated with 730 nm light for 2 minutes. Acquisition was then initiated and after a 30 second time period, the actinic light was converted to 660 nm wavelength, then at 450 seconds actinic light was returned to 730 nm wavelength. Phototransformation was followed by absorption at 730 nm wavelength.

Recombinant ASPHYA(PΦB)-ST and native oat phyA display similar rates of phototransformation and dark reversion. Samples of purified yeast ASPHYA-ST and oat phytochrome A, diluted to similar optical density and irradiated with an equivalent fluence of actinic light, display superimposable rates of photoconversion (FIG. 5). This strongly implies that the recombinant phytochrome has quantum efficiencies of phototransformation between the $P_r$ and $P_{fr}$ states that are similar to those published for oat derived phytochrome A (Lagarias et al. (1987) Photochem. and Photobiol. 46: 5–13). Dark reversion of $P_{fr}$ was not evident for ASPHYA-ST samples monitored over a 12 hour period. The preceding spectrophotometric analyses indicate that recombinant Strep-Tagged oat phytochrome A is photochemically similar to the native photoreceptor. Therefore ASPHYA-ST is a legitimate tool for study of phytochrome photochemistry and photophysics.

Spectrophotometric characterization of non-native adducts of ASPHYA-ST.

Previously PCB has been shown to covalently assemble with recombinant apoprotein to yield a photoreversible adduct (Wahleithner et al. (1991) supra.). The PCB chromophore is similar in structure to the native chromophore with the exception of one less double bond in the conjugation system which results in the blue shifted difference spectrum. The PCB adduct is an important tool for phytochrome study because PCB is more readily available than the native chromophore precursor PΦB. For this reason the ASPHYA(PCB)-ST adduct was purified and spectrophotometrically characterized in this experiment.

Figure 3B:
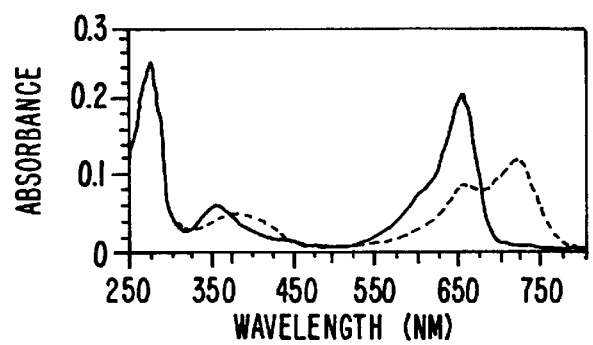

The $P_r$ and $P_{fr}$ spectra shown in FIG. 3b have peak shapes similar to those of the PΦB adduct The only visually noticeable difference from the native adduct is the blue shifted spectrum which is most evident in part D of FIG. 3 where the difference spectra of the two adducts are compared. Table 1 provides a more quantitative comparison of ASPHYA(PCB)-ST to both the native oat phytochrome and the ASPHYA(PΦB)-ST. The blue shift, relative to the native adduct, is evident in both the red and blue peaks of the spectra. It is interesting that, for ASPHYA(PCB)-ST, the ratios $A_\lambda^{Pfr}{}_{max}/A_\lambda^{Pr}{}_{max}$ and $A_\lambda^{Pfr}{}_{max}/A_{red\ shoulder}$ compare more favorably than ASPHYA(PΦB)-ST to native oat phytochrome. Thus the PCB adduct achieves a photoequilibrium, under red light, that is similar to that of native phytochrome. The similarity in SAR of the PCB and PΦB adducts indicate that the molar absorption coefficients of the two adducts are similar.

Figure 3C:
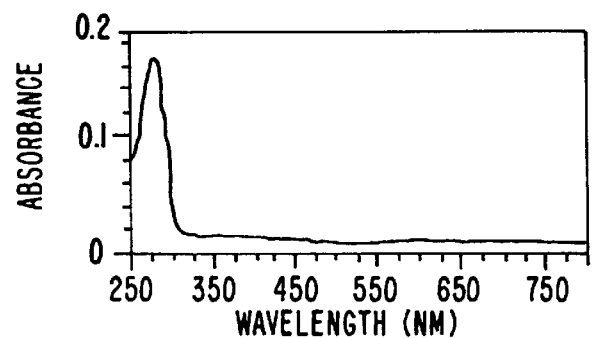
Figure 3D:
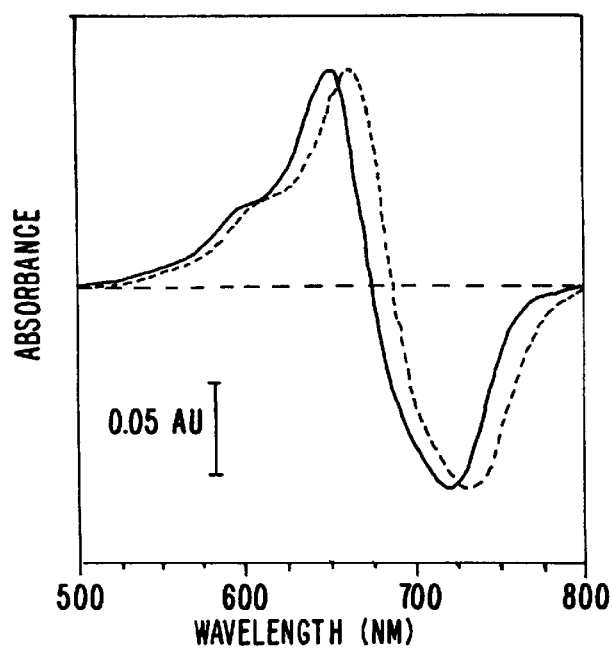

Purification of apoASPHYA-ST benefits the study of phytochrome assembly and biochemistry. This experiment establishes that apoASPHYA-ST purified from S. cerevisiae is full length and assembly competent. Rates of assembly for pure ASPHYA-ST are similar to those previously published for native length recombinant apoprotein in the ASP fraction (Li et al. (1995) supra.). The absorbance spectrum of apoASPHYA-ST is shown in FIG. 3C. As expected the apoprotein contributes absorbance only in the 280 nm region, and all other absorbance peaks seen for native phytochrome can be attributed to the linear tetrapyrrole chromophore. The lack of photoreversibility in FIG. 3D, and the absence of a signal on a zinc blot indicate that ASPHYA-ST expressed in S. cerevisiae is an apoprotein which has not assembled in vivo. This contrasts with the recent observation that phytochrome overexpressed in the methylotropic yeast, Pichia pastoris assembles with a PΦB-like chromophore in vivo.

Expression and purification of recombinant phytochrome from yeast allows introduction of novel functions in the photoreceptor, and convenient analysis of the engineered product. The ASPHYA(PEB)-ST adduct provides an example of novel function introduced into phytochrome. It was previously reported that this adduct is fluorescent, and this phenomenon was used to measure the rates of phytochrome assembly (Li et al. (1995) supra.).

Figure 4A:
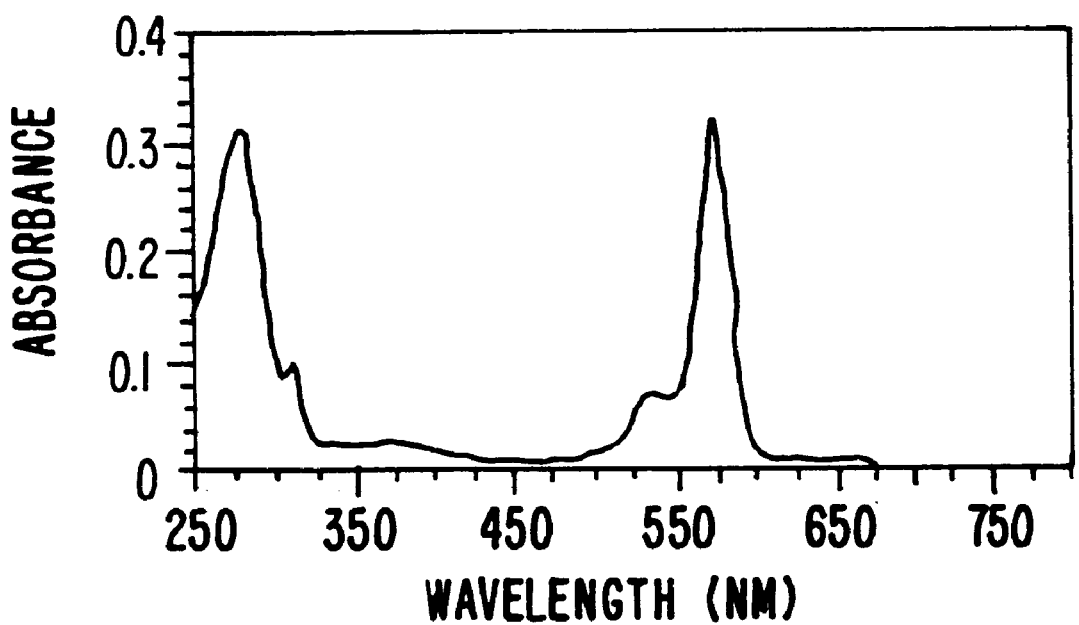
FIGS. 4A–B show spectrophotometric analysis of ASPHYAST-PEB adduct. All three spectra are plotted on the same wavelength scale as indicated below B. A) UV-Vis absorption spectrum. B) Normalized fluorescence excitation spectrum (solid line) and emission spectrum (dotted line).
Figure 4B:
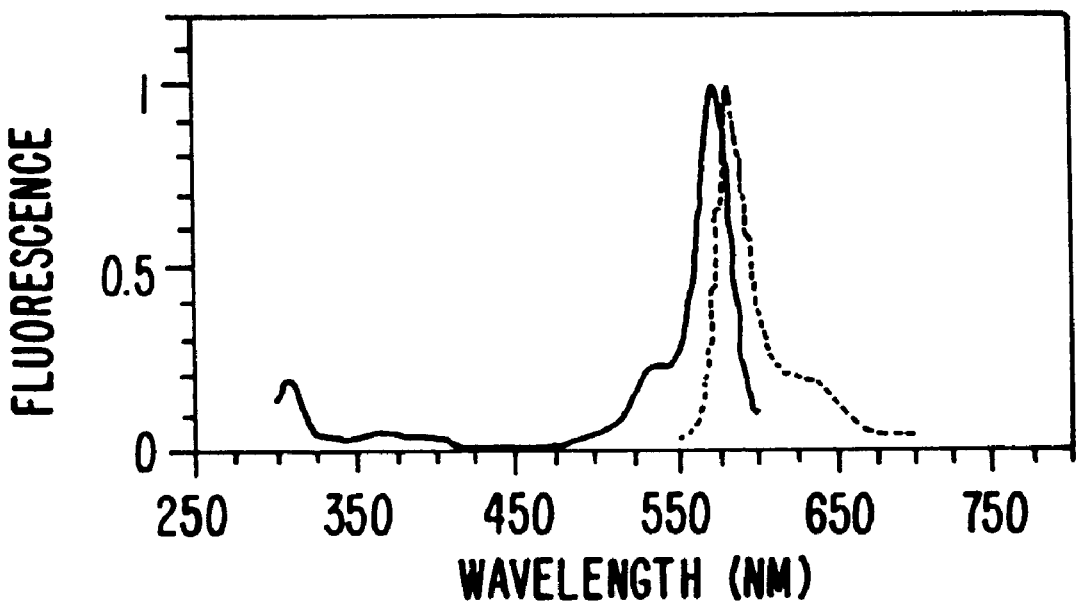

FIG. 4 shows the absorbance and fluorescence spectra of ASPHYA(PEB)-ST. The absorbance displayed by the chromophore of the PEB adduct is much narrower than the $P_r$ peaks for the PΦB and PCB adducts. This indicates that the PEB chromophore is held more rigidly, having fewer degrees of freedom than the photoreversible chromophores. This is further supported by comparison of the SAR of the ASPHYA(PEB)-ST adduct (1.0) which is higher than that observed for ASPHYA(PΦB)-ST adduct (0.71–0.81). Assuming both chromophores assemble with equal efficiency this implies that the molar absorption coefficient of the PEB adduct will be higher than that published for phytochrome (Lagarias et al. (1987) supra.). The absorbance spectra of PHYA(PEB)-ST is superimposable on the excitation spectrum indicating that this adduct is in fact responsible for the fluorescence phenomena reported previously (Li et al (1995) supra.). Photoreversibility for ASPHYA (PEB)-ST is not spectrophotometrically detectable using actinic light in the red or green regions of the spectrum.

Molecular size analysis

The Strep-Tag provides a sensitive epitope for detection of ASPHYA-ST. In a western blot containing phytochrome purified from oats and the four forms of ASPHYA-ST discussed above, the commercially available streptavidin-alkaline phosphatase conjugate is able to detect all four ASPHYA-ST adducts but does not cross-react with native phytochrome devoid of the tag. The same blot was also visualized using previously described zinc blot protocols (Li and Lagarias (1992) supra.). Comparison of the two blots indicates that the nature of the chromophore adduct affects the intensity of the zinc blot signal despite equal protein loading evident using streptavidin-alkaline phosphatase detection. The relative intensities of the zinc blot signal (PΦB<PCB<PEB) increase with decreasing length of the conjugation system in the chromophore which is expected since the blot is excited with UV light.

ASPHYA-ST purified from yeast is a dimer with quaternary structure in the $P_r$ and $P_{fr}$ forms similar to that of native phytochrome. A summary of size exclusion chromatography data obtained for the four forms of ASPHYA-ST discussed above is presented in table 3. The $P_{fr}$ forms of the photoreversible adducts (PΦB and PCB) have a larger apparent size than the $P_r$ forms which is consistent with results for native oat phyA in this study and in previously published work (Lagarias and Mercurio (1985) *J. Biol. Chem.* 260: 2415–2423).

TABLE 2

Molecular size analysis of purified ASPHYA-ST adducts. Native molecular sizes were estimated by size exclusion chromatography as described above. Size estimates which are out of range of the standard curve are indicated (*). Molecular size of purified denatured phyST adducts were estimated by SDS PAGE analysis as described above.

| Phy Adduct | MW PR (kDA) | MW Pfr (kDa) |
| --- | --- | --- |
| Oat phy A | 295 | 513 |
| ASPHYA(PΦB)-ST | 288 | 539 |
| ASPHYA (PCB)-ST | 319 | 757* |
| ASPHYA (PEB)-ST | 361 | N/A |
| apoASPHYA | 361 | N/A |

The PCB adduct is significantly larger in the $P_{fr}$ form such that its size surpasses that of the largest molecular weight standard, thus its size cannot be accurately determined in this experiment. The $P_r$ forms of the nonphotoreversible adducts (apo and PEB) are slightly larger than those of the photoreversible forms. This may be due to a more open conformation in the apo and PEB bound phytochromes relative to the native chromophore adduct. Size differences observed for ASPHYA-ST adducts using SEC appear to be due to higher order structure since PAGE analysis indicates no difference in size for denatured ASPHYA-ST adducts.

Conclusion

This example demonstrates that recombinant Strep-Tagged oat phytochrome A can be efficiently purified to homogeneity from the yeast *Saccharomyces cerevisiae*. The PΦB adduct of recombinant Strep-Tagged oat phytochrome A exhibits biochemical and spectrophotometric properties that are indistinguishable from those of phytochrome purified from native oats. Other adducts including apoASPHYA-ST, ASPHYA(PCB)-ST and ASPHYA(PEB)-ST can be purified to apparent homogeneity. Purification of these bilin adducts enhances the utility of recombinant expression systems for the modification and analysis of phytochrome structure and analysis of functional consequences. Accurate characterization of phytochrome with engineered functions is facilitated by the ability to purify ASPHYA-ST. For example it was shown here that the fluorescent excitation spectrum and absorption spectrum of the purified ASPHYA (PEB)-ST adduct are superimposable indicating that the phytochrome-PEB adduct is the exclusive fluorescent species observed in earlier experiments.

EXAMPLE 2

Method for Assaying Recombinant Apoprotein Polypeptides

This example describes an expression system in the yeast, *Pichia pastoris*, that biosynthesizes phytochromobilin. By transfecting the yeast with nucleic acids encoding apoprotein polypeptides, *Pichia pastoris* can be used to test various modified apoproteins for desired properties, for instance the ability to form a fluorescent adduct with phytochromobilin.

Materials and Methods

Plasmid construction for apoprotein expression.

A full length phytochrome cDNA from the mcphylb gene of the green alga *Mesotaenium caldariorum* was constructed by RT-PCR of poly $A^+$ mRNA obtained from algal protoplasts (Lagarias et al., *Plant Mol. Biol.* 29:1127–1142 (1995)). The stop codon of the mcphylb cDNA in pBluescript SK+ (Stratagene, La Jolla Calif.) was then mutagenized to create an XhoI site. A 3.5 kbp XhoI fragment containing the full length mcphylb cDNA was subcloned into the SalI site of the vector pASK75 (Biometra, Tampa Fla.) to create construct pMCPHYlbST with an in frame fusion between mcphylb and the Strept-Tag peptide (Schmidt et al. *J. Chromatog.* 676:337–345 (1994)). A 3.5 kbp XhoI-HindIII fragment of pMCPHYlbST was transferred to pBluescript SK+ to create flanking EcoRI sites. This EcoRI fragment was then subcloned into the Pichia expression vector pHIL-D2 (Invitrogen, San Diego Calif.) for intracellular protein expression in *Pichia pastoris* cells.

*Pichia pastoris* cell culture.

A *Pichia pastoris* strain GS 11 5-MCPHYlbST containing algal phytochrome cDNA integrated into the AOX1 locus was isolated by electroporation of parent strain GS115 (his4, Mut⁻) and selection according to the manufacturer's directions (Invitrogen). Several individual colonies of this strain were inoculated into 10 ml liquid MGY medium (1.34% yeast nitrogen base without amino acids, 1% glycerol, 0.4 mg/L biotin) and grown for approximately 16–20 hours at 30 C. with shaking at 300 rpm. When the $OD_{600}$ reached 2–6, 5–6 ml of the culture was used to inoculate 1 L MGY medium in a 2.8 L Fernbach flask and incubated at 30 C. with shaking for 16–20 hours. Induction of foreign protein expression was performed when an $OD_{600}$ between 2 and 6 was observed. At this point, cells were harvested by centrifugation, resuspended in 200 ml MM medium (1.34% yeast nitrogen base without amino acids, 0.5% methanol, 0.4 mg/L biotin) and transferred to a sterile 2.8 L Fernbach flask. Cells were allowed to grow with shaking at 30 C. for up to 4 days; each day 100% methanol was added to give a final concentration of 0.5%. As controls, the Pichia strains GS115-Albumin (HIS4, Mut$^s$) and GS115 (Invitrogen) were cultured in the identical way as above except that 40 mg/ml histidine was added to all culture media for the latter. After the appropriate induction period, cells were harvested by centrifugation at 4 C. and washed once with ice cold deionized water. Washed cell pellets were either subjected to cell lysis immediately or frozen with liquid $N_2$ and stored at −20 C. for later analysis.

Soluble protein extraction from yeast cells.

Thawed yeast cells were lysed with a Bead-Beater (Biospec Products, Bartlesville Okla.) after suspending 12–15 g cells in 8–12 ml ice cold homogenization buffer (200 mM Tris-HCl, pH 8.0, 100 mM NaCl, 1 mM EGTA, 1% mM EGTA, 1% (v/v) 2-mercaptoethanol, 1% (v/v) DMSO, 1.5 µg/ml leupeptin, 3 µg/ml pepstatin A, 1 mM benzamidine and 1 mM PMSF). Three to four 30–40 sec pulses were used for cell homogenization with cooling in a dry ice-ethanol bath for 1 min between each pulse. The crude homogenate was clarified by ultracentrifugation at 100,000×g at 4 C. for 40 min and the soluble protein fraction decanted from the pellet. For small scale soluble protein extraction, frozen cells were lysed with the same buffer using a Mini-Bead Beater (Biospec Products) for five 1-min pulses with cooling on ice between each pulse.

Spectrophotometric phytochrome assays.

In vivo spectrophotometric measurements of holophytochrome in Pichia strain GS115-MCPHYlbST were obtained with an Aviv/Cary 14DS UV-visible spectrophotometer as described previously (Li et al. *Proc. Natl. Acad. Sci. USA* 91:12535–12539 (1994)). For in vitro spectrophotometric assays, ammonium sulfate was added to the soluble protein fraction to a concentration of 0.23 g/ml. The mixture was incubated on ice for at least 1 hour and the precipitate collected by centrifugation for 20 min at 17,000×g at 4 C. The protein pellets were dissolved in 100 mM Tris-HCl, pH 8.0 containing 1 mM EDTA, 1 mM DTT and 1 mM PMSF. Holophytochrome concentrations were determined with a HP8450A UV/visible spectrophotometer using the absorbance difference assay (Li et al. *J. Biol. Chem.* 267:19204–19210 (1992)). For in vitro assembly studies, 3E-phycocyanobilin (PCB) or 3E-phytochromobilin (PΦB) was added to 4 μM and incubated at 28 C. under green safe light for 30 min prior to spectrophotometric measurements.

SDS-PAGE, zinc-blot and immunoblot analyses.

Protein samples were analyzed by SDS-PAGE with the Laemmli buffer system. After electrophoresis, proteins were electrophoretically transferred to polyvinylidene difluoride (PVDF) membranes (Immobilon P, Millipore) for 1 h at 100 V. This membrane was then used for zinc-blot and immunoblot analyses as described previously (Wahleithner et al. (1991)). For immunoblot detection, recombinant phytochrome was probed with alkaline phosphatase conjugated streptavidin (Amersham) and developed as described previously ((Wahleithner et al. (1991)). For time course experiments, bilin-linked proteins bound to PVDF membranes were detected by direct zinc-dependent fluorescence and phytochrome was quantitated immunochemically by chemifluorescence using a Molecular Dynamics Storm 860 instrument and image Quant software. The excitation wavelength used for zinc fluorescence measurements was 635 nm and the PMT setting was 1000. For chemifluorescence detection, PVDF membranes were developed with Vistra ECF Western blotting reagent pack (Amersham) and the fluorescence was detected at 540–560 nm with excitation at 450 nm.

PΦB synthase assays.

For a standard 1 ml assay mixture, soluble protein extracts (730 μl) were used as enzyme source. The reaction mixture consists of an NADPH regenerating system (6.5 mM glucose-6-phosphate, 0.82 mM NADP$^+$ and 1.1 units/ml glucose-6-phosphate dehydrogenase), 10 μM BSA, 4.6 μM spinach ferredoxin and 0.025 units/ml ferredoxin-NADP$^+$ reductase (all final concentrations). The reaction was initiated by adding BV in DMSO to give a final concentration of 10 μM BV and 1% (v/v) DMSO. Reaction mixtures were incubated at 28–30 C. under green safe light for 30 min. Bilins synthesized in the reaction were partially purified on a C18 Sep-Pak cartridge (Waters-Millipore Corp., Milford Mass.) as described (Terry et al. (1995) *J. Biol. Chem.*, 270: 11111–11118). Crude bilins were analyzed by C18 reversed phase HPLC using a Varian 5000 liquid chromatography and a Phenomenex Ultracarb 5 μ ODS20 column (4.6 mm×250 mm) with a 4.6 mm×30 mm guard column of the same material. The mobile phase was 50:50 (v:v) acetone: 10 mM formic acid in water. The column eluate was monitored at 380 nm with a Varian UV100 flow through absorbance detector.

Results

Expression of algal phytochrome yields photochromic green yeast.

*Pichia pastoris* strain GS115-MCPHYlbST containing an integrated algal phytochrome cDNA became increasingly light green in color over a 4 day induction period. In contrast, cells obtained from methanol-induced cultures of parent strain GS115 and GS115-Albumin in which extracellular expression of serum albumin was placed under control of the AOX1 promoter appeared off-white. Since the pale green color of the apoprotein-expressing cells was retained in the clarified protein extract following homogenization and ultracentrifugation, the extracts were assayed for photochemically active phytochrome. A phytochrome-like difference spectrum was observed with absorption maximum and minimum at 660 nm and 730 nm, respectively. No phytochrome-like difference spectrum was observed in control assays of soluble extracts from the parent strain GS115 and the GS115-derived Pichia strains expressing albumin.

The photochromic activity observed in algal phytochrome-expressing yeast cells is correlated with the formation of a covalent bilin-apoprotein adduct. The presence of an orange fluorescent species in the zinc blot of these cultures and its absence in the control indicates that the production of the bilin adduct is dependent upon apoprotein expression. Immunoblot analyses confirm that the fluorescent 120 kDa adduct corresponded to the phytochrome polypeptide. Since phytochrome assembly proceeds spontaneously when bilin precursors and apoprotein are co-incubated (Lagarias et al. *Proc. Natl. Acad. Sci. USA* 86:5778–5780 (1989)), these results indicate that *Pichia pastoris* cells manufacture a functional precursor of the phytochrome chromophore.

The time course of the formation of the bilin-apoprotein adduct during induction of apoprotein expression with methanol was next addressed. Levels of both apoprotein and holophytochrome were determined using immunochemical and zinc-dependent fluorescence methodologies. In the experiment shown in FIG. 3, apoprotein accumulates rapidly and reaches a saturating level within the first two days of induction. By comparison, the amount of bilin ligation continuously increases for the four day period whereupon nearly 50% of the phytochrome had received a bilin chromophore. These results are consistent with the time dependency of the formation of the green pigmentation of the apoprotein-expressing Pichia strain and also show that the synthesis of apoprotein initially exceeds the capacity of the cells to manufacture chromophore.

Since other researchers have expressed recombinant phytochrome in the yeast *Pichia pastoris* but have not reported photoactive phytochrome synthesis, the possibility of an algal or bacterial contaminant in the cultures was considered. In this regard, an unidentified green contaminant has been observed in Pichia suspension cultures. A number of approaches were taken to address this possibility. First, differential sedimentation failed to reveal two types of cell populations; indeed, cell pellets were uniformly pale green in appearance. Second, apoprotein-expressing cultures were grown and induced in the presence of 100 μg/ml ampicillin to inhibit the growth of a bacterial contaminant. Soluble protein extracts prepared from these cells also contained photoactive phytochrome. Third, apoprotein-expressing cells from induced suspension cultures were examined by phase contrast and fluorescence microscopy. No evidence for other types of microorganisms were observed by these investigations. The cell line was also streaked out on a wide variety of bacterial media, and on all media examined where any growth was observed, only a single colony morphology was observed. Fourth, spectrophotometric measurements were undertaken on living cells to assuage the possibility that assembly had occurred in vitro following homogenization of Pichia cells and a potential cell contaminant. Based on these observations, it was concluded that *Pichia pastoris* cells can synthesize a phytochrome chromophore precursor. The recombinant algal phytochrome chromophore precursor is phytochromobilin.

Since the difference spectrum of the Pichia bilin adduct is nearly indistinguishable from that of phytochrome A isolated from higher plants, these studies suggest that Pichia cells synthesize phytochromobilin (PΦB), the natural phytochrome chromophore precursor. Support for this conclusion was first obtained from experiments to reconstitute recombinant algal apoprotein in crude protein extracts with the chromophore precursors, PΦB and its analog phycocyanobilin (PCB). These experiments were complicated by prior assembly of apoprotein with the endogenous bilin pigment in Pichia cells. For this reason, the experimentally measured difference spectrum of Pichia protein extracts incubated with bilins reflects both in vivo and in vitro assembly. Difference spectra of PΦB- and PCB-apoprotein adducts could be obtained by subtracting the difference spectrum of the pre-assembled adduct from that obtained after in vitro bilin incubation. In this particular experiment, half of the apoprotein had pre-assembled with the Pichia bilin based upon a roughly two-fold increase in spectrophotometrically active phytochrome after in vitro bilin incubation. The wavelength positions of the difference maxima and minimum of the PΦB-adduct are quite similar to those of the photochromic species obtained directly from Pichia cells although the spectrum of the PCB-adduct is blue-shifted. Since a similar 10 nm blue shift is observed when PCB is substituted in place of PΦB for in vitro assembly with recombinant oat apoprotein A, the spectral data strongly supports the hypothesis that the Pichia pigment is PΦB.

Additional support for this hypothesis was obtained by assaying Pichia cell extracts for PΦB synthase, the enzyme responsible for the conversion of biliverdin IXα to 3Z-PΦB (Terry et al. (1995) *J. Biol. Chem.* 270:11111–11118). Soluble protein extract from the parent Pichia strain GS115 contain the activity necessary for converting BV to PΦB as detected by its functional assembly with recombinant oat apoprotein. A similar activity is present in extracts from both apoprotein- and albumin-expressing Pichia cell lines. These results demonstrate that apoprotein is not a prerequisite for the expression of this activity in Pichia cells. HPLC analyses also support the conclusion that BV is converted to both 3Z- and 3E-PΦB by an activity found in Pichia extracts. BV is converted to pigments that co-elute with the two phytochromobilin isomers. Both pigments yield photoactive holophytochrome following HPLC purification and in vitro assembly with oat apoprotein A from *S. cerevisiae*. In addition, these analyses demonstrate that neither pigment is produced if Pichia protein extract is omitted from the assay mixture.

Interestingly, heat inactivation treatment for 5 min at 100 C. failed to inhibit the PΦB synthase activity found in the Pichia extract. Since PΦB synthase from higher plants is heat sensitive, these results suggest that the Pichia enzyme is quite different from the plant enzyme or alternatively, that BV can be non-enzymatically converted to PΦB by a Pichia factor. In view of the chemical structure of PΦB however, it is difficult to envisage a non-enzymatic mechanism for the conversion of BV to PΦB. Taken together with the observation that the activity can be recovered following precipitation with ammonium sulfate, the data indicate that an enzyme is responsible for the synthesis of PΦB in Pichia cells.

EXAMPLE 3

Reconstitution and Fluorescence of Phytofluors In Vivo

Materials and Methods
Phycoerythrobilin (PEB) Isolation.

PEB was isolated from acetone-treated *Porphyridium cruentum* cells (Cornejo, et al. (1992) *J. Biol. Chem.*, 267:14790–14798) or from *Porphyra yezoensis ueda* (nori) under dim light as follows. Freeze dried nori (5 g) was frozen with liquid nitrogen, pulverized by mortar and pestle, and extracted twice with 200 ml de-ionized water. The dark purple liquid was filtered through cheese cloth, precipitated at 4° C. with 65% saturated $(NH_4)_2SO_4$, and centrifuged at 17,000×g for 20 min. The protein pellet was resuspended in 100 ml of methanol containing 200 mg $HgCl_2$ and refluxed under nitrogen at 45° C. with stirring for 16–24 hours in the dark. Centrifugation at 17,000×g for 20 min yielded a blue-green soluble fraction from which mercury was removed by addition of 200 12-mercaptoethanol followed by re-centrifugation. PEB was isolated from the soluble fraction by solid phase extraction and HPLC purified (Wu et al (1996) *Proc. Natl. Acad. Sci. USA*, 93: 8989–8994).

Recombinant Phytochrome Expression and Purification.

Strep-Tagged ASPHYA was expressed in *Saccharomyces cerevisiae* strain pMASPHYA-ST/29A and the 40% ammonium sulfate-precipitated (ASP) protein fraction obtained as described previously (Murphy et al. (1997) *Photochem. Photobiol.*, 65: 750–758). Strep-Tagged MCPHY was expressed in *Pichia pastoris* strain GS115-MCPHY1bST and the ASP protein fraction obtained as described previously (Wu et al. (1996) *Proc. Natl. Acad. Sci., USA*, 93: 8989–8994) except that cells were induced under white light with a fluence rate of 67 $\mu M$ $m^{-2}$ $sec^{-2}$. The amino terminal 514 residue fragment of Synechocystis sp PCC6803 phytochrome (N514) was expressed in *E. coli* strain pASKN514/DH5α. Cells were lysed in a French pressure cell at 10,000 psi and the 40% ASP fraction obtained (Murphy et al. (1997) *Photochem. Photobiol.*, 65: 750–758). Resolubilized ASP fractions for ASPHYA, MCPHY1 and N514 were incubated with 5–10 M PEB for 1 h at 25° C. and purified by streptavidin-agarose affinity chromatography (Id.). Purified phytochrome was stored in TEGED buffer (25 mM Tris HCl pH 8.0, 25% ethylene glycol, 1 mM EDTA, and 1 mM DTT) at –80° C. until further analysis.

Absorbance and Fluorescence Spectrophotometry.

All instruments were equipped with temperature controlled cuvette holders and samples were maintained at 25° C. Absorption spectra were obtained using an HP8453 UV-visible spectrophotometer. Corrected fluorescence excitation, emission, and polarization spectra were obtained with an SLM Aminco Bowman AB2 fluorimeter. Monochrometers were adjusted to 2 nm bandpass for all fluorescence measurements on the AB2. Phase-modulated fluorescence lifetime measurements utilized an ISS Inc. multifrequency cross-correlation fluorimeter with 20 modulation frequencies ranging from 5 MHz to 220 MHz, a cross correlation frequency of 80 MHz, 545 nm excitation (8 nm bandwidth) and 580 nm long pass emission filters.

Molar Absorption Coefficient Determinations.

Affinity-purified phytofluors were exchanged into 25 mM N-methylmorpholine acetate buffer pH 7.8 using steric exclusion-HPLC (Murphy et al. (1997) *Photochem. Photobiol.*, 65: 750–758). Following absorption spectra determination, triplicate samples were removed, lyophilized, and acid hydrolyzed for 24 hr prior to quantitation with a Beckman 6300 amino acid analyzer at the UCD Protein Structure Lab. Molar recoveries of Asp, Glu, Pro, Gly, Ala, Val, Ile, Leu, Tyr, Phe, Lys, and Arg were used to determine protein concentration.

Fluorescence Quantum Yield Determination.

Fluorescence quantum yield measurements for phytofluors were made relative to both purified *Porphyridium cruentum* B-PE and fluorescein (Molecular Probes, Inc.; Cat. No F-1300). Quantum yield measurements for free PEB were made relative to fluorescein. Affinity-purified phytofluors were diluted in TEGED buffer to $A_{535}$=0.01–0.02, PEB was diluted to peak absorbance of 0.04–0.05 in 10 mM sodium-succinate pH 4.0 or 10 mM sodium-glycinate pH 10.0, B-PE was diluted to $A_{535}$=0.01–0.02 in 100 mM sodium phosphate pH 6.8, and fluorescein was diluted to A450= 0.01–0.02 in 0.1 N NaOH. Emission spectra were obtained by excitation at the respective wavelengths listed above, instrument-corrected, converted to wavenumber scale, and bandpass-corrected by multiplying emission intensity at each wavelength by the square of the respective wavelength (Lakowicz (1983) *Principles of Fluorescence Spectroscopy*. Pp 1–496, Plenum Press, New York). The resulting emission spectra were integrated and the relative quantum yield calculated according to Parker et al. (1960) *The Analyst*, 85: 587–600. Fluorescence quantum yield estimates used values of $\Phi_f$=0.98 for B-PE (Grabowski et al. (1978) *Photochem. Photobiol.*, 28: 39–45) and $\Phi_f$=0.85 for fluorescein (Parker et al. (1960) supra.).

Photobleaching Measurements.

ASPHYA-PEB, B-PE, and fluorescein samples were diluted into 2 ml of the appropriate buffer (listed above) to give a final peak optical density of 0.06. Samples were maintained at 25° C. in stirred 1 cm×1 cm quartz cuvettes, and absorbance values obtained at 10 min intervals for samples irradiated with white light using a quartz halogen actinic light source described previously (Kelly et al. (1983) *J. Biol. Chem.*, 258:11025–11031) or maintained in complete darkness. The absorbance peak at each time point was divided by the initial absorbance, multiplied by 10 and the logarithm calculated to obtain the Y axis values. Linear regressions were fitted to the data obtained under white light yielding $r^2$ values of 0.903 for ASPHYA-PEB, 0.997 for B-PE, and 0.998 for fluorescein. Photobleaching rates were adjusted for relative absorption cross-section and relative actinic light intensity by conversion of the absorbance spectra to the wavenumber scale, multiplying the absorbance at each wavenumber by the intensity of actinic light, and integrating the area under the resulting spectra.

pH Dependence of ASPHYA Stability.

Solutions used for assays contained 25% ethylene glycol, 1 mM EDTA, 1 mM DTT and 25 mM of one of the following buffers: MES-KOH pH 5.5–6.5, MOPS-KOH pH 6.5–7.5, Tris-HCl pH 7.5–8.5, or Glycine-KOH pH 8.5–10.0 ASPHYA-PEB in TEGED pH 8.0 was diluted at least 10 fold into the respective buffer, incubated for 2 hours in the dark at 25° C., centrifuged at 16,000×g for 10 min, and the soluble fraction used for absorbance and fluorescence spectroscopy.

Confocal Microscopy of Arabidopsis Seedlings.

Hy1, L-er wild type and hy1 phyA phyB triple mutant seedlings were germinated in complete darkness and grown for 4 days as described (Lagarias et al. (1997) *Plant Cell*, 9: 675–788). Representative seedlings of each plant line were placed on a microscope slide and bathed in a freshly prepared solution of 200 M PEB in 10 mM PIPES buffer pH 6.7 containing 10% (v/v) DMSO. After 10–15min incubation, seedlings were extensively washed with 10 mM PIPES buffer pH 6.7 and placed under a coverslip. Fluorescence images were obtained using Zeiss LSM 410 Confocal Microscope with 568 nm argon-krypton laser excitation and dual channel emission detectors filtered with a 590–610 nm bandpass filter (580 dichroic mirror) and a 670–810 nm bandpass filter (630 nm dichroic mirror).

Results and Discussion

Phytofluors are readily reconstituted in vitro.

Incubation of PEB with full length recombinant oat apophytochrome A yielded a covalently bound, orange fluorophore, termed ASPHYA-PEB (Li et al. (1995) *Biochem.* 34: 7923–7930; Murphy et al. (1997) *Photochem. Photobiol.*, 65: 750–758.). To test whether phytofluors could be produced from evolutionarily distant photosynthetic organisms, recombinant apophytochromes from the green alga *Mesotaenium caldariorum* and the cyanobacteria Synechocystis sp PCC6803 were incubated with PEB and purified to homogeneity. Full length constructs were employed for ASPHYA-PEB and Mesotaenium phytochrome-PEB (MCPHY1-PEB) adducts. An N-terminal 514 amino acid fragment of the cyanobacterial phytochrome (N514) was investigated because of its smaller size, monomeric structure, and ability to assemble with PΦB to produce a photoactive adduct indistinguishable from the full length construct. Like ASPHYA, incubation of MCPHY1 and N514 with PEB yielded covalent bilin adducts.

TABLE 3

Comparison of photophysical properties of common fluorescent probes in aqueous solution. Column headings are $\lambda_{ex}^{max}$ for excitation maxima, $\lambda_{em}^{max}$ for emission maxima, $\epsilon$ for molar absorption coefficient, $\Phi_f$ for fluorescent quantum yield. The brightness is obtained by multiplying $\epsilon \times \Phi_f$. All values are based on monomers or single molecules, except for B-PE values which are based on the (αβ)γ subunit.

| Probe | $\lambda_{ex}^{max}$ (nm) | $\lambda_{em}^{max}$ (nm) | $\epsilon(\lambda^{max})$ ($M^{-1}$ $cm^{-1}$) | $\Phi_f$ | Brightness $\epsilon(\lambda^{max}) \times \Phi_f$ | Relative Brightness |
|---|---|---|---|---|---|---|
| B-PE | 545 | 575 | $2.41 \times 10^6$ | 0.98 | $2.4 \times 10^6$ | 20.9 |
| ASPHYA-PEB | 576 | 586 | $1.13 \times 10^5$ | 0.70 | $7.9 \times 10^4$ | 1.0 |
|  |  |  | $(1.65 \times 10^5)$ |  | $(1.15 \times 10^5)$ | 1.43 |
| MCPHY-PEB | 574 | 583 | $7.76 \times 10^4$ | 0.82 | $6.4 \times 10^4$ | 0.80 |
| N514-PEB | 580 | 590 | $8.54 \times 10^4$ | 0.72 | $6.1 \times 10^4$ | 0.76 |

TABLE 3-continued

Comparison of photophysical properties of common fluorescent probes in aqueous solution. Column headings are $\lambda_{ex}^{max}$ for excitation maxima, $\lambda_{em}^{max}$ for emission maxima, $\epsilon$ for molar absorption coefficient, $\Phi_f$ for fluorescent quantum yield. The brightness is obtained by multiplying $\epsilon \times \Phi_f$. All values are based on monomers or single molecules, except for B-PE values which are based on the $(\alpha\beta)\gamma$ subunit.

| Probe | $\lambda_{ex}^{max}$ (nm) | $\lambda_{em}^{max}$ (nm) | $\epsilon(\lambda^{max})$ (M$^{-1}$ cm$^{-1}$) | $\Phi_f$ | Brightness $\epsilon(\lambda^{max}) \times \Phi_f$ | Relative Brightness |
|---|---|---|---|---|---|---|
| Fluorescein | 490 | 530 | $8.8 \times 10^4$ | 0.85 | $7.5 \times 10^4$ | 0.95 |
| Aequoria GFP | 395 (475) | 508 | $3.0 \times 10^4$ | 0.85 | $2.6 \times 10^4$ | 0.33 |
| Free PEB |  |  |  |  |  |  |
| pH 4 | 590 | 617 | $2.06 \times 10^4$ | 0.003 | $6.18 \times 10^1$ | 0.0008 |
| pH 10 | 536 | 616 | $1.64 \times 10^4$ | 0.008 | $1.31 \times 10^2$ | 0.0017 |

Figure 7A:
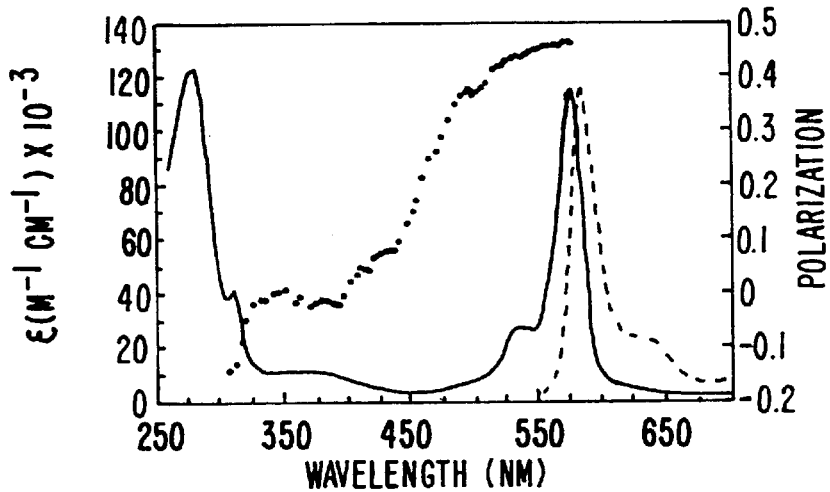
FIGS. 7A–C. Spectroscopic analysis of recombinant phytochrome-PEB adducts. Absorption spectra are plotted as molar absorption coefficients (solid lines). Fluorescence emission spectra, obtained by excitation at 545 nm (dotted line), are normalized relative to the respective PEB absorption peak. The fluorescence polarization spectra of ASPHYA-PEB is overlaid with values labeled on the axis to the right.
Figure 7B:
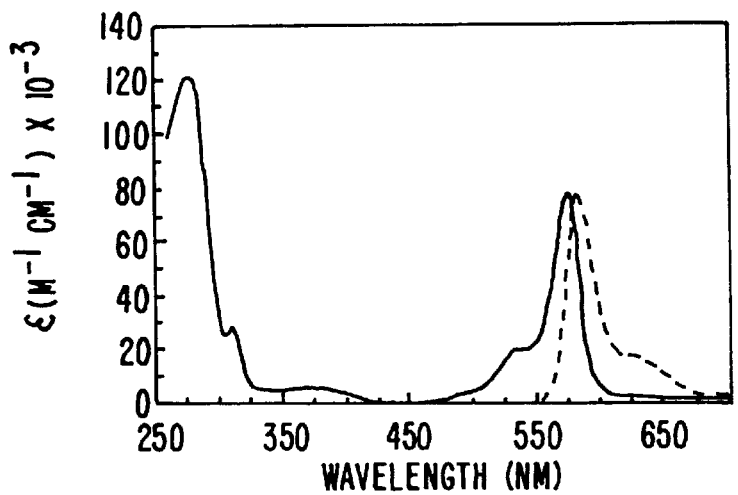
Figure 7C:
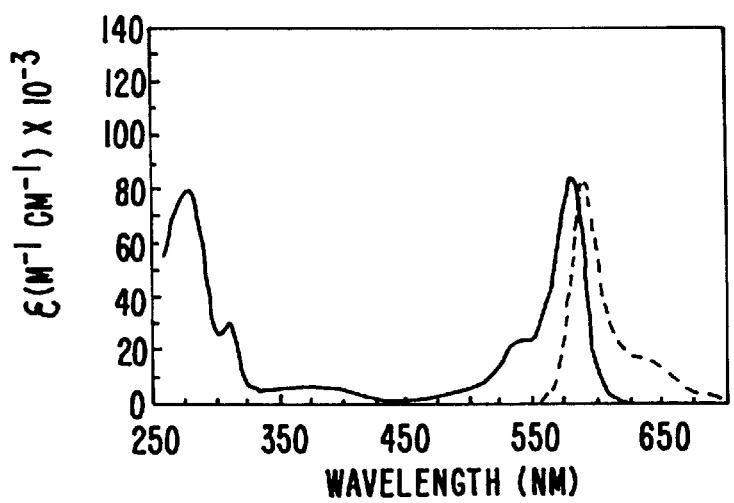

All three PEB adducts were strongly fluorescent (FIG. 7 and Table 3) and, although they exhibited slightly different absorption and emission maxima, they had very similar optical properties including narrow excitation and emission envelopes, mirror image symmetry between excitation and emission spectra, and small (i.e. 9–10 nm) Stoke's shifts. The fluorescence polarization spectrum of ASPHYA-PEB exhibited constant angular displacement of emission across the entire absorption envelope, indicating that the shoulder to the blue of the absorption maximum represented a vibrational sideband rather than a separate electronic transition (Lakowicz (1983) *Principles of Fluorescence Spectroscopy*. Pp 1–496, Plenum Press, New York). Phase-modulated fluorescence lifetime ($\tau_f$) measurements revealed that ASPHYA-PEB excited state decay best fit a Lorentzian distribution with one major component (92%) having a 1.82 nsec lifetime. This measurement compared favorably with the parallel analysis of B-phycoerythrin (B-PE) which also exhibited one major component (92%) with a 2.26 nsec lifetime. Taken together, these data show that a single PEB adduct is produced upon co-incubation of this bilin with apophytochrome, and that the PEB chromophore is rigidly bound to all three phytofluor proteins in a similar chemical environment and conformation.

Phytofluors are intensely fluorescent.

Using quantitative amino acid analysis, the molar absorption coefficient ($\epsilon_{PEB}$) for the ASPHYA-PEB monomer was estimated to be 113,000 M$^{-1}$ cm$^{-1}$ at 576 nm. Similar analyses performed with MCPHY1-PEB and N514PEB yielded slightly smaller $\epsilon\epsilon_{PEB}$ values, albeit larger than that of GFP (Table 1). Since these $\epsilon_{PEB}$ values were based on protein quantitation, they represent a "practical" molar absorption coefficient which underestimates the actual value if some fraction of the phytochrome molecules had not assembled with PEB. An alternative determination of the molar absorption coefficient of ASPHYA-PEB was made per bound PEB molecule by comparison of the ratio of visible (chromophore) absorbance maximum to UV (protein) absorbance maximum for native phytochrome, ASPHYA-P$\Phi$B and ASPHYA-PEB. This method relies on the assumptions that PEB assembles with recombinant apophytochrome to the same extent as P$\Phi$B, and that the molar absorption coefficients of the P$\Phi$B chromophore is identical for native and recombinant oat phytochrome A (i.e. 132,000 M$^{-1}$ cm$^{-1}$, Kelly et al. (1987) *In Vitro. Photochemistry and Photobiology*, 46: 5–13). Using this method, $\epsilon_{PEB}$ was estimated to be 165,000 M$^{-1}$ cm$^{-1}$ per PEB chromophore.

Fluorescence quantum yields ($\Phi\epsilon_f$) of the three phytofluors were determined relative to B-PE and fluorescein standards. The three phytofluors are intensely fluorescent, with values for $\Phi_f \geq 0.7$ (Table 1). By contrast, $\Phi_f$ for free PEB ranged from 0.003 to 0.008 depending upon pH (Table 1; data not shown). Phytofluor $\Phi_f$ was also independent of excitation wavelength (data not shown), thus confirming that a single fluorescent species was present in each phytofluor preparation. Since fluorescent quantum yield and lifetime are directly proportional, the $\Phi_f/\tau_f$ ratio could be directly compared for B-PE and ASPHYA-PEB, assuming that PEB has the same intrinsic lifetime when bound to both proteins. Using lifetimes determined from phase modulated fluorimetry (above) and $\Phi_f$=0.98 for B-PE Grabowski et al. (1978) *Photochem. Photobiol.* 28: 39–45), $\Phi_f$=0.78 was calculated for the ASPHYA-PEB. The error between measured and calculated values in this case is consistent with those accepted for relative quantum yield measurements.

The brightness of a fluorophore depends both on the quantity of light absorbed ($\epsilon$) and the fraction of that light which is emitted ($\Phi_f$), and thus determines its utility as a probe. Table 3 shows that brightness of the phytofluors compare favorably to other commonly used fluorescent probes. Since ASPHYA-PEB and MCPHY-PEB are homodimers, these phytofluors will be 2-fold brighter than the values listed in Table 1 which are based on the PHY-PEB monomer. Both the long wavelength emission of the phytofluors and the increased intrinsic brightness relative to GFP represent useful attributes of this new class of fluorophore. Phytofluors are pH- and photo-stable probes.

Figure 8A:
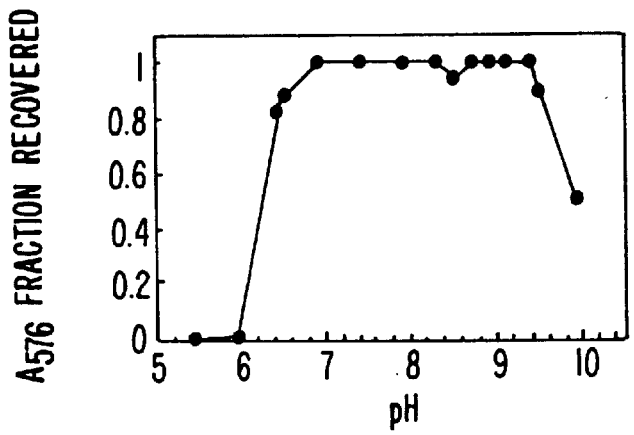
FIGS. 8A–C. pH-stability and photo-stability of the ASPHYA-PEB phytofluor. A) Relative recoveries of soluble ASPHYA-PEB (peak absorbance measured at 576 nm, following incubation at each pH, divided by peak absorbance at 576 nm for the pH 8.0 sample) are plotted against pH. B) Fluorescence quantum yields were calculated for samples incubated in buffers of various pH's relative to $\Phi_f$=0.70 for the pH 8.0 sample. C) Photostabilities of ASPHYA-PEB (circles, monitored at 576 nm), B-PE (squares, monitored at 546 nm) and fluorescein (diamonds, monitored at 491 nm) irradiated with white light (fluence rate of 400 M m$^{-2}$ sec$^{-2}$) are shown with open symbols. Closed symbols indicate measurements made on samples kept in darkness.
Figure 8B:
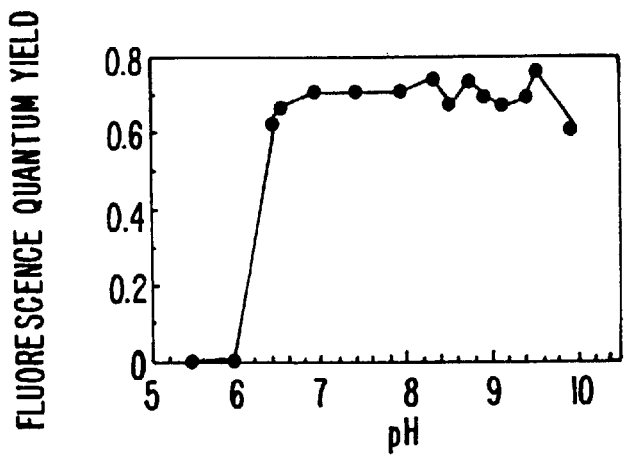

ASPHYA-PEB absorbance and fluorescence intensities were found to be quite stable from pH 6.5 to 9.5 (FIG. 8A and 8B). The peak shapes of absorbance and fluorescence spectra at each pH were also unperturbed (data not shown). By contrast, free PEB displayed variable absorption and fluorescence spectra in this pH range (Table 3; data not shown). These results indicate that the PEB fluorophore is shielded from interactions with the bulk solvent when bound within the chromophore pocket of apophytochrome. In this regard, phytofluors may be an ideal choice for applications requiring uniform detection in variable pH environments, as opposed to many small molecule fluorophores (Haugland (1996) *Handbook of Fluorescent Probes and Research Chemicals*, Molecular Probes, Eugene, Oreg.) and GFP (Ward et al. (1980) *Photochem. Photobiol.* 31: 611–615) which display pH-dependent fluorescence.

Figure 8C:
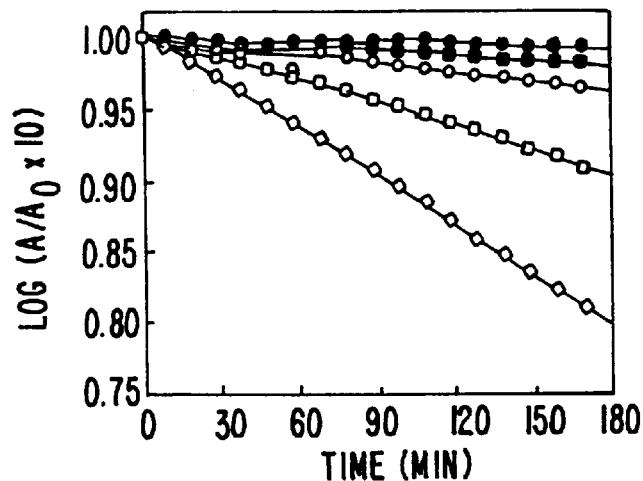

ASPHYA-PEB photostability under white light was compared to B-PE and fluorescein (FIG. 8C). These measurements indicated that photobleaching was log linear for all three fluorophores with rates of $2.0 \times 10^{-4}$ min$^{-1}$ for ASPHYA-PEB, $5.5 \times 10^{-4}$ min$^{-1}$ for B-PE, and $1.1 \times 10^{-3}$ min$^{-1}$ for fluorescein. When these rates were corrected for the quantity of photons absorbed, ASPHYA-PEB and B-PE manifested similar photostabilities, greater than 8-fold more photostable than fluorescein. Since B-PE has one of the lowest photodestruction quantum yields among the common probes (White (1987) *Analyt. Biochem.* 161: 442–452), these results suggest that the phytofluor family of fluorescent proteins will be an excellent addition to currently available fluorescent probes. The shielded environment of PEB when bound to apophytochrome suggests that phytofluors may be resistant to a number of potential quenching agents. Phytofluors can be reconstituted in plant cells.

To test the feasibility of reconstituting phytofluors in vivo, the hy1 mutant of *Arabidopsis thaliana* which is unable to synthesize PΦB, and accumulates apophytochrome A in the cytoplasm (Parks et al. (1989) *Plant Molecular Biol.* 12:425–437; Parks et al. (1991) *Plant Cell* 3: 1177–1186) was utilized. Upon incubation of dark-grown hy1 seedlings with PEB, a significant increase in orange fluorescence was observed. That this fluorescence emission represented in situ formation of the PEB adduct of apophytochrome A was established by confocal microscopy (FIG. 9). PEB-treated hy1 seedlings exhibited significant phytofluor emission between 590–610 nm primarily in the hypocotyls (FIG. 9 left (A)) with red (proto)chlorophyll emission (670–800 nm observed) mainly in the cotyledons (FIG. 9 right (A)). Phytofluor fluorescence was cytoplasmically localized, which contrasts with chlorophyll fluorescence, which was confined to the chloroplast organelle (FIG. 9 right (B)). Untreated control hy1 seedlings displayed no phytofluor emission, only the red emission.

By comparison with PEB treated hy1 seedlings, PEB-treated wild type seedlings displayed markedly reduced orange fluorescence which was exclusively seen in the hypocotyl hook region (FIG. 9 left (C)). The observed pattern of fluorescence labeling of PEB treated seedlings was fully consistent with the known accumulation of apophytochrome A in the hypocotyl hook of dark grown dicotyledonous seedlings. The PEB-dependent appearance of orange fluorescence in wild type seedlings supports the presence of newly translated apophytochrome A that has not yet assembled with endogenous PΦB. No phytofluor fluorescence was detected in PEB-treated seedlings of the hy1 phyA phyB triple mutant, that lacks apophytochromes A and B (FIG. 9D). Taken together, these data provide compelling precedent for phytofluor reconstitution in live cells.

The phytofluors of this invention possess the best attributes of both B-PE and GFP; including the ability to self assemble, the red-shifted emission, and their brightness (i.e. 3–6 fold brighter than GFP). Since PEB can be obtained in quantity by methanolysis of commercially available red algae, the use of phytofluors in vivo is limited only by the expression of apophytochrome and delivery PEB. This study, however establishes conditions for routine delivery of PEB to cells. In addition, this study has illustrated the expression of heterologous apophytochrome. The demonstration of this invention that fluorescent phytochromes can be reconstituted in living cells taken with the observation that (non-fluorescent) photoactive phytochromes can be reconstituted in living yeast cells (Li et al. (1994) *Proc. Natl. Acad. Sciences USA*, 91: 12535–12539) indicates that phytofluors can be routinely reconstituted in other organisms as well.

EXAMPLE 4

Cyanobacterial Phytochrome Two Component Light Sensory System

Identification of the rcaE gene from the cyanobacterium *Fremyella diplosiphon*, which encodes a protein that is structurally related to higher plant phytochromes and bacterial histidine kinases, has renewed interest in the possibility that phytochrome is a protein kinase (Kehoe and Grossman (1996) *Science* 273: 1409–1412). Other phytochrome-like open reading frames (orfs) have also been noted in the cyanobacterium Synechocystis sp. PCC6803 genome (Kehoe and Grossman (1996) supra., Kaneko et al. (1997) *DNA Res.* 3: 109–36; Allen and Matthijs (1997) *Tr. Plant Sci.* 2: 41–43). One of these orfs, locus slr0473, encodes a 748 residue polypeptide whose expression in *E. coli* and incubation with phycocyanobilin (PCB), yielded an adduct with a red, far-red photoreversible phytochrome signature (Hughes et al. (1997) *Nature* 386: 663). Closer inspection of this phytochrome locus, referred to herein as cph1 for cyanobacterial phytochrome 1, revealed another orf only 10 bp downstream, locus slr0474, that is named herein rcp1 for response regulator for Cph1 based on the following study (FIG. 10A). Since the C-terminal domain of Cph1 contains all conserved features of histidine kinase transmitter modules (FIG. 10B), and rcp1 encodes a 147 amino acid protein related to the CheY superfamily of bacterial response regulators (FIG. 10C), which contain aspartate kinase receiver modules, whether these proteins represent a functional light-regulated transmitter-receiver pair (Parkinson and Kofoid (1992) *Annu. Rev. Genet.* 26: 71–112) was investigated.

Affinity-tagged versions of both proteins were cloned by PCR and expressed in *E. coli*. Briefly, loci slr0473 and slr0474 were amplified by PCR using purified Synechocystis sp PCC6803 genomic DNA, both individually and as an operon, with primers which enabled their cloning into the pASK75B expression vector (Murphy and Lagarias (1997) *Photochem. Photobiol.*, 65: 750–758. Expression of Strep-Tagged fusions of Cph1 and Rcp1 in *E. coli* strain DH5 was performed according to manufacturer's instructions (Biometra Inc.)

Figure 11B:
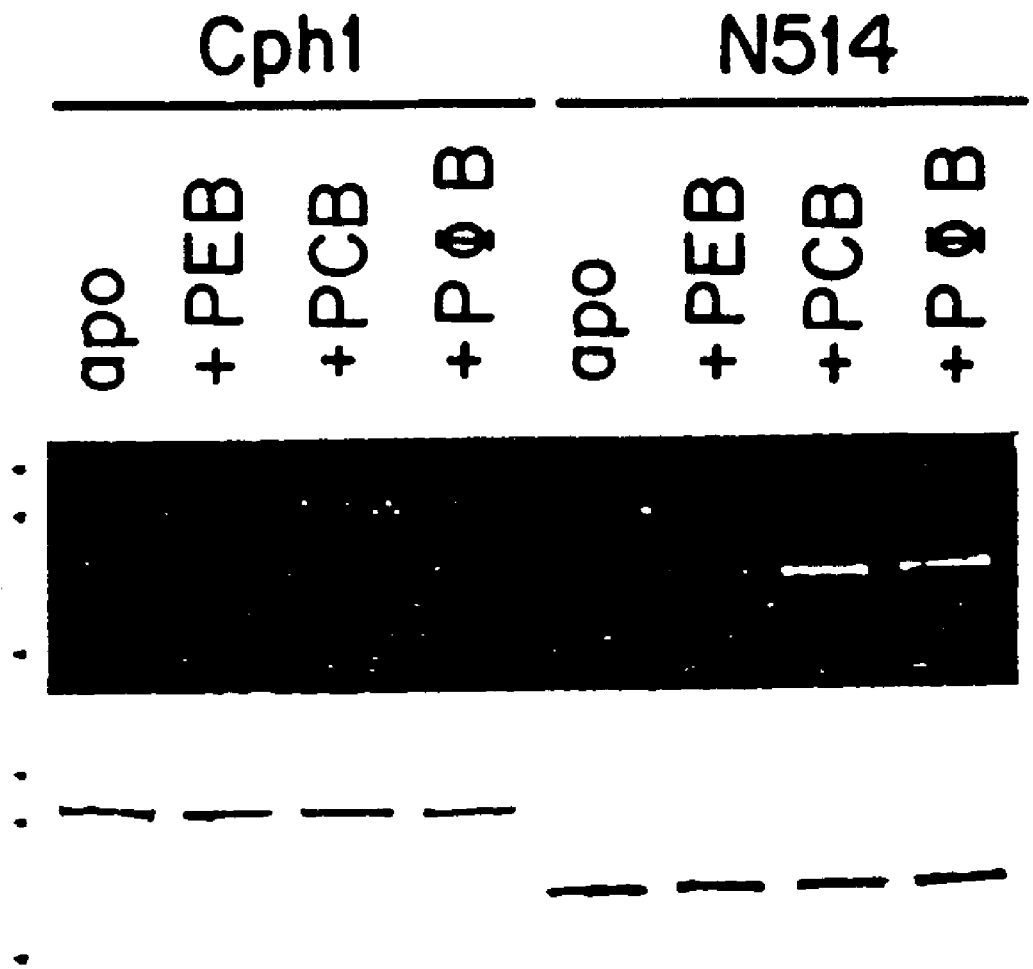

That Cph1 is a functional phytochrome homolog was demonstrated by its ability to catalyze its own chromophore attachment to yield photoreversible adducts with the higher plant chromophore precursor, phytochromobilin (PΦB), and its phycobilin analog PCB (FIG. 11A). Assembly with phycoerythrobilin (PEB), a phycobilin analog that lacks the C15 double bond found in PCB and PΦB, also produced a covalent adduct as visualized by zinc-blot analysis (FIG. 11B). The PEB adduct of Cph1 was photochemically inactive, thus demonstrating that photoisomerization of the C15 double bond is required for Cph1 photoactivity as for higher plant phytochromes (Li and Lagarias (1992) *J. Biol. Chem.* 267: 19204–19210).

A deletion mutant N514 was obtained by PCR of cph1 using primers "S6801phy" N514 Sal antisense primer 5'-GCGTCGACCACCTTCTTCTGCCTGGC GCAA-3' (SEQ ID NO: 15), and "S6801phy" sense primer 5'-GCACTAGTTAACGAGG GCAAAAAATGGCCACCACCGTAC-3' (SEQ ID NO: 16) designed to amplify the cph1 sequence coding for amino terminal residues 1–514. The PCR product was cloned into pASK75B and the Strep-Tagged fusion protein N514 was expressed in *E. coli* as described above.

The Cph1 deletion mutant N514 which lacks the transmitter domain also bound all three bilins covalently (FIG. 11B), yielding PΦB and PCB adducts with absorption difference spectra indistinguishable from the full-length photoreceptor. These data indicate that the N-terminal region of Cph1 delimits a functional photosensory domain (FIG. 11C) consistent with the structure and photochemistry of eukaryotic phytochromes (Furuya (1993) *Annu. Rev. Plant Physiol. Plant Mol. Biol.* 44: 617–645; Quail et. al. (1995) *Science* 268: 675–680; Pratt (1995) *Photochem. Photobiol.* 61: 10–21; Smith (1995) *Annu. Rev. Plant Physiol. Plant Mol. Biol.* 46: 289–315; Jones and Edgerton (1994) *Sem. Cell Biol.* 5: 295–302; Vierstra (1993), Plant Physiol., 103: 679–684).

Cph1 is smaller than eukaryotic phytochromes, lacking a 60–100 amino acid N-terminal fragment found on the photosensory domains of prototypical phytochromes and approximately half of the C-terminal region (FIG. 11C). Removal of the N-terminal portion of higher plant phytochromes blue-shifts its Pfr absorption maximum and attenuates its biological activity (Jones and Edgerton (1994) *Sem. Cell Biol.* 5: 295–302; Vierstra (1993), *Plant Physiol.*, 103: 679–684). Consistent with these observations, $P_{fr}$ absorption maxima of Cph1-bilin adducts are blue-shifted relative to higher plant phytochrome bilin adducts while Pr absorption maxima are similar (FIG. 11A). The dark reversion properties of the two bilin adducts of Cph1 are particularly interesting (FIG. 11D). PCB adducts of Cph1 and N514 deletion mutant display little dark reversion, while PΦB adducts show considerable dark reversion, with respective half lives of 10 and 24 h. In addition to demonstrating that $P_{fr}$ stability depends upon chromophore structure, these results indicate that the transmitter domain influences the conformational stability of the chromophore domain. In view of the potential role of dark reversion in the perception of photoperiod (Borthwick and Hendricks (1960) *Science* 132: 1223–1228) and light direction (Iino et al. (1997) *Photochem. Photobiol.* 65: 10320–1038), the identity of the natural Cph1 chromophore is of great interest.

To test whether Cph1 and Rcp1 represent functional transmitter and receiver molecules, affinity-tagged versions of Cph1 and Rcp1 fusion proteins were purified and the PCB adduct of Cph1 was analyzed for protein kinase activity (FIG. 3A). Briefly, maltose binding protein (MBP) fusions with Strep-Tagged WT and D68A mutant of Rcp1, generated by site-specific mutagenesis (Picard et al. (1994) *Nucleic Acid Res.*, 22: 2587–2591), were obtained by subcloning into the BamH1 site of pMAL-c2, expressed in *E. coli* and purified according to the vector manufacturer's instructions (New England BioLabs). Strep-Tagged Cph1 was produced by PCR amplification of loci slr0473 and slr0474 using purified Synechocystis sp PCC6803 genomic DNA, both individually and as an operon, with primers which enabled their cloning into the pASK75B expression vector (Murphy and Lagarias (1997) *Photochem. Photobiol.* 65: 750–758). Expression of Strep-Tagged fusions of Cph1 and Rcp1 in *E. coli* strain DH5 was performed according to manufacturer's instructions (Biometra Inc.). The N514 mutant was produced as described above. Both Strep-Tagged Cph1 and the N514 mutant were purified with a homemade streptavidin-sepharose matrix (Schmidt and Skerra (1994) *J. Chromatog.* 676: 337–345).

Surprisingly, the Pr form of Cph1 exhibited ATP-dependent autophosphorylation activity, whereas phosphorylation of the Pfr form was greatly reduced. Consistent with a histidine residue as the phosphorylation site, Cph1 autophosphorylation was base stable and acid labile. Similar experiments performed with the N514 mutant demonstrated that the transmitter domain was required for Cph1 autophosphorylation (FIG. 12A). That Rcp1 is a functional receiver substrate for Cph1 was established by phosphotransfer from Cph1 to Rcp1. No phosphotransfer occurred with the D68A mutant of Rcp1 which lacks the conserved phosphate-accepting aspartate residue of receiver domains (Parkinson and Kofoid (1992) *Annu. Rev. Genet.* 26: 71–112). The inability of the H538K mutant of Cph1 to autophosphorylate and to support phosphotransfer to Rcp I demonstrated that this conserved histidine residue in the Cph1 transmitter module is required for both activities. These data, taken together, demonstrate that Cph1 is a histidine kinase that mediates light-dependent phosphotransfer to Rcp1. Cph1 and Rcp1 thus represent a two-component regulatory system in cyanobacteria that is modulated by red and far-red light.

The low amount of Cph1 autophosphorylation and Rcp1 phosphotransferase activity exhibited by the Pfr sample probably represents the presence of residual Pr and is consistent with the photoequilibrium mixture, containing 13% Pr, which results for higher plant phytochromes irradiated with saturating red light (Furuya (1993) *Annu. Rev. Plant Physiol. Plant Mol. Biol.* 44: 617–645; Quail et. al. (1995) *Science* 268: 675–680; Pratt (1995) *Photochem. Photobiol.* 61: 10–21; Smith (1995) *Annu. Rev. Plant Physiol. Plant Mol. Biol.* 46: 289–315). To determine whether phosphorylated Pfr (Pfr*) was capable of phosphate transfer to Rcp1, Pr was autophosphorylated (Pr*), photoconverted to Pfr* and then incubated with Rcp1. By comparison with a control sample maintained in the Pr* form, phosphotransfer from Pfr* to Rcp1 was clearly prevented. Thus, the Pfr form of Cph1 lacks both autophosphorylation and Rcp 1 phosphotransfer activities.

The organization of the cyanobacterial phytochrome operon is similar to the *Fremyella diplosiphon rcaEF* operon which encodes two elements of the complementary chromatic adaptation signal transduction pathway (Kehoe and Grossman (1996) *Science* 273: 1409–1412; Kehoe and Grossman (1997) *J. Bacteriol.* 179, 3914–3921). This and the biochemical data suggest that the molecular mechanism of Cph1 action involves light-regulated protein phosphorylation-dephosphorylation. In this model, Cph1 can exist as four species—Pr, Pr*, Pfr and Pfr*, whose abundances are regulated both by light conditions and by Rcp1 phosphorylation status. By analogy to the multistep phosphorelay cascades proposed for complementary chromatic adaptation in *Fremyella diplosiphon* (Kehoe and Grossman (1997) *J. Bacteriol.* 179, 3914–3921), sporulation in *Bacillus subtilus* (Perego et al. (1994) *Cell* 79: 1047–1055) and osmosensing in yeast (Posaset et al. (1996) *Cell* 86: 865–875), Rcp1 dephosphorylation could be mediated by phosphotransfer to another regulatory molecule. Alternatively, the two forms of the small receiver molecule, Rcp1 and phospho-Rcp1 (Rcp1*), could have distinct regulatory activities like CheY (Parkinson and Kofoid (1992) *Annu. Rev. Genet.* 26: 71–112).

In higher plants, Pfr is thought to be the active form of phytochrome. The present examples suggest that the light signal transduced by Cph1 involves the regulation of Pr abundance, rather than that of $P_{fr}$. However, Pfr (or Pfr*) could perform an as yet unidentified role in the signal transduction process, such as allosterically regulating the activity of an Rcp 1 phosphatase or influencing phosphotransfer to another regulatory molecule. In view of the evidence presented here, the presence of a transmitter-like domain in higher plant phytochromes (Schneider et al. (1991) *FEBS Lett.* 281: 245–249) and the observed protein kinase activity of purified higher plant phytochromes (Wong et al. (1986) *J. Biol. Chem.* 261: 12089–12097; Wong et al. (1989) *Plant Physiol.* 91: 709–718), it is expected that the molecular mechanism of phytochrome function in plants will involve phosphorylation/dephosphorylation of transmitter- and receiver-containing signaling proteins like those prevalent in eubacteria and archaebacteria It is intriguing that two component regulatory family members have been identified in plants including the putative plant hormone receptors for ethylene (Chang et al. (1993) *Science* 262: 539–544 (1993)), and cytokinin (Kakimoto (1996) *Science* 274: 982–985). The physiological interplay between light and hormone responses in plants (Chory et al. (1996) *Proc. Natl. Acad. Sci. (USA)* 93: 12066–12071) suggests that these receptors may be targets for integrated transduction of multiple signals.

EXAMPLE 5

An Affinity Tagged Phytofluor Bound to a Solid Support

This example describes the visual observation of orange fluorescence from Strep-Tagged phytofluors adsorbed to a streptavidin-agarose matrix. The fusion of the Strep-Tag to the C-terminus of the apoprotein confers the ability of the fluorescent phytofluor probe to bind with high affinity to an immobilized streptavidin polypeptide.

Recombinant Strep-Tagged ASPHYA, MCPHY 1, and N5 14 apoproteins were expressed and partially purified by ammonium sulfate fractionation as described (Murphy and Lagarias (1997) *Photochem. Photobiol.*, 65: 750–758; Wu and Lagarias (1996) *Proc. Natl. Acad. Sci., USA*, 93: 8989–8994). The crude apoprotein preparations were resuspended in buffer W (100 mM Tris-HCl pH 8.0, 1 mM EDTA, 1 mM PMSF, 1 mM DTT) and incubated with 5 μM PEB at room temperature for 60 min. In a 4° C. cold room under green safelight, these preparations were applied to a 3 ml (bed volume) streptavidin-agarose column of dimensions 1.3 cm diameter×5 cm length. The orange phytofluor fluorescence, originally faintly visible in the liquid fraction, was strongly retained and concentrated onto the streptavidin-agarose matrix as the liquid phase passed through. Extensive washing of the streptavidin-agarose matrix with 40 ml of buffer W failed to appreciably desorb this orange emitting species as monitored visually. The orange fluorescent species could be nearly quantitatively and specifically eluted from the streptavidin-agarose matrix with 3 mM diaminobiotin in buffer W which binds to streptavidin competitively with the 10 amino acid Strep-Tag at the C-terminus of the phytofluor. Spectroscopic and SDS-PAGE analyses of the eluted fractions indicated that the orange fluorescence was associated with the phytofluor protein.

This experiment indicates that phytofluors can strongly and specifically interact with (e.g., bind to) other macromolecular complexes via covalent attachment of an affinity tag at the C-terminus of the phytochrome apoprotein. Biotin avidin linkages are widely used as conjugates to all manner of moieties (e.g, nucleic acids, proteins, antibodies, etc.). This experiment indicates that the phytofluors of this invention can be routinely used to label a wide variety of macroscopic or molecular moieties using currently available (strept)avidin-biotin technology.

EXAMPLE 6

Modifications of Apoprotein Structure

This example describes the ability to modify phytochrome apoproteins by deletion of portions of the polypeptide or by fusion of other proteins to the apoprotein C-terminus by gene fusions. In all cases described, phytochromes retain the ability to covalently assemble chromophore to create a fully active chromophore domain.

Removal of the C-termini from a number of phytochromes has yielded monomeric proteins which autocatalytically assemble with PΦB in vitro to create adducts which are spectrophotometrically indistinguishable from the full length phytochromes (Cherry et al. (1993) *Plant Cell*, 5: 565–575; Lagarias et al. (1997) *Plant Cell*, 9, 675–788; Terry et al. (1993) *Arch. Biochem. Biophys.* 306: 1–15). Apoprotein deletion mutants consisting of the first 599 residues of Arabidopsis phytochrome A (ATPHYA) and the first 514 residues from Synechocystis sp PC6803 phytochrome (N514) have been expressed in micro-organisms and assembled with PEB thereby forming fluorescent phytofluors. The N514 mutant was shown to be monomeric by gel filtration chromatography, and ATPHYA is also believed to be monomeric by analogy to previously described deletions (Cherry et al. (1993) *Plant Cell*, 5: 565–575; Lagarias et al. (1997) *Plant Cell*, 9, 675–788; Terry et al (1993) *Arch. Biochem. Biophys.* 306: 1–15).

The phytochrome protein is able to retain photoreceptor activity when additions are made by expression of in frame gene fusions. Hygromycin phosphotransferase has been fused to the C-terminus of Arabidopsis phytochrome A (ATPHYA) to create a 165 kDa fusion protein which has fall photoreceptor activity and full hygromycin phosphotransferase activity (Yeh and Lagarias (1997) *Plant Biol., Abstract* 591, *Plant Physiol.* 114(3): 304 1997). A number of phytochromes have been affinity purified via carboxyterminal fused 6 histidine tags (Hughes et al. (1997) *Nature* 386: 663–663) or 15 amino acid linker-Strep-tags (Murphy and Lagarias (1997) *Photochem. Photobiol.*, 65: 750–758; Wu and Lagarias (1996) *Proc. Natl. Acad. Sci., USA*, 93: 8989–8994). In all cases, the peptide retains the ability to interact with affinity matrices and a spectrophotometrically intact photoreceptor is produced upon assembly with chromophore precursors. In related experiments, a number of deletions and fill length phytochromes from *Avena sativa* (Oat), *Arabidopsis thaliana, Mesotaenium caldariorum* (green algae), and Synechocystis sp PC6803 (cyanobacteria), all of which contain a C-terminal Strep-tag, have been assembled with PEB and shown to fluoresce.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

SEQUENCE LISTING

---

What is claimed is:

1. A composition comprising a moiety to be detected linked to a fluorescent adduct consisting of a phytochrome apoprotein and a bilin chromophore, wherein the fluorescent adduct is useful for detecting the presence of the moiety in a sample.

2. The composition of claim 1, wherein said apoprotein is selected from the group consisting of a plant apoprotein, an algal apoprotein, and a cyanobacterial apoprotein.

3. The composition of claim 2, wherein said apoprotein is an oat apoprotein.

4. The composition of claim 1, wherein said apoprotein consists of a chromophore domain.

5. The composition of claim 4, wherein said chromophore domain consists of the 514 N-terminal amino acids of said apoprotein.

6. The composition of claim 1, wherein said bilin is a tetrapyrrole.

7. The composition of claim 1, wherein said bilin is phycoerythrobilin.

8. The composition of claim 1, wherein said moiety is a biomolecule.

9. The composition of claim 8, wherein said biomolecule is selected from the group consisting of a protein, a glycoprotein, an antibody, and a nucleic acid.

10. The composition of claim 8, wherein said biomolecule is a nucleic acid.

11. The composition of claim 8, wherein the biomolecule is a protein.

12. The composition of claim 1, wherein said apoprotein is an oat apoprotein and said bilin chromophore is phycoerythrobilin.

13. A method of detecting the presence of a biomolecule in a sample, the method comprising:

providing a sample comprising a biomolecule linked to a fluorescent adduct consisting of a phytochrome apoprotein and a bilin chromophore;

contacting the sample with light which causes the fluorescent adduct to emit light;

detecting the emitted light, thereby detecting the presence of the biomolecule.

14. The method of claim 13, wherein the step of contacting the sample with light includes contacting the sample with light having a wavelength of about 570 nm.

15. The method of claim 13, wherein the step of detecting the emitted light includes detecting light having a wavelength of about 590 nm.

16. The method of claim 13, wherein said apoprotein is selected from the group consisting of a plant apoprotein, an algal apoprotein, and a cyanobacterial apoprotein.

17. The method of claim 16, wherein said apoprotein is an oat apoprotein.

18. The method of claim 13, wherein said apoprotein has about 1100 amino acid residues.

19. The method of claim 18, wherein said apoprotein consists of a chromophore domain.

20. The method of claim 19, wherein said chromophore domain consists of the 514 N-terminal amino acids said apoprotein.

21. The method of claim 13, wherein said bilin is tetrapyrrole.

22. The method of claim 13, wherein said bilin is phycoerythrobilin.

23. The method of claim 13, wherein said moiety is a biomolecule.

24. The method of claim 23, wherein said biomolecule is selected from the group consisting of a protein, a glycoprotein, an antibody, and a nucleic acid.

25. The method of claim 23, wherein said biomolecule is a nucleic acid.

26. The method of claim 23, wherein the biomolecule is a protein.

27. The method of claim 13, wherein said apoprotein is an oat apoprotein and said bilin chromophore is phycoerythrobilin.

* * * * *

SEQUENCE LISTING

```
<160> NUMBER OF SEQ ID NOS: 16

<210> SEQ ID NO 1
<211> LENGTH: 554
<212> TYPE: PRT
<213> ORGANISM: Artificial Sequence
<220> FEATURE:
<223> OTHER INFORMATION: Description of Artificial Sequence::  Sequence
      alignment Fig. 6 Consensus

<400> SEQUENCE: 1

Met Ser Ser Ser Arg Pro Ser Gln Ser Ser Gly Gly Ser Lys Ser Arg
 1               5                  10                  15
```

-continued

```
Ile Ile Ala Gln Thr Thr Asp Ala Lys Leu His Ala Val Phe Ala Ala
             20                  25                  30

Ser Gly Asp Ser Phe Asp Tyr Ser Lys Ser Val Arg Ala Thr Thr Glu
         35                  40                  45

Pro Glu Lys Val Thr Ala Tyr Leu Gln Arg Ile Gln Arg Gly Gly Leu
     50                  55                  60

Ile Gln Pro Phe Gly Cys Leu Leu Ala Val Asp Glu Lys Ser Phe Arg
 65                  70                  75                  80

Val Ile Ala Tyr Ser Glu Asn Ala Pro Glu Met Leu Thr Leu Val Ser
                 85                  90                  95

His Ala Val Pro Ser Val Gly Pro Val Leu Gly Ile Gly Thr Asp Val
             100                 105                 110

Arg Thr Leu Phe Thr Ala Pro Ser Ala Ala Leu Glu Lys Ala Leu
         115                 120                 125

Gly Phe Gly Asp Ser Leu Leu Asn Pro Ile Leu Val His Cys Lys Thr
 130                 135                 140

Ser Gly Lys Pro Phe Tyr Ala Ile Leu His Arg Val Asp Gly Gly Leu
145                 150                 155                 160

Val Ile Asp Glu Pro Val Lys Pro Tyr Asp Pro Thr Ala Ala Gly Ala
                 165                 170                 175

Leu Gln Ser Tyr Lys Leu Ala Ala Lys Ala Ile Ser Arg Leu Gln Ser
             180                 185                 190

Leu Pro Gly Gly Met Glu Leu Leu Cys Asp Thr Val Val Glu Glu Val
         195                 200                 205

Arg Glu Leu Thr Gly Tyr Asp Arg Val Met Ala Tyr Lys Phe His Glu
     210                 215                 220

Asp Glu His Gly Glu Val Val Ala Glu Ile Arg Pro Asp Leu Glu Pro
225                 230                 235                 240

Tyr Leu Gly Leu His Tyr Pro Ala Thr Asp Ile Pro Gln Ala Ala Arg
                 245                 250                 255

Phe Leu Phe Met Lys Asn Val Arg Met Ile Cys Asp Cys Arg Ala Pro
             260                 265                 270

Val Lys Val Ile Gln Asp Glu Lys Leu Pro Gln Pro Leu Ser Leu Cys
         275                 280                 285

Gly Ser Thr Leu Arg Ala Pro His Gly Cys His Leu Gln Tyr Met Ala
     290                 295                 300

Asn Met Gly Ser Ile Ala Ser Leu Val Met Ala Val Ile Asn Asp Asn
305                 310                 315                 320

Glu Glu Asp Glu Gly Gln Lys Lys Arg Leu Trp Gly Leu Val Val Cys
                 325                 330                 335

His His Thr Ser Pro Arg Phe Val Pro Phe Pro Leu Arg Tyr Ala Cys
             340                 345                 350

Glu Phe Leu Met Gln Val Phe Gly Leu Gln Leu Asn Met Glu Leu Glu
         355                 360                 365

Leu Glu Ser Gln Leu Arg Ala Lys Asn Ile Leu Arg Thr Gln Thr Leu
     370                 375                 380

Leu Cys Asp Met Leu Leu Arg Asp Ala Pro Leu Gly Ile Val Ser Gln
385                 390                 395                 400

Ser Pro Asn Ile Met Asp Leu Val Lys Cys Asp Gly Ala Ala Leu Leu
                 405                 410                 415

Tyr Gly Gly Lys Trp Leu Leu Gly Val Thr Pro Thr Glu Ser Gln Ile
             420                 425                 430

Lys Asp Ile Ala Glu Trp Leu Leu Glu Tyr His Gly Asp Ser Thr Gly
```

-continued

```
                435                 440                 445
Leu Ser Thr Asp Ser Leu Ala Asp Ala Gly Tyr Pro Gly Ala Ala Ala
    450                 455                 460

Leu Gly Asp Ala Val Cys Gly Met Ala Ala Lys Ile Thr Ser Lys
465                 470                 475                 480

Asp Phe Leu Phe Trp Phe Arg Ser His Thr Ala Lys Glu Ile Lys Trp
                485                 490                 495

Gly Gly Ala Lys His Asp Pro Asp Lys Asp Gly Arg Arg Met His
                500                 505                 510

Pro Arg Ser Ser Phe Lys Ala Phe Leu Glu Val Val Lys Arg Ser Leu
                515                 520                 525

Pro Trp Glu Asp Tyr Glu Met Asp Ala Ile His Ser Leu Gln Leu Ile
530                 535                 540

Leu Arg Gly Ser Phe Lys Asp Thr Cys Ile
545                 550
```

<210> SEQ ID NO 2
<211> LENGTH: 600
<212> TYPE: PRT
<213> ORGANISM: Artificial Sequence
<220> FEATURE:
<223> OTHER INFORMATION: Description of Artificial Sequence:  Sequence
    alignment Fig. 6 Asphya

<400> SEQUENCE: 2

```
Met Ser Ser Ser Arg Pro Ala Ser Ser Ser Ser Arg Asn Arg Gln
1               5                   10                  15

Ser Ser Gln Ala Arg Val Leu Ala Gln Thr Thr Leu Asp Ala Glu Leu
                20                  25                  30

Asn Ala Glu Tyr Glu Glu Ser Gly Asp Ser Phe Asp Tyr Ser Lys Leu
            35                  40                  45

Val Glu Ala Gln Arg Asp Gly Pro Pro Val Gln Gln Gly Arg Ser Glu
        50                  55                  60

Lys Val Ile Ala Tyr Leu Gln His Ile Gln Lys Gly Lys Leu Ile Gln
65              70                  75                  80

Thr Phe Gly Cys Leu Leu Ala Leu Asp Glu Lys Ser Phe Asn Val Ile
                85                  90                  95

Ala Phe Ser Glu Asn Ala Pro Glu Met Leu Thr Thr Val Ser His Ala
            100                 105                 110

Val Pro Ser Val Asp Asp Pro Arg Leu Gly Ile Gly Thr Asn Val
        115                 120                 125

Arg Ser Leu Phe Ser Asp Gln Gly Ala Thr Ala Leu His Lys Ala Leu
    130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                165                 170                 175

Leu Val Val Asp Phe Glu Pro Val Lys Pro Thr Glu Phe Pro Ala Thr
            180                 185                 190

Ala Ala Gly Ala Leu Gln Ser Tyr Lys Leu Ala Ala Lys Ala Ile Ser
        195                 200                 205

Lys Ile Gln Ser Leu Pro Gly Gly Ser Met Glu Val Leu Cys Asn Thr
    210                 215                 220

Val Val Lys Glu Val Phe Asp Leu Thr Gly Tyr Asp Arg Val Met Ala
225                 230                 235                 240
```

Tyr Lys Phe His Glu Asp Asp His Gly Glu Val Phe Ser Glu Ile Thr
              245                 250                 255

Lys Pro Gly Leu Glu Pro Tyr Leu Gly Leu His Tyr Pro Ala Thr Asp
          260                 265                 270

Ile Pro Gln Ala Ala Arg Leu Leu Phe Met Lys Asn Lys Val Arg Met
      275                 280                 285

Ile Cys Asp Cys Arg Ala Arg Ser Ile Lys Val Ile Glu Ala Glu Ala
  290                 295                 300

Leu Pro Phe Asp Ile Ser Leu Cys Gly Ser Ala Leu Arg Ala Pro His
305                 310                 315                 320

Ser Cys His Leu Gln Tyr Met Glu Asn Met Asn Ser Ile Ala Ser Leu
              325                 330                 335

Val Met Ala Val Val Asn Glu Asn Glu Glu Asp Asp Glu Ala Glu
          340                 345                 350

Ser Glu Gln Pro Ala Gln Gln Lys Lys Lys Leu Trp Gly Leu
      355                 360                 365

Leu Val Cys His His Glu Ser Pro Arg Tyr Val Pro Phe Pro Leu Arg
  370                 375                 380

Tyr Ala Cys Glu Phe Leu Ala Gln Val Phe Ala Val His Val Asn Arg
385                 390                 395                 400

Glu Phe Glu Leu Glu Lys Gln Leu Arg Glu Lys Asn Ile Leu Lys Met
              405                 410                 415

Gln Thr Met Leu Ser Asp Met Leu Phe Arg Glu Ala Ser Pro Leu Thr
          420                 425                 430

Ile Val Ser Gly Thr Pro Asn Ile Met Asp Leu Val Lys Cys Asp Gly
      435                 440                 445

Ala Ala Leu Leu Tyr Gly Gly Lys Val Trp Arg Leu Arg Asn Ala Pro
  450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
              485                 490                 495

Pro Gly Ala Ala Ala Leu Gly Asp Met Ile Cys Gly Met Ala Val Ala
          500                 505                 510

Lys Ile Asn Ser Lys Asp Ile Leu Phe Trp Phe Arg Ser His Thr Ala
      515                 520                 525

Ala Glu Ile Arg Trp Gly Gly Ala Lys Asn Asp Pro Ser Asp Met Asp
  530                 535                 540

Asp Ser Arg Arg Met His Pro Arg Leu Ser Phe Lys Ala Phe Leu Glu
545                 550                 555                 560

Val Val Lys Met Lys Ser Leu Pro Trp Ser Asp Tyr Glu Met Asp Ala
              565                 570                 575

Ile His Ser Leu Gln Leu Ile Leu Arg Gly Thr Leu Asn Asp Ala Ser
          580                 585                 590

Lys Pro Lys Arg Glu Ala Ser Leu
      595                 600

<210> SEQ ID NO 3
<211> LENGTH: 600
<212> TYPE: PRT
<213> ORGANISM: Artificial Sequence
<220> FEATURE:
<223> OTHER INFORMATION: Description of Artificial Sequence:: Sequence
      alignment Fig. 6 Atphya

<400> SEQUENCE: 3

-continued

```
Met Ser Gly Ser Arg Pro Thr Gln Ser Ser Glu Gly Ser Arg Arg Ser
 1               5                  10                 15

Arg His Ser Ala Arg Ile Ile Ala Gln Thr Thr Val Asp Ala Lys Leu
             20                  25                 30

His Ala Asp Phe Glu Glu Ser Gly Ser Ser Phe Asp Tyr Ser Thr Ser
             35                  40                 45

Val Arg Val Thr Gly Pro Val Val Glu Asn Gln Pro Pro Arg Ser Asp
         50                  55                 60

Lys Val Thr Thr Thr Tyr Leu His His Ile Gln Lys Gly Lys Leu Ile
 65                  70                  75                 80

Gln Pro Phe Gly Cys Leu Leu Ala Leu Asp Glu Lys Thr Phe Lys Val
                 85                  90                 95

Ile Ala Tyr Ser Glu Asn Ala Ser Glu Leu Leu Thr Met Ala Ser His
            100                 105                110

Ala Val Pro Ser Val Gly Glu His Pro Val Leu Gly Ile Gly Thr Asp
            115                 120                 125

Ile Arg Ser Leu Phe Thr Ala Pro Ser Ala Ser Leu Gln Lys Ala
            130                 135                 140

Leu Gly Phe Gly Asp Val Ser Leu Leu Asn Pro Ile Leu Val His Cys
145                 150                 155                 160

Arg Thr Ser Ala Lys Pro Phe Tyr Ala Ile Ile His Arg Val Thr Gly
                165                 170                 175

Ser Ile Ile Ile Asp Phe Glu Pro Val Lys Pro Tyr Glu Val Pro Met
            180                 185                 190

Thr Ala Ala Gly Ala Leu Gln Ser Tyr Lys Leu Ala Ala Lys Ala Ile
            195                 200                 205

Thr Arg Leu Gln Ser Leu Pro Ser Gly Ser Met Glu Arg Leu Cys Asp
    210                 215                 220

Thr Met Val Gln Glu Val Phe Glu Leu Thr Gly Tyr Asp Arg Val Met
225                 230                 235                 240

Ala Tyr Lys Phe His Glu Asp Asp His Gly Glu Val Val Ser Glu Val
                245                 250                 255

Thr Lys Pro Gly Leu Glu Pro Tyr Leu Gly Leu His Tyr Pro Ala Thr
            260                 265                 270

Asp Ile Pro Gln Ala Ala Arg Phe Leu Phe Met Lys Asn Lys Val Arg
    275                 280                 285

Met Ile Val Asp Cys Asn Ala Lys His Ala Arg Val Leu Gln Asp Glu
    290                 295                 300

Lys Leu Ser Phe Asp Leu Thr Leu Cys Gly Ser Thr Leu Arg Ala Pro
305                 310                 315                 320

His Ser Cys His Leu Gln Tyr Met Ala Asn Met Asp Ser Ile Ala Ser
                325                 330                 335

Leu Val Met Ala Val Val Asn Glu Glu Asp Gly Glu Gly Asp Ala
            340                 345                 350

Pro Asp Ala Thr Thr Gln Pro Gln Lys Arg Lys Arg Leu Trp Gly Leu
            355                 360                 365

Val Val Cys His Asn Thr Thr Pro Arg Phe Val Pro Phe Pro Leu Arg
    370                 375                 380

Tyr Ala Cys Glu Phe Leu Ala Gln Val Phe Ala Ile His Val Asn Lys
385                 390                 395                 400

Glu Val Glu Leu Asp Asn Gln Met Val Glu Lys Asn Ile Leu Arg Thr
                405                 410                 415
```

-continued

```
Gln Thr Leu Leu Cys Asp Met Leu Met Arg Asp Ala Pro Leu Gly Ile
            420                 425                 430

Val Ser Gln Ser Pro Asn Ile Met Asp Leu Val Lys Cys Asp Gly Ala
        435                 440                 445

Ala Leu Leu Tyr Lys Asp Lys Ile Trp Lys Leu Gly Thr Thr Pro Ser
    450                 455                 460

Glu Phe His Leu Gln Glu Ile Ala Ser Trp Leu Cys Glu Tyr His Met
465                 470                 475                 480

Asp Ser Thr Gly Leu Ser Thr Asp Ser Leu His Asp Ala Gly Phe Pro
                485                 490                 495

Arg Ala Leu Ser Leu Gly Asp Ser Val Cys Gly Met Ala Ala Val Arg
            500                 505                 510

Ile Ser Ser Lys Asp Met Ile Phe Trp Phe Arg Ser His Thr Ala Gly
        515                 520                 525

Glu Val Arg Trp Gly Gly Ala Lys His Asp Pro Asp Arg Asp Asp
    530                 535                 540

Ala Arg Arg Met His Pro Arg Ser Ser Phe Lys Ala Phe Leu Glu Val
545                 550                 555                 560

Val Lys Thr Arg Ser Leu Pro Trp Lys Asp Tyr Glu Met Asp Ala Ile
                565                 570                 575

His Ser Leu Gln Leu Ile Leu Arg Asn Ala Phe Lys Asp Ser Glu Thr
            580                 585                 590

Thr Asp Val Asn Thr Lys Val Ile
        595                 600

<210> SEQ ID NO 4
<211> LENGTH: 611
<212> TYPE: PRT
<213> ORGANISM: Artificial Sequence
<220> FEATURE:
<223> OTHER INFORMATION: Description of Artificial Sequence::  Sequence
      alignment Fig. 6 Mcphy1b

<400> SEQUENCE: 4

Met Ser Thr Ser Arg Met Ser Gln Ser Ser Gly Glu Ser Thr Ala Lys
 1               5                  10                  15

Thr Lys Arg Glu Val Arg Val Ala Gln Ala Thr Ala Asp Ala Lys Leu
            20                  25                  30

Asn Thr Ala Phe Glu Ala Ser Ala Ala Val Gly Gly Ser Phe Asp Tyr
        35                  40                  45

Thr Lys Ser Val Gly Ala Ser Leu Asn Ala Gly Ser Glu Ala Ile Pro
    50                  55                  60

Ser Ser Ala Val Thr Ala Tyr Leu Gln Arg Met Gln Arg Gly Gly Ile
65                  70                  75                  80

Thr Gln Thr Phe Gly Cys Met Leu Met Val Glu Glu Gly Ser Phe Arg
                85                  90                  95

Val Arg Ala Phe Ser Glu Asn Ala Gly Glu Met Leu Asp Leu Val Pro
            100                 105                 110

Gln Ala Val Pro Ser Met Gly Gln Gln Ser Leu Ile Ala Val Gly Thr
        115                 120                 125

Asp Ile Arg Thr Leu Phe Thr Ser Ala Ser Val Ser Leu Leu Glu Lys
    130                 135                 140

Ala Ala Met Ala Thr Asp Val Ser Val Met Asn Pro Val Ser Leu Gln
145                 150                 155                 160

Ser Arg Ala Ala Lys Lys Pro Phe Phe Ala Val Leu His Arg Ile Asp
                165                 170                 175
```

```
Val Gly Leu Val Val Asp Leu Glu Pro Val Arg Pro Ser Asp Pro Asn
            180                 185                 190

Val Ser Ala Ala Gly Ala Met Gln Ser His Lys Leu Ala Ala Lys Ala
            195                 200                 205

Ile Ser Arg Leu Gln Ser Leu Pro Gly Gly Asp Ile Gly Leu Leu Cys
            210                 215                 220

Asp Ala Val Val Glu Glu Val Arg Glu Leu Thr Gly Tyr Asp Arg Val
225                 230                 235                 240

Met Ala Tyr Lys Phe His Glu Asp Glu His Gly Glu Val Ile Ala Glu
                245                 250                 255

Ile Arg Arg Ser Asp Leu Glu Pro Tyr Leu Gly Leu His Tyr Pro Ala
            260                 265                 270

Thr Asp Ile Pro Gln Ala Ala Arg Phe Leu Phe Met Lys Asn Arg Val
            275                 280                 285

Arg Ile Ile Cys Asp Cys Ser Ala Pro Pro Val Lys Val Ile Gln Asp
            290                 295                 300

Pro Thr Met Lys His Pro Ile Ser Leu Ala Gly Ser Thr Leu Arg Gly
305                 310                 315                 320

Val His Gly Cys His Ala Gln Tyr Met Ala Asn Met Gly Ser Val Ala
                325                 330                 335

Ser Leu Val Met Ala Val Ile Ile Asn Asp Asn Ser Ser Glu Glu Gly
            340                 345                 350

Ala Thr Ala Ala Gly Gly Ile Leu His Lys Gly Arg Lys Leu Trp Gly
            355                 360                 365

Leu Val Val Cys His His Ser Ser Pro Arg Tyr Val Pro Phe Pro Leu
370                 375                 380

Arg Ser Ala Cys Glu Phe Leu Met Gln Val Phe Gly Leu Gln Leu Asn
385                 390                 395                 400

Met Glu Val Glu Leu Ser Ser Gln Leu Arg Glu Lys His Ile Leu Arg
                405                 410                 415

Thr Gln Thr Leu Leu Cys Asp Met Leu Leu Arg Asp Ala Pro Met Gly
            420                 425                 430

Ile Val Ser Gln Ser Pro Asn Ile Thr Asp Leu Val Lys Cys Asp Gly
            435                 440                 445

Ala Ala Leu Phe Tyr His Gly Arg Ala Trp Leu Leu Gly Val Thr Pro
            450                 455                 460

Ser Glu Ala Gln Val Arg Asp Ile Ala Ala Trp Leu Leu Asp Ser His
465                 470                 475                 480

Lys Asp Ser Thr Gly Leu Ser Thr Asp Ser Leu Ala Asp Ala Gly Tyr
                485                 490                 495

Pro Asn Ala Asp Ser Leu Gly Val Ser Val Cys Gly Met Ala Ala Ala
            500                 505                 510

Arg Ile Thr Ser Lys Asp Phe Leu Phe Trp Phe Arg Ser His Ala Gln
            515                 520                 525

Lys Glu Val Lys Trp Ala Gly Ala Lys Gln Glu Pro Gly Asp Arg Asp
            530                 535                 540

Arg Glu Glu Gly Glu Glu Gly Arg Met His Pro Arg Ser Ser Phe
545                 550                 555                 560

Gln Ala Phe Leu Glu Val Val Lys Gln Arg Ser Leu Pro Trp Glu Asp
                565                 570                 575

Val Glu Met Asp Ala Ile His Ser Leu Gln Leu Ile Leu Arg Gly Ser
            580                 585                 590
```

Phe Gln Asp Met Glu Gly Glu Gly Gly Ser Gln Gln Gly Asn Lys
            595                 600                 605

Arg Met Ile
    610

<210> SEQ ID NO 5
<211> LENGTH: 528
<212> TYPE: PRT
<213> ORGANISM: Artificial Sequence
<220> FEATURE:
<223> OTHER INFORMATION: Description of Artificial Sequence:: Sequence
      alignment Fig. 6 S6603phy1

<400> SEQUENCE: 5

Met Ala Thr Thr Val Gln Leu Ser Asp Gln Ser Leu Arg Gln Leu Glu
  1               5                  10                  15

Thr Leu Ala Ile His Thr Ala His Leu Ile Gln Pro His Gly Leu Val
             20                  25                  30

Val Val Leu Gln Glu Pro Asp Leu Thr Ile Ser Gln Ile Ser Ala Asn
         35                  40                  45

Cys Thr Gly Ile Leu Gly Arg Ser Pro Glu Asp Leu Leu Gly Arg Thr
 50                  55                  60

Leu Gly Glu Val Phe Asp Ser Phe Gln Ile Asp Pro Ile Gln Ser Arg
 65                  70                  75                  80

Leu Thr Ala Gly Gln Ile Ser Ser Leu Asn Pro Ser Lys Leu Trp Ala
                 85                  90                  95

Arg Val Met Gly Asp Asp Phe Val Ile Phe Asp Gly Val Phe His Arg
            100                 105                 110

Asn Ser Asp Gly Leu Leu Val Cys Glu Leu Glu Pro Ala Tyr Thr Ser
        115                 120                 125

Asp Asn Leu Pro Phe Leu Gly Phe Tyr His Met Ala Asn Ala Ala Leu
    130                 135                 140

Asn Arg Leu Arg Gln Gln Ala Asn Leu Arg Asp Phe Tyr Asp Val Ile
145                 150                 155                 160

Val Glu Glu Val Arg Arg Met Thr Gly Phe Asp Arg Val Met Leu Tyr
                165                 170                 175

Arg Phe Asp Glu Asn Asn His Gly Asp Val Ile Ala Glu Asp Lys Arg
            180                 185                 190

Asp Asp Met Glu Pro Tyr Leu Gly Leu His Tyr Pro Glu Ser Asp Ile
        195                 200                 205

Pro Gln Pro Ala Arg Arg Leu Phe Ile His Asn Pro Ile Arg Val Ile
    210                 215                 220

Pro Asp Val Tyr Gly Val Ala Val Pro Leu Thr Pro Ala Val Asn Pro
225                 230                 235                 240

Ser Thr Asn Arg Ala Val Asp Leu Thr Glu Ser Ile Leu Arg Ser Ala
                245                 250                 255

Tyr His Cys His Leu Thr Tyr Leu Lys Asn Met Gly Val Gly Ala Ser
            260                 265                 270

Leu Thr Ile Ser Leu Ile Lys Asp Gly His Leu Trp Gly Leu Ile Ala
        275                 280                 285

Cys His His Gln Thr Pro Lys Val Ile Pro Phe Glu Leu Arg Lys Ala
    290                 295                 300

Cys Glu Phe Phe Gly Arg Val Val Phe Ser Asn Ile Ser Ala Gln Glu
305                 310                 315                 320

Asp Thr Glu Thr Phe Asp Tyr Arg Val Gln Leu Ala Glu His Glu Ala
                325                 330                 335

-continued

Val Leu Leu Asp Lys Met Thr Thr Ala Ala Asp Phe Val Glu Gly Leu
            340                 345                 350

Thr Asn His Pro Asp Arg Leu Leu Gly Leu Thr Gly Ser Gln Gly Ala
        355                 360                 365

Ala Ile Cys Phe Gly Glu Lys Leu Ile Leu Val Gly Glu Thr Pro Asp
    370                 375                 380

Glu Lys Ala Val Gln Tyr Leu Leu Gln Trp Leu Glu Asn Arg Glu Val
385                 390                 395                 400

Gln Asp Val Phe Phe Thr Ser Ser Leu Ser Gln Ile Tyr Pro Asp Ala
                405                 410                 415

Val Asn Phe Lys Ser Val Ala Ser Gly Leu Leu Ala Ile Pro Ile Ala
            420                 425                 430

Arg His Asn Phe Leu Leu Trp Phe Arg Pro Glu Val Leu Gln Thr Val
        435                 440                 445

Asn Trp Gly Gly Asp Pro Asn His Ala Tyr Glu Ala Thr Gln Glu Asp
    450                 455                 460

Gly Lys Ile Glu Leu His Pro Arg Gln Ser Phe Asp Leu Trp Lys Glu
465                 470                 475                 480

Ile Val Arg Leu Gln Ser Leu Pro Trp Gln Ser Val Glu Ile Gln Ser
                485                 490                 495

Ala Leu Ala Leu Lys Lys Ala Ile Val Asn Leu Ile Leu Arg Gln Ala
            500                 505                 510

Glu Glu Leu Ala Gln Leu Ala Arg Asn Leu Glu Arg Ser Asn Ala Asp
        515                 520                 525

<210> SEQ ID NO 6
<211> LENGTH: 748
<212> TYPE: PRT
<213> ORGANISM: Artificial Sequence
<220> FEATURE:
<223> OTHER INFORMATION: Description of Artificial Sequence: Fig 10B seq

<400> SEQUENCE: 6

Met Ala Thr Thr Val Gln Leu Ser Asp Gln Ser Leu Arg Gln Leu Glu
1               5                   10                  15

Thr Leu Ala Ile His Thr Ala His Leu Ile Gln Pro His Gly Leu Val
            20                  25                  30

Val Val Leu Gln Glu Pro Asp Leu Thr Ile Ser Gln Ile Ser Ala Asn
        35                  40                  45

Cys Thr Gly Ile Leu Gly Arg Ser Pro Glu Asp Leu Leu Gly Arg Thr
    50                  55                  60

Leu Gly Glu Val Phe Asp Ser Phe Gln Ile Asp Pro Ile Gln Ser Arg
65                  70                  75                  80

Leu Thr Ala Gly Gln Ile Ser Ser Leu Asn Pro Ser Lys Leu Trp Ala
                85                  90                  95

Arg Val Met Gly Asp Asp Phe Val Ile Phe Asp Gly Val Phe His Arg
            100                 105                 110

Asn Ser Asp Gly Leu Leu Val Cys Glu Leu Glu Pro Ala Tyr Thr Ser
        115                 120                 125

Asp Asn Leu Pro Phe Leu Gly Phe Tyr His Met Ala Asn Ala Ala Leu
    130                 135                 140

Asn Arg Leu Arg Gln Gln Ala Asn Leu Arg Asp Phe Tyr Asp Val Ile
145                 150                 155                 160

Val Glu Glu Val Arg Arg Met Thr Gly Phe Asp Arg Val Met Leu Tyr
                165                 170                 175

-continued

```
Arg Phe Asp Glu Asn Asn His Gly Asp Val Ile Ala Glu Asp Lys Arg
            180                 185                 190
Asp Asp Met Glu Pro Tyr Leu Gly Leu His Tyr Pro Glu Ser Asp Ile
        195                 200                 205
Pro Gln Pro Ala Arg Arg Leu Phe Ile His Asn Pro Ile Arg Val Ile
    210                 215                 220
Pro Asp Val Tyr Gly Val Ala Val Pro Leu Thr Pro Ala Val Asn Pro
225                 230                 235                 240
Ser Thr Asn Arg Ala Val Asp Leu Thr Glu Ser Ile Leu Arg Ser Ala
                245                 250                 255
Tyr His Cys His Leu Thr Tyr Leu Lys Asn Met Gly Val Gly Ala Ser
            260                 265                 270
Leu Thr Ile Ser Leu Ile Lys Asp Gly His Leu Trp Gly Leu Ile Ala
        275                 280                 285
Cys His His Gln Thr Pro Lys Val Ile Pro Phe Glu Leu Arg Lys Ala
    290                 295                 300
Cys Glu Phe Phe Gly Arg Val Phe Ser Asn Ile Ser Ala Gln Glu
305                 310                 315                 320
Asp Thr Glu Thr Phe Asp Tyr Arg Val Gln Leu Ala Glu His Glu Ala
                325                 330                 335
Val Leu Leu Asp Lys Met Thr Thr Ala Ala Asp Phe Val Glu Gly Leu
            340                 345                 350
Thr Asn His Pro Asp Arg Leu Leu Gly Leu Thr Gly Ser Gln Gly Ala
        355                 360                 365
Ala Ile Cys Phe Gly Glu Lys Leu Ile Leu Val Gly Glu Thr Pro Asp
    370                 375                 380
Glu Lys Ala Val Gln Tyr Leu Leu Gln Trp Leu Glu Asn Arg Glu Val
385                 390                 395                 400
Gln Asp Val Phe Phe Thr Ser Ser Leu Ser Gln Ile Tyr Pro Asp Ala
                405                 410                 415
Val Asn Phe Lys Ser Val Ala Ser Gly Leu Leu Ala Ile Pro Ile Ala
            420                 425                 430
Arg His Asn Phe Leu Leu Trp Phe Arg Pro Glu Val Leu Gln Thr Val
        435                 440                 445
Asn Trp Gly Gly Asp Pro Asn His Ala Tyr Glu Ala Thr Gln Glu Asp
    450                 455                 460
Gly Lys Ile Glu Leu His Pro Arg Gln Ser Phe Asp Leu Trp Lys Glu
465                 470                 475                 480
Ile Val Arg Leu Gln Ser Leu Pro Trp Gln Ser Val Glu Ile Gln Ser
                485                 490                 495
Ala Leu Ala Leu Lys Lys Ala Ile Val Asn Leu Ile Leu Arg Gln Ala
            500                 505                 510
Glu Glu Leu Ala Gln Leu Ala Arg Asn Leu Glu Arg Ser Asn Ala Asp
        515                 520                 525
Leu Lys Lys Phe Ala Tyr Ile Ala Ser His Asp Leu Gln Glu Pro Leu
    530                 535                 540
Asn Gln Val Ser Asn Tyr Val Gln Leu Leu Glu Met Arg Tyr Ser Glu
545                 550                 555                 560
Ala Leu Asp Glu Asp Ala Lys Asp Phe Ile Asp Phe Ala Val Thr Gly
                565                 570                 575
Val Ser Leu Met Gln Thr Leu Ile Asp Asp Ile Leu Thr Tyr Ala Lys
            580                 585                 590
```

Val Asp Thr Gln Tyr Ala Gln Leu Thr Phe Thr Asp Val Gln Glu Val
            595                 600                 605

Val Asp Lys Ala Leu Ala Asn Leu Lys Gln Arg Ile Glu Glu Ser Gly
        610                 615                 620

Ala Glu Ile Glu Val Gly Ser Met Pro Ala Val Met Ala Asp Gln Ile
625                 630                 635                 640

Gln Leu Met Gln Val Phe Gln Asn Leu Ile Ala Asn Gly Ile Lys Phe
                645                 650                 655

Ala Gly Asp Lys Ser Pro Lys Ile Lys Ile Trp Gly Asp Arg Gln Glu
            660                 665                 670

Asp Ala Trp Val Phe Ala Val Gln Asp Asn Gly Ile Gly Ile Asp Pro
        675                 680                 685

Gln Phe Phe Glu Arg Ile Phe Val Ile Phe Gln Arg Leu His Thr Arg
            690                 695                 700

Asp Glu Tyr Lys Gly Thr Gly Met Gly Leu Ala Ile Cys Lys Lys Ile
705                 710                 715                 720

Ile Glu Gly His Gln Gly Gln Ile Trp Leu Glu Ser Asn Pro Gly Glu
                725                 730                 735

Gly Ser Thr Phe Tyr Phe Ser Ile Pro Ile Gly Asn
            740                 745

<210> SEQ ID NO 7
<211> LENGTH: 147
<212> TYPE: PRT
<213> ORGANISM: Artificial Sequence
<220> FEATURE:
<223> OTHER INFORMATION: Description of Artificial Sequence:Fig.10C Rcp1

<400> SEQUENCE: 7

Met Ser Asp Glu Ser Asn Pro Pro Lys Val Ile Leu Leu Val Glu Asp
 1               5                  10                  15

Ser Lys Ala Asp Ser Arg Leu Val Gln Glu Val Leu Lys Thr Ser Thr
            20                  25                  30

Ile Asp His Glu Leu Ile Ile Leu Arg Asp Gly Leu Ala Ala Met Ala
        35                  40                  45

Phe Leu Gln Gln Gln Gly Glu Tyr Glu Asn Ser Pro Arg Pro Asn Leu
    50                  55                  60

Ile Leu Leu Asp Leu Asn Leu Pro Lys Lys Asp Gly Arg Glu Val Leu
65                  70                  75                  80

Ala Glu Ile Lys Gln Asn Pro Asp Leu Lys Arg Ile Pro Val Val Val
                85                  90                  95

Leu Thr Thr Ser His Asn Glu Asp Asp Val Ile Ala Ser Tyr Glu Leu
            100                 105                 110

His Val Asn Cys Tyr Leu Thr Lys Ser Arg Asn Leu Lys Asp Leu Phe
        115                 120                 125

Lys Met Val Gln Gly Ile Glu Ser Phe Trp Leu Glu Thr Val Thr Leu
    130                 135                 140

Pro Ala Ala
145

<210> SEQ ID NO 8
<211> LENGTH: 124
<212> TYPE: PRT
<213> ORGANISM: Artificial Sequence
<220> FEATURE:
<223> OTHER INFORMATION: Description of Artificial Sequence:Fig.10C Rcaf

<400> SEQUENCE: 8

```
Met Gln Thr Lys Arg Ile Leu Ile Ile Asp Asp Glu Glu Thr Ile Gln
  1               5                  10                  15

Thr Val Val Gln Phe Gly Ile Lys Met Ala Ala Gly Trp Glu Val Phe
             20                  25                  30

Thr Ala Ser Ser Gly Phe Glu Gly Ile Gln Ala Ala Gln Thr Ala Lys
             35                  40                  45

Pro Asp Ala Ile Leu Leu Asp Val Met Met Pro Asp Met Asp Gly Ile
 50                  55                  60

Ala Thr Phe Lys Glu Leu Gln Ser His Ser Glu Thr Glu Gln Ile Pro
 65                  70                  75                  80

Val Ile Leu Leu Thr Ala Lys Ala Gln Thr Ala Glu Lys Arg Gln Phe
             85                  90                  95

Asn Asp Leu Gly Val Ser Gly Val Ile Thr Lys Pro Phe Asn Ser Leu
            100                 105                 110

Asp Leu Pro Glu Gln Ile Ser Arg Ile Leu His Trp
            115                 120
```

```
<210> SEQ ID NO 9
<211> LENGTH: 129
<212> TYPE: PRT
<213> ORGANISM: Artificial Sequence
<220> FEATURE:
<223> OTHER INFORMATION: Description of Artificial Sequence: Fig.10C
      Chey

<400> SEQUENCE: 9
```

```
Met Ala Asp Lys Glu Leu Lys Phe Leu Val Val Asp Asp Phe Ser Thr
  1               5                  10                  15

Met Arg Arg Ile Val Arg Asn Leu Leu Lys Glu Leu Gly Phe Asn Asn
             20                  25                  30

Val Glu Glu Ala Glu Asp Gly Val Asp Ala Leu Asn Lys Leu Gln Ala
             35                  40                  45

Gly Gly Tyr Gly Phe Val Ile Ser Asp Trp Asn Met Pro Asn Met Asp
 50                  55                  60

Gly Leu Glu Leu Leu Lys Thr Ile Arg Ala Asp Gly Ala Met Ser Ala
 65                  70                  75                  80

Leu Pro Val Leu Met Val Thr Ala Glu Ala Lys Lys Glu Asn Ile Ile
             85                  90                  95

Ala Ala Ala Gln Ala Gly Ala Ser Gly Tyr Val Val Lys Pro Phe Thr
            100                 105                 110

Ala Ala Thr Leu Glu Glu Lys Leu Asn Lys Ile Phe Glu Lys Leu Gly
            115                 120                 125

Met
```

```
<210> SEQ ID NO 10
<211> LENGTH: 124
<212> TYPE: PRT
<213> ORGANISM: Artificial Sequence
<220> FEATURE:
<223> OTHER INFORMATION: Description of Artificial Sequence:Fig.10C
      SpoOF

<400> SEQUENCE: 10
```

```
Met Met Asn Glu Lys Ile Leu Ile Val Asp Asp Gln Tyr Gly Ile Arg
  1               5                  10                  15

Ile Leu Leu Asn Glu Val Phe Asn Lys Glu Gly Tyr Gln Thr Phe Gln
             20                  25                  30
```

```
Ala Ala Asn Gly Leu Gln Ala Leu Asp Ile Val Thr Lys Glu Arg Pro
            35                  40                  45

Asp Leu Val Leu Leu Asp Met Lys Ile Pro Gly Met Asp Gly Ile Glu
        50                  55                  60

Ile Leu Lys Arg Met Lys Val Ile Asp Glu Asn Ile Arg Val Ile Ile
65                  70                  75                  80

Met Thr Ala Tyr Gly Glu Leu Asp Met Ile Gln Glu Ser Lys Glu Leu
                85                  90                  95

Gly Ala Leu Thr His Phe Ala Lys Pro Phe Asp Ile Asp Glu Ile Arg
                    100                 105                 110

Asp Ala Val Lys Lys Tyr Leu Pro Leu Lys Ser Asn
            115                 120
```

<210> SEQ ID NO 11
<211> LENGTH: 1129
<212> TYPE: PRT
<213> ORGANISM: Oat (Avena)

<400> SEQUENCE: 11

```
Met Ser Ser Ser Arg Pro Ala Ser Ser Ser Ser Arg Asn Arg Gln
1               5                   10                  15

Ser Ser Gln Ala Arg Val Leu Ala Gln Thr Thr Leu Asp Ala Glu Leu
            20                  25                  30

Asn Ala Glu Tyr Glu Glu Ser Gly Asp Ser Phe Asp Tyr Ser Lys Leu
            35                  40                  45

Val Glu Ala Gln Arg Asp Gly Pro Pro Val Gln Gln Gly Arg Ser Glu
        50                  55                  60

Lys Val Ile Ala Tyr Leu Gln His Ile Gln Lys Gly Lys Leu Ile Gln
65                  70                  75                  80

Thr Phe Gly Cys Leu Leu Ala Leu Asp Glu Lys Ser Phe Asn Val Ile
                85                  90                  95

Ala Phe Ser Glu Asn Ala Pro Glu Met Leu Thr Thr Val Ser His Ala
                    100                 105                 110

Val Pro Ser Val Asp Asp Pro Arg Leu Gly Ile Gly Thr Asn Val
            115                 120                 125

Arg Ser Leu Phe Ser Asp Gln Gly Ala Thr Ala Leu His Lys Ala Leu
        130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                165                 170                 175

Leu Val Val Asp Phe Glu Pro Val Lys Pro Thr Glu Phe Pro Ala Thr
                    180                 185                 190

Ala Ala Gly Ala Leu Gln Ser Tyr Lys Leu Ala Ala Lys Ala Ile Ser
            195                 200                 205

Lys Ile Gln Ser Leu Pro Gly Gly Ser Met Glu Val Leu Cys Asn Thr
        210                 215                 220

Val Val Lys Glu Val Phe Asp Leu Thr Gly Tyr Asp Arg Val Met Ala
225                 230                 235                 240

Tyr Lys Phe His Glu Asp Asp His Gly Glu Val Phe Ser Glu Ile Thr
                245                 250                 255

Lys Pro Gly Leu Glu Pro Tyr Leu Gly Leu His Tyr Pro Ala Thr Asp
                    260                 265                 270

Ile Pro Gln Ala Ala Arg Leu Leu Phe Met Lys Asn Lys Val Arg Met
            275                 280                 285
```

-continued

```
Ile Cys Asp Cys Arg Ala Arg Ser Ile Lys Val Ile Glu Ala Glu Ala
290                 295                 300

Leu Pro Phe Asp Ile Ser Leu Cys Gly Ser Ala Leu Arg Ala Pro His
305                 310                 315                 320

Ser Cys His Leu Gln Tyr Met Glu Asn Met Asn Ser Ile Ala Ser Leu
            325                 330                 335

Val Met Ala Val Val Asn Glu Asn Glu Glu Asp Asp Glu Ala Glu
            340                 345                 350

Ser Glu Gln Pro Ala Gln Gln Lys Lys Lys Leu Trp Gly Leu
            355                 360                 365

Leu Val Cys His His Glu Ser Pro Arg Tyr Val Pro Phe Pro Leu Arg
370                 375                 380

Tyr Ala Cys Glu Phe Leu Ala Gln Val Phe Ala Val His Val Asn Arg
385                 390                 395                 400

Glu Phe Glu Leu Glu Lys Gln Leu Arg Glu Lys Asn Ile Leu Lys Met
                405                 410                 415

Gln Thr Met Leu Ser Asp Met Leu Phe Arg Glu Ala Ser Pro Leu Thr
                420                 425                 430

Ile Val Ser Gly Thr Pro Asn Ile Met Asp Leu Val Lys Cys Asp Gly
                435                 440                 445

Ala Ala Leu Leu Tyr Gly Gly Lys Val Trp Arg Leu Arg Asn Ala Pro
450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
                485                 490                 495

Pro Gly Ala Ala Ala Leu Gly Asp Met Ile Cys Gly Met Ala Val Ala
                500                 505                 510

Lys Ile Asn Ser Lys Asp Ile Leu Phe Trp Phe Arg Ser His Thr Ala
                515                 520                 525

Ala Glu Ile Arg Trp Gly Gly Ala Lys Asn Asp Pro Ser Asp Met Asp
                530                 535                 540

Asp Ser Arg Arg Met His Pro Arg Leu Ser Phe Lys Ala Phe Leu Glu
545                 550                 555                 560

Val Val Lys Met Lys Ser Leu Pro Trp Ser Asp Tyr Glu Met Asp Ala
                565                 570                 575

Ile His Ser Leu Gln Leu Ile Leu Arg Gly Thr Leu Asn Asp Ala Ser
                580                 585                 590

Lys Pro Lys Arg Glu Ala Ser Leu Asp Asn Gln Ile Gly Asp Leu Lys
                595                 600                 605

Leu Asp Gly Leu Ala Glu Leu Gln Ala Val Thr Ser Glu Met Val Arg
                610                 615                 620

Leu Met Glu Thr Ala Thr Val Pro Ile Leu Ala Val Asp Gly Asn Gly
625                 630                 635                 640

Leu Val Asn Gly Trp Asn Gln Lys Ala Ala Glu Leu Thr Gly Leu Arg
                645                 650                 655

Val Asp Asp Ala Ile Gly Arg His Ile Leu Thr Leu Val Glu Asp Ser
                660                 665                 670

Ser Val Pro Val Val Gln Arg Met Leu Tyr Leu Ala Leu Gln Gly Lys
            675                 680                 685

Glu Glu Lys Glu Val Arg Phe Glu Val Lys Thr His Gly Pro Lys Arg
690                 695                 700
```

-continued

```
Asp Asp Gly Pro Val Ile Leu Val Val Asn Ala Cys Ala Ser Arg Asp
705                 710                 715                 720

Leu His Asp His Val Gly Val Cys Phe Val Ala Gln Asp Met Thr
                725                 730                 735

Val His Lys Leu Val Met Asp Lys Phe Thr Arg Val Glu Gly Asp Tyr
                740                 745                 750

Lys Ala Ile Ile His Asn Pro Asn Pro Leu Ile Pro Pro Ile Phe Gly
                755                 760                 765

Ala Asp Glu Phe Gly Trp Cys Ser Glu Trp Asn Ala Ala Met Thr Lys
770                 775                 780

Leu Thr Gly Trp Asn Arg Asp Glu Val Leu Asp Lys Met Leu Leu Gly
785                 790                 795                 800

Glu Val Phe Asp Ser Ser Asn Ala Ser Cys Pro Leu Lys Asn Arg Asp
                805                 810                 815

Ala Phe Val Ser Leu Cys Val Leu Ile Asn Ser Ala Leu Ala Gly Glu
                820                 825                 830

Glu Thr Glu Lys Ala Pro Phe Gly Phe Phe Asp Arg Ser Gly Lys Tyr
                835                 840                 845

Ile Glu Cys Leu Leu Ser Ala Asn Arg Lys Glu Asn Glu Gly Gly Leu
850                 855                 860

Ile Thr Gly Val Phe Cys Phe Ile His Val Ala Ser His Glu Leu Gln
865                 870                 875                 880

His Ala Leu Gln Val Gln Gln Ala Ser Glu Gln Thr Ser Leu Lys Arg
                885                 890                 895

Leu Lys Ala Phe Ser Tyr Met Arg His Ala Ile Asn Asn Pro Leu Ser
                900                 905                 910

Gly Met Leu Tyr Ser Arg Lys Ala Leu Lys Asn Thr Asp Leu Asn Glu
                915                 920                 925

Glu Gln Met Lys Gln Ile His Val Gly Asp Asn Cys His His Gln Ile
                930                 935                 940

Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Leu Gln Asp Val Val
                965                 970                 975

Val Ala Ala Val Ser Gln Val Leu Ile Thr Cys Gln Gly Lys Gly Ile
                980                 985                 990

Arg Ile Ser Cys Asn Leu Pro Glu Arg Phe Met Lys Gln Ser Val Tyr
                995                 1000                1005

Gly Asp Gly Val Arg Leu Gln Gln Ile Leu Ser Asp Phe Leu Phe Ile
                1010                1015                1020

Ser Val Lys Phe Ser Pro Val Gly Gly Ser Val Glu Ile Ser Ser Lys
1025                1030                1035                1040

Leu Thr Lys Asn Ser Ile Gly Glu Asn Leu His Leu Ile Asp Leu Glu
                1045                1050                1055

Leu Arg Ile Lys His Gln Gly Leu Gly Val Pro Ala Glu Leu Met Ala
                1060                1065                1070

Gln Met Phe Glu Glu Asp Asn Lys Glu Gln Ser Glu Glu Gly Leu Ser
                1075                1080                1085

Leu Leu Val Ser Arg Asn Leu Arg Leu Met Asn Gly Asp Val Arg
                1090                1095                1100

His Leu Arg Glu Ala Gly Val Ser Thr Phe Ile Ile Thr Ala Glu Leu
1105                1110                1115                1120

Ala Ser Ala Pro Thr Ala Met Gly Gln
```

-continued

```
                        1125
```

<210> SEQ ID NO 12
<211> LENGTH: 1142
<212> TYPE: PRT
<213> ORGANISM: Alga (Mesotaeinum)

<400> SEQUENCE: 12

```
Met Ser Thr Ser Arg Met Ser Gln Ser Ser Gly Glu Ser Thr Ala Lys
  1               5                  10                  15

Thr Lys Arg Glu Val Arg Val Ala Gln Ala Thr Ala Asp Ala Lys Leu
             20                  25                  30

Asn Thr Ala Phe Glu Ala Ser Ala Ala Val Gly Gly Ser Phe Asp Tyr
         35                  40                  45

Thr Lys Ser Val Gly Ala Ser Leu Asn Ala Gly Ser Glu Ala Ile Pro
     50                  55                  60

Ser Ser Ala Val Thr Ala Tyr Leu Gln Arg Met Gln Arg Gly Gly Ile
 65                  70                  75                  80

Thr Gln Thr Phe Gly Cys Met Leu Met Val Glu Glu Gly Ser Phe Arg
                 85                  90                  95

Val Arg Ala Phe Ser Glu Asn Ala Gly Glu Met Leu Asp Leu Val Pro
            100                 105                 110

Gln Ala Val Pro Ser Met Gly Gln Gln Ser Leu Ile Ala Val Gly Thr
        115                 120                 125

Asp Ile Arg Thr Leu Phe Thr Ser Ala Ser Val Ser Leu Leu Glu Lys
    130                 135                 140

Ala Ala Met Ala Thr Asp Val Ser Val Met Asn Pro Val Ser Leu Gln
145                 150                 155                 160

Ser Arg Ala Ala Lys Lys Pro Phe Phe Ala Val Leu His Arg Ile Asp
                165                 170                 175

Val Gly Leu Val Val Asp Leu Glu Pro Val Arg Pro Ser Asp Pro Asn
            180                 185                 190

Val Ser Ala Ala Gly Ala Met Gln Ser His Lys Leu Ala Ala Lys Ala
        195                 200                 205

Ile Ser Arg Leu Gln Ser Leu Pro Gly Gly Asp Ile Gly Leu Leu Cys
    210                 215                 220

Asp Ala Val Val Glu Glu Val Arg Glu Leu Thr Gly Tyr Asp Arg Val
225                 230                 235                 240

Met Ala Tyr Lys Phe His Glu Asp Glu His Gly Glu Val Ile Ala Glu
                245                 250                 255

Ile Arg Arg Ser Asp Leu Glu Pro Tyr Leu Gly Leu His Tyr Pro Ala
            260                 265                 270

Thr Asp Ile Pro Gln Ala Ala Arg Phe Leu Phe Met Lys Asn Arg Val
        275                 280                 285

Arg Ile Ile Cys Asp Cys Ser Ala Pro Val Lys Val Ile Gln Asp
    290                 295                 300

Pro Thr Met Lys His Pro Ile Ser Leu Ala Gly Ser Thr Leu Arg Gly
305                 310                 315                 320

Val His Gly Cys His Ala Gln Tyr Met Ala Asn Met Gly Ser Val Ala
                325                 330                 335

Ser Leu Val Met Ala Val Ile Asn Asp Asn Ser Ser Glu Glu Gly
            340                 345                 350

Ala Thr Ala Ala Gly Gly Ile Leu His Lys Gly Arg Lys Leu Trp Gly
        355                 360                 365
```

-continued

```
Leu Val Val Cys His His Ser Ser Pro Arg Tyr Val Pro Phe Pro Leu
    370                 375                 380
Arg Ser Ala Cys Glu Phe Leu Met Gln Val Phe Gly Leu Gln Leu Asn
385                 390                 395                 400
Met Glu Val Glu Leu Ser Ser Gln Leu Arg Glu Lys His Ile Leu Arg
                405                 410                 415
Thr Gln Thr Leu Leu Cys Asp Met Leu Leu Arg Asp Ala Pro Met Gly
            420                 425                 430
Ile Val Ser Gln Ser Pro Asn Ile Thr Asp Leu Val Lys Cys Asp Gly
        435                 440                 445
Ala Ala Leu Phe Tyr His Gly Arg Ala Trp Leu Leu Gly Val Thr Pro
    450                 455                 460
Ser Glu Ala Gln Val Arg Asp Ile Ala Ala Trp Leu Leu Asp Ser His
465                 470                 475                 480
Lys Asp Ser Thr Gly Leu Ser Thr Asp Ser Leu Ala Asp Ala Gly Tyr
                485                 490                 495
Pro Asn Ala Asp Ser Leu Gly Val Ser Val Cys Gly Met Ala Ala Ala
            500                 505                 510
Arg Ile Thr Ser Lys Asp Phe Leu Phe Trp Phe Arg Ser His Ala Gln
        515                 520                 525
Lys Glu Val Lys Trp Ala Gly Ala Lys Gln Glu Pro Gly Asp Arg Asp
    530                 535                 540
Arg Glu Glu Gly Glu Glu Gly Arg Met His Pro Arg Ser Ser Phe
545                 550                 555                 560
Gln Ala Phe Leu Glu Val Val Lys Gln Arg Ser Leu Pro Trp Glu Asp
                565                 570                 575
Val Glu Met Asp Ala Ile His Ser Leu Gln Leu Ile Leu Arg Gly Ser
            580                 585                 590
Phe Gln Asp Met Glu Gly Glu Gly Gly Ser Gln Gln Gly Asn Lys
        595                 600                 605
Arg Met Ile Asn Ala Arg Leu Asn Asp Leu Lys Leu Gln Gly Met Asp
    610                 615                 620
Glu Leu Ser Thr Val Ala Asn Glu Met Val Arg Leu Ile Glu Thr Ala
625                 630                 635                 640
Thr Ala Pro Ile Leu Ala Val Asp Ser Leu Gly Cys Val Asn Gly Trp
                645                 650                 655
Asn Ala Lys Val Ser Glu Leu Thr Gly Leu Pro Val Ser Glu Ala Met
            660                 665                 670
Gly Lys Ser Leu Val Lys Asp Leu Val Gln Arg Glu Ser Arg Glu Ala
        675                 680                 685
Val Glu Arg Val Leu Tyr Met Ala Leu Asn Gly Glu Glu Gln Asn
    690                 695                 700
Val Glu Ile Gln Leu Lys Thr Trp Gly Pro Gln Leu His Ser His Gly
705                 710                 715                 720
Gly Thr Val Ile Leu Val Val Asn Ala Cys Ala Ser Arg Asp Val Ser
                725                 730                 735
Glu Ser Val Val Gly Val Cys Phe Val Gly Gln Asp Val Thr Gly Glu
            740                 745                 750
Lys Glu Val Leu Asp Lys Phe Ile Arg Ile Gln Gly Asp Tyr Thr Thr
        755                 760                 765
Ile Val Arg Ser Arg Asn Ser Leu Ile Pro Pro Ile Phe Gly Ser Asp
    770                 775                 780
Glu Tyr Gly Cys Cys Thr Glu Trp Asn Pro Ala Met Glu Lys Leu Thr
```

```
                785                 790                 795                 800

Gly Val Arg Arg Glu Asp Val Ile Gly Arg Met Leu Met Gly Asp Val
                    805                 810                 815

Phe Gly Ser Ala Leu Arg Leu Arg Gly Ser Asp Gly Leu Thr Gln Phe
                820                 825                 830

Met Ile Val Leu Asn Arg Ala Met Asp Gly Ala Asp Thr Asp Lys Phe
                835                 840                 845

Pro Phe Thr Phe Tyr Asp Arg Glu Gly Lys Cys Val Asp Ser Leu Leu
            850                 855                 860

Thr Ala Asn Lys Arg Thr Asp Ala Asp Gly Ala Ile Thr Gly Val Phe
865                 870                 875                 880

Cys Phe Leu His Thr Val Ser Leu Glu Leu Gln Gln Ala Leu Ser Val
                    885                 890                 895

Gln Lys Ala Ala Glu Arg Val Ala Glu Ala Lys Ala Lys Glu Leu Ala
                900                 905                 910

Tyr Ile Arg Gln Glu Ile Gln Asn Pro Leu Asp Gly Ile His Phe Ala
            915                 920                 925

Arg Ser Phe Ile Glu His Thr Glu Leu Ser Glu Asp Gln Lys Gln Leu
        930                 935                 940

Met Glu Thr Ser Ala Thr Cys Glu Lys Gln Leu Arg Arg Ile Leu Asp
945                 950                 955                 960

Asp Met Asp Leu Glu Ser Ile Glu Glu Gly Tyr Leu Glu Leu Glu Thr
                965                 970                 975

Gly Glu Phe Met Met Ala Thr Val Met Asn Ser Val Val Ser Gln Gly
                    980                 985                 990

Met Val Gln Ser Ser Lys Lys Gly Leu Gln Leu Phe Cys Asp Thr Pro
                995                 1000                1005

Pro Glu Phe Lys Ser Met Cys Val Phe Gly Asp Gln Val Arg Leu Gln
            1010                1015                1020

Gln Val Leu Ala Asp Phe Leu Met Asn Ala Val Gln Phe Thr Pro Ala
1025                1030                1035                1040

Ser Gly Trp Val Glu Ile Lys Val Val Pro Asn Val Arg Ser Leu Pro
                    1045                1050                1055

Gly Gly Ile Thr Met Ala His Met Glu Phe Arg Val Thr His Ser Gly
                1060                1065                1070

Glu Gly Leu Pro Glu Asp Leu Val His Gln Met Phe Asp Arg Ala Asp
            1075                1080                1085

Ala His Ser Lys Ser Gln Glu Gly Leu Gly Leu Ser Met Cys Arg Lys
1090                1095                1100

Ile Val Arg Leu Met Ser Gly Glu Val Arg Tyr Val Arg Glu Pro Gly
1105                1110                1115                1120

Lys Ser Tyr Phe Leu Val Leu Asp Leu Pro Leu Ala Gln Arg Glu
                1125                1130                1135

Asp Ala Gly Ser Ala Met
            1140

<210> SEQ ID NO 13
<211> LENGTH: 748
<212> TYPE: PRT
<213> ORGANISM: Unknown
<220> FEATURE:
<223> OTHER INFORMATION: Description of Unknown Organism:Cyanobacteria
      (Synechocystis)

<400> SEQUENCE: 13
```

-continued

```
Met Ala Thr Thr Val Gln Leu Ser Asp Gln Ser Leu Arg Gln Leu Glu
 1               5                  10                  15

Thr Leu Ala Ile His Thr Ala His Leu Ile Gln Pro His Gly Leu Val
                 20                  25                  30

Val Val Leu Gln Glu Pro Asp Leu Thr Ile Ser Gln Ile Ser Ala Asn
                 35                  40                  45

Cys Thr Gly Ile Leu Gly Arg Ser Pro Glu Asp Leu Leu Gly Arg Thr
 50                  55                  60

Leu Gly Glu Val Phe Asp Ser Phe Gln Ile Asp Pro Ile Gln Ser Arg
 65                  70                  75                  80

Leu Thr Ala Gly Gln Ile Ser Ser Leu Asn Pro Ser Lys Leu Trp Ala
                 85                  90                  95

Arg Val Met Gly Asp Asp Phe Val Ile Phe Asp Gly Val Phe His Arg
                100                 105                 110

Asn Ser Asp Gly Leu Leu Val Cys Glu Leu Glu Pro Ala Tyr Thr Ser
                115                 120                 125

Asp Asn Leu Pro Phe Leu Gly Phe Tyr His Met Ala Asn Ala Ala Leu
                130                 135                 140

Asn Arg Leu Arg Gln Gln Ala Asn Leu Arg Asp Phe Tyr Asp Val Ile
145                 150                 155                 160

Val Glu Glu Val Arg Arg Met Thr Gly Phe Asp Arg Val Met Leu Tyr
                165                 170                 175

Arg Phe Asp Glu Asn Asn His Gly Asp Val Ile Ala Glu Asp Lys Arg
                180                 185                 190

Asp Asp Met Glu Pro Tyr Leu Gly Leu His Tyr Pro Glu Ser Asp Ile
                195                 200                 205

Pro Gln Pro Ala Arg Arg Leu Phe Ile His Asn Pro Ile Arg Val Ile
                210                 215                 220

Pro Asp Val Tyr Gly Val Ala Val Pro Leu Thr Pro Ala Val Asn Pro
225                 230                 235                 240

Ser Thr Asn Arg Ala Val Asp Leu Thr Glu Ser Ile Leu Arg Ser Ala
                245                 250                 255

Tyr His Cys His Leu Thr Tyr Leu Lys Asn Met Gly Val Gly Ala Ser
                260                 265                 270

Leu Thr Ile Ser Leu Ile Lys Asp Gly His Leu Trp Gly Leu Ile Ala
                275                 280                 285

Cys His His Gln Thr Pro Lys Val Ile Pro Phe Glu Leu Arg Lys Ala
                290                 295                 300

Cys Glu Phe Phe Gly Arg Val Val Phe Ser Asn Ile Ser Ala Gln Glu
305                 310                 315                 320

Asp Thr Glu Thr Phe Asp Tyr Arg Val Gln Leu Ala Glu His Glu Ala
                325                 330                 335

Val Leu Leu Asp Lys Met Thr Ala Ala Asp Phe Val Glu Gly Leu
                340                 345                 350

Thr Asn His Pro Asp Arg Leu Leu Gly Leu Thr Gly Ser Gln Gly Ala
                355                 360                 365

Ala Ile Cys Phe Gly Glu Lys Leu Ile Leu Val Gly Glu Thr Pro Asp
                370                 375                 380

Glu Lys Ala Val Gln Tyr Leu Leu Gln Trp Leu Glu Asn Arg Glu Val
385                 390                 395                 400

Gln Asp Val Phe Phe Thr Ser Ser Leu Ser Gln Ile Tyr Pro Asp Ala
                405                 410                 415

Val Asn Phe Lys Ser Val Ala Ser Gly Leu Leu Ala Ile Pro Ile Ala
```

```
                420             425             430
Arg His Asn Phe Leu Leu Trp Phe Arg Pro Glu Val Leu Gln Thr Val
            435             440             445
Asn Trp Gly Gly Asp Pro Asn His Ala Tyr Glu Ala Thr Gln Glu Asp
450             455             460
Gly Lys Ile Glu Leu His Pro Arg Gln Ser Phe Asp Leu Trp Lys Glu
465             470             475             480
Ile Val Arg Leu Gln Ser Leu Pro Trp Gln Ser Val Glu Ile Gln Ser
            485             490             495
Ala Leu Ala Leu Lys Lys Ala Ile Val Asn Leu Ile Leu Arg Gln Ala
            500             505             510
Glu Glu Leu Ala Gln Leu Ala Arg Asn Leu Glu Arg Ser Asn Ala Asp
            515             520             525
Leu Lys Lys Phe Ala Tyr Ile Ala Ser His Asp Leu Gln Glu Pro Leu
            530             535             540
Asn Gln Val Ser Asn Tyr Val Gln Leu Leu Glu Met Arg Tyr Ser Glu
545             550             555             560
Ala Leu Asp Glu Asp Ala Lys Asp Phe Ile Asp Phe Ala Val Thr Gly
                565             570             575
Val Ser Leu Met Gln Thr Leu Ile Asp Asp Ile Leu Thr Tyr Ala Lys
            580             585             590
Val Asp Thr Gln Tyr Ala Gln Leu Thr Phe Thr Asp Val Gln Glu Val
            595             600             605
Val Asp Lys Ala Leu Ala Asn Leu Lys Gln Arg Ile Glu Glu Ser Gly
            610             615             620
Ala Glu Ile Glu Val Gly Ser Met Pro Ala Val Met Ala Asp Gln Ile
625             630             635             640
Gln Leu Met Gln Val Phe Gln Asn Leu Ile Ala Asn Gly Ile Lys Phe
                645             650             655
Ala Gly Asp Lys Ser Pro Lys Ile Lys Ile Trp Gly Asp Arg Gln Glu
                660             665             670
Asp Ala Trp Val Phe Ala Val Gln Asp Asn Gly Ile Gly Ile Asp Pro
            675             680             685
Gln Phe Phe Glu Arg Ile Phe Val Ile Phe Gln Arg Leu His Thr Arg
            690             695             700
Asp Glu Tyr Lys Gly Thr Gly Met Gly Leu Ala Ile Cys Lys Lys Ile
705             710             715             720
Ile Glu Gly His Gln Gly Ile Trp Leu Glu Ser Asn Pro Gly Glu
                725             730             735
Gly Ser Thr Phe Tyr Phe Ser Ile Pro Ile Gly Asn
            740             745

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence:Hind2Bgl
      oligomer

<400> SEQUENCE: 14
agcttcagat ctga                                                       14

<210> SEQ ID NO 15
<211> LENGTH: 30
<212> TYPE: DNA
```

-continued

```
<213> ORGANISM: Artificial Sequence
<220> FEATURE:
<223> OTHER INFORMATION: Description of Artificial Sequence:S6801phy
      N514 Sal" antisense primer

<400> SEQUENCE: 15
gcgtcgacca ccttcttctg cctggcgcaa                                   30

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: S6801phy
      sense primer

<400> SEQUENCE: 16
gcactagtta acgagggcaa aaaatgccca ccaccgtac                         39
```